United States Patent
Scheller et al.

(10) Patent No.: US 8,951,245 B2
(45) Date of Patent: *Feb. 10, 2015

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/856,540

(22) Filed: Apr. 4, 2013

(65) Prior Publication Data

US 2013/0304044 A1   Nov. 14, 2013

Related U.S. Application Data

(60) Provisional application No. 61/644,773, filed on May 9, 2012.

(51) Int. Cl.
*A61F 9/008* (2006.01)
*A61B 18/00* (2006.01)
*A61B 18/22* (2006.01)

(52) U.S. Cl.
CPC ......... *A61F 9/00821* (2013.01); *A61F 9/00823* (2013.01); *A61B 2018/00589* (2013.01); *A61B 2018/2238* (2013.01); *A61B 2018/225* (2013.01); *A61F 2009/00863* (2013.01)
USPC .......................................................... 606/4

(58) Field of Classification Search
CPC ................. A61B 17/2909; A61B 2017/00367; A61B 2017/2913; A61B 2017/2918; A61B 2017/00424; A61B 2017/0042; A61B 2018/00589; A61B 2018/2238; A61B 2018/225; A61F 9/00821; A61F 9/00823; A61F 2009/00863

See application file for complete search history.

(56) References Cited

U.S. PATENT DOCUMENTS

| | | |
|---|---|---|
| 5,190,050 A | 3/1993 | Nitzsche |
| 5,355,871 A | 10/1994 | Hurley et al. |
| 5,381,782 A | 1/1995 | DeLaRama et al. |
| 5,439,000 A | 8/1995 | Gunderson et al. |

(Continued)

FOREIGN PATENT DOCUMENTS

| | | |
|---|---|---|
| EP | 0900547 B1 | 3/1999 |
| WO | WO 2006/091597 A1 | 8/2006 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Gary Jackson
*Assistant Examiner* — Scott T. Luan
(74) *Attorney, Agent, or Firm* — Kevin P. Rollins

(57) ABSTRACT

A steerable laser probe may include a handle, an actuation structure of the handle, a housing tube, a wire having a preformed curve, and an optic fiber disposed within the housing tube and an inner bore of the handle. The housing tube may include a first housing tube portion having a first stiffness and a second housing tube portion having a second stiffness. The second stiffness may be greater than the first stiffness. A compression of the actuation structure may curve or straighten the housing tube. A decompression of the actuation structure may curve or straighten the housing tube.

20 Claims, 38 Drawing Sheets

(56) References Cited

U.S. PATENT DOCUMENTS

| | | | | |
|---|---|---|---|---|
| 5,454,794 | A | 10/1995 | Narciso et al. | |
| 5,520,222 | A | 5/1996 | Chikama | |
| 6,123,699 | A | 9/2000 | Webster, Jr. | |
| 6,126,654 | A | 10/2000 | Giba et al. | |
| 6,198,974 | B1 | 3/2001 | Webster, Jr. | |
| 6,488,695 | B1 | 12/2002 | Hickingbotham | |
| 6,530,913 | B1 | 3/2003 | Giba et al. | |
| 6,551,302 | B1 | 4/2003 | Rosinko et al. | |
| 6,572,608 | B1 | 6/2003 | Lee et al. | |
| 6,620,153 | B2 | 9/2003 | Mueller et al. | |
| 6,730,076 | B2 | 5/2004 | Hickingbotham | |
| 6,863,668 | B2 | 3/2005 | Gillespie et al. | |
| 6,984,230 | B2 | 1/2006 | Scheller et al. | |
| 7,004,957 | B1 | 2/2006 | Dampney et al. | |
| 7,303,533 | B2 | 12/2007 | Johansen et al. | |
| 7,402,158 | B2 | 7/2008 | Scheller et al. | |
| 7,473,249 | B2 * | 1/2009 | Scheller et al. | 606/15 |
| 7,632,242 | B2 | 12/2009 | Griffin et al. | |
| 7,766,904 | B2 | 8/2010 | Mc Gowan, Sr. et al. | |
| 8,038,692 | B2 | 10/2011 | Valencia et al. | |
| 8,075,553 | B2 | 12/2011 | Scheller et al. | |
| 8,197,468 | B2 | 6/2012 | Scheller et al. | |
| 2003/0171762 | A1 * | 9/2003 | Forchette et al. | 606/139 |
| 2004/0181138 | A1 | 9/2004 | Hindricks et al. | |
| 2005/0054900 | A1 | 3/2005 | Mawn et al. | |
| 2005/0157985 | A1 | 7/2005 | McGowan, Sr. et al. | |
| 2005/0272975 | A1 | 12/2005 | McWeeny et al. | |
| 2007/0179475 | A1 * | 8/2007 | Scheller | 606/1 |
| 2007/0185514 | A1 * | 8/2007 | Kirchhevel | 606/171 |
| 2009/0018393 | A1 | 1/2009 | Dick et al. | |
| 2009/0187170 | A1 | 7/2009 | Auld et al. | |
| 2009/0312750 | A1 | 12/2009 | Spaide | |
| 2010/0004642 | A1 * | 1/2010 | Lumpkin | 606/4 |
| 2010/0268234 | A1 * | 10/2010 | Aho et al. | 606/80 |
| 2011/0028947 | A1 * | 2/2011 | Scheller et al. | 606/1 |
| 2012/0116361 | A1 * | 5/2012 | Hanlon et al. | 606/1 |
| 2013/0035551 | A1 * | 2/2013 | Yu et al. | 600/141 |
| 2013/0060240 | A1 | 3/2013 | Scheller et al. | |
| 2013/0071507 | A1 | 3/2013 | Scheller et al. | |
| 2013/0096541 | A1 | 4/2013 | Scheller et al. | |
| 2013/0116671 | A1 | 5/2013 | Scheller et al. | |
| 2013/0150838 | A1 | 6/2013 | Scheller et al. | |
| 2013/0165910 | A1 | 6/2013 | Scheller et al. | |

* cited by examiner

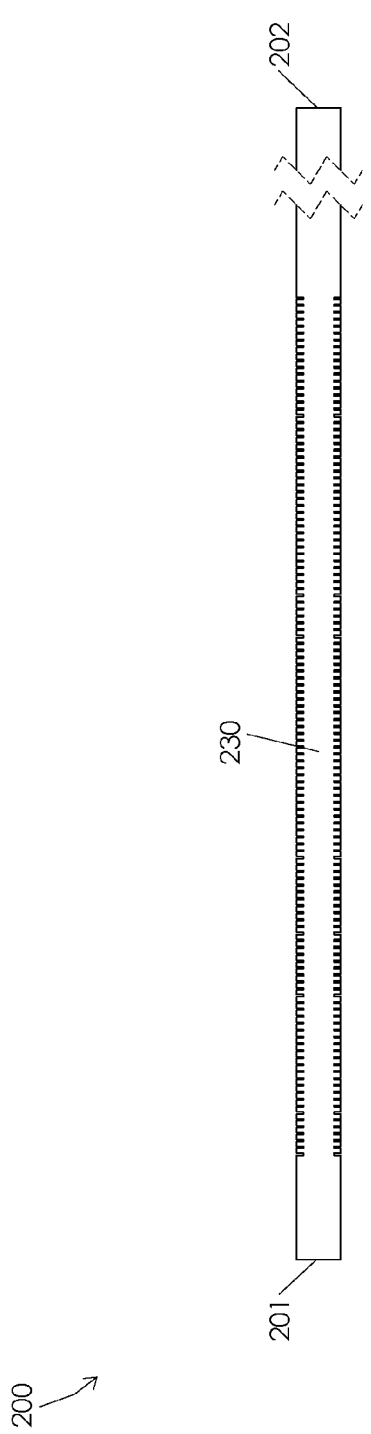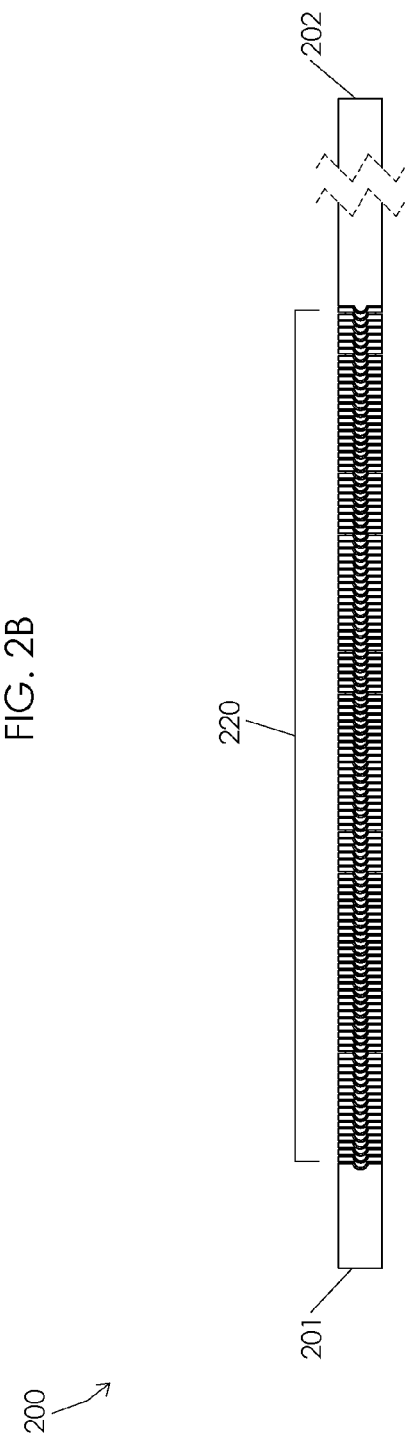

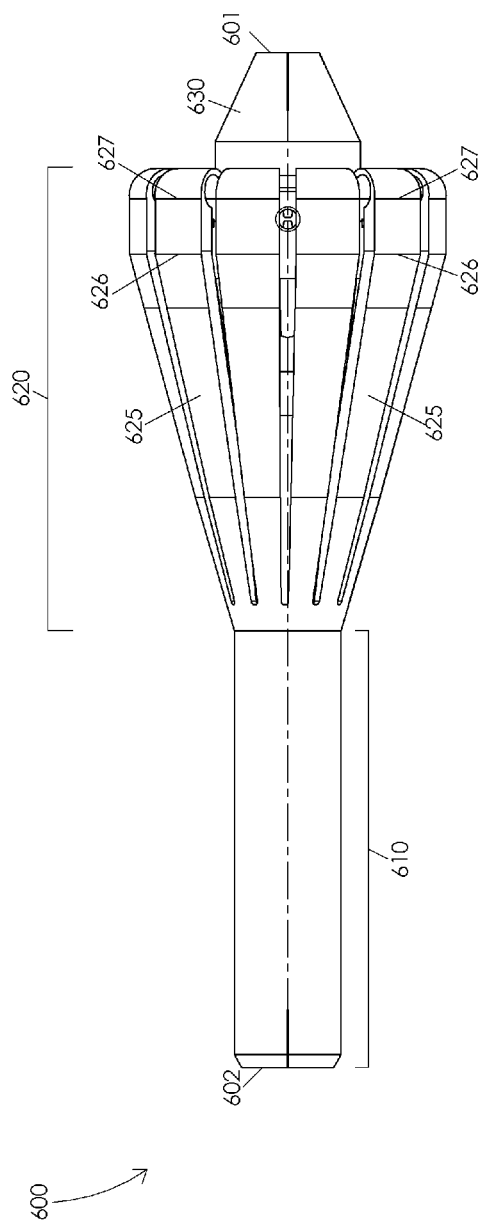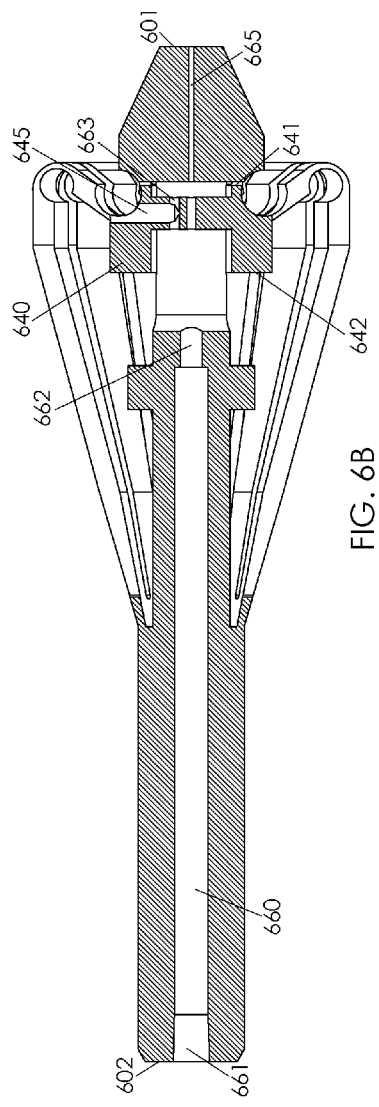
FIG. 6A
FIG. 6B

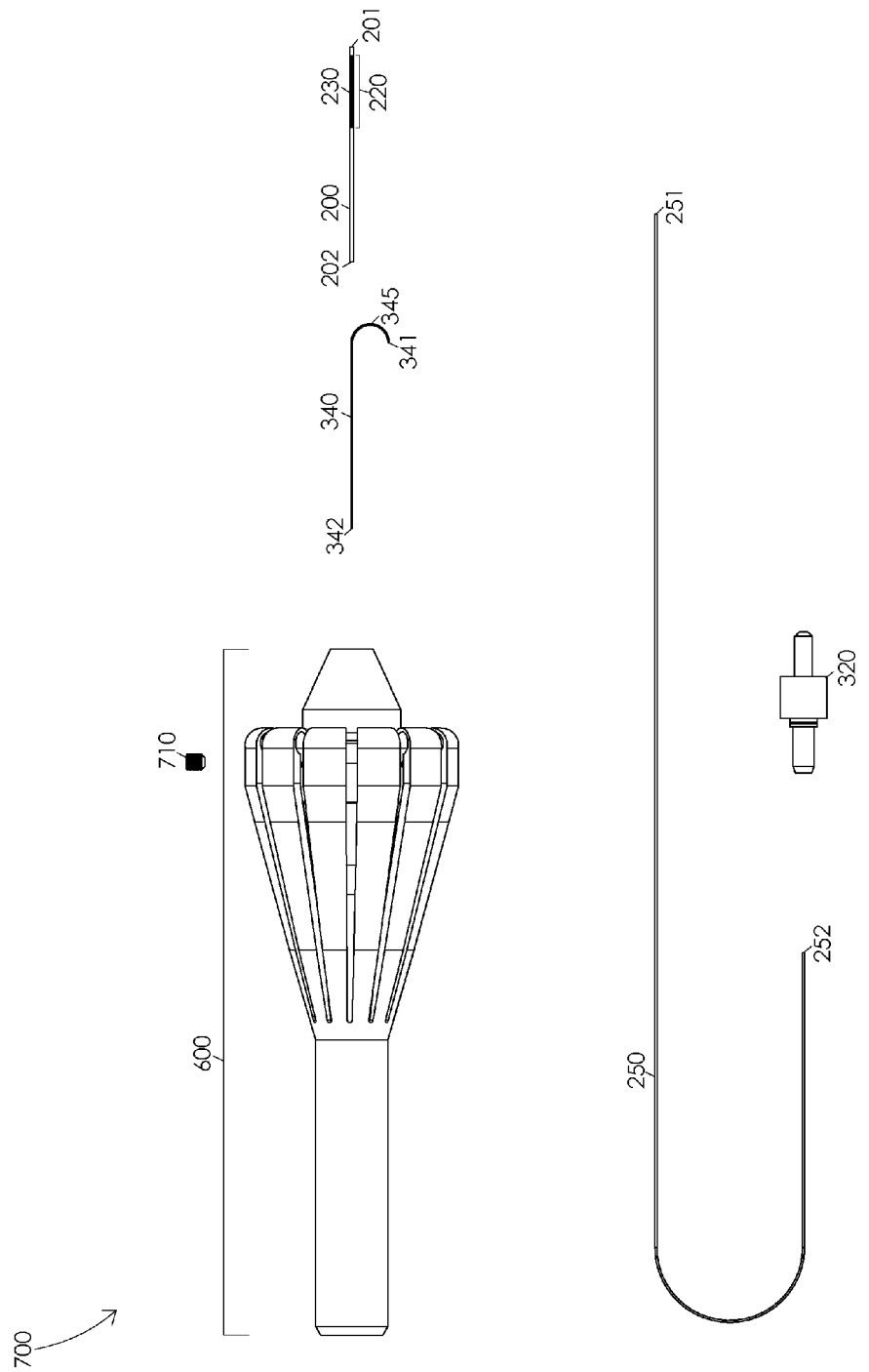

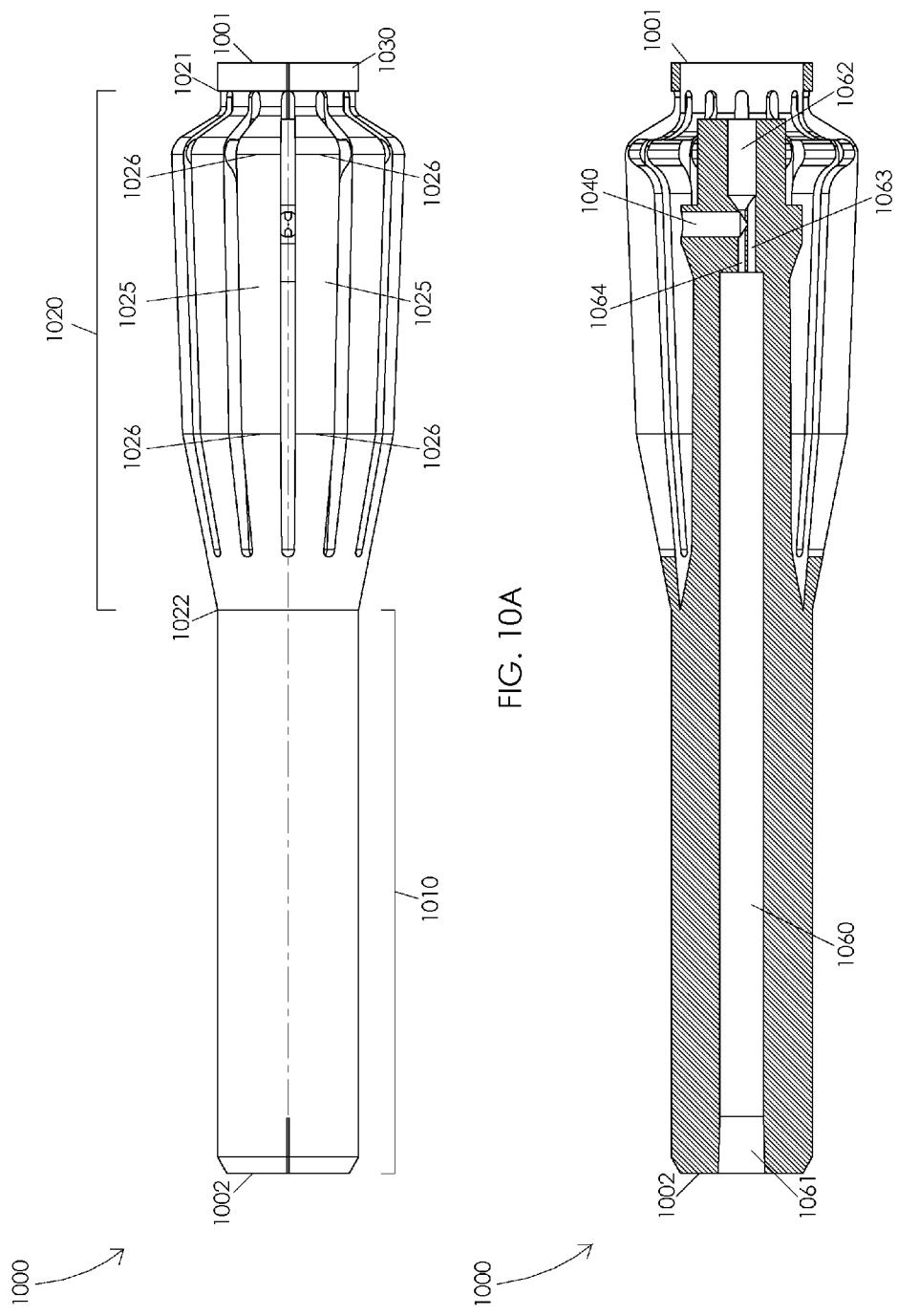

STEERABLE LASER PROBE

CROSS-REFERENCE TO RELATED APPLICATIONS

This application claims the benefit of U.S. Provisional Application No. 61/644,773, filed May 9, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. In one or more embodiments, a steerable laser probe may comprise a handle, an actuation structure of the handle, a housing tube, a wire having a pre-formed curve, and an optic fiber disposed within the housing tube and an inner bore of the handle. Illustratively, the housing tube may comprise a first housing tube portion having a first stiffness and a second housing tube portion having a second stiffness. In one or more embodiments, the second stiffness may be greater than the first stiffness.

Illustratively, a compression of the actuation structure may be configured to gradually curve the housing tube. In one or more embodiments, a gradual curving of the housing tube may be configured to gradually curve the optic fiber. Illustratively, a decompression of the actuation structure may be configured to gradually straighten the housing tube. In one or more embodiments, a gradual straightening of the housing tube may be configured to gradually straighten the optic fiber.

Illustratively, a decompression of the actuation structure may be configured to gradually curve the housing tube. In one or more embodiments, a gradual curving of the housing tube may be configured to gradually curve the optic fiber. Illustratively, a compression of the actuation structure may be configured to gradually straighten the housing tube. In one or more embodiments, a gradual straightening of the housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 2A, 2B, and 2C are schematic diagrams illustrating a housing tube;

FIGS. 6A and 6B are schematic diagrams illustrating a handle;

FIG. 7 is a schematic diagram illustrating an exploded view of a steerable laser probe assembly;

FIGS. 10A and 10B are schematic diagrams illustrating a handle;

DETAILED DESCRIPTION OF AN ILLUSTRATIVE EMBODIMENT

Figure 1A:
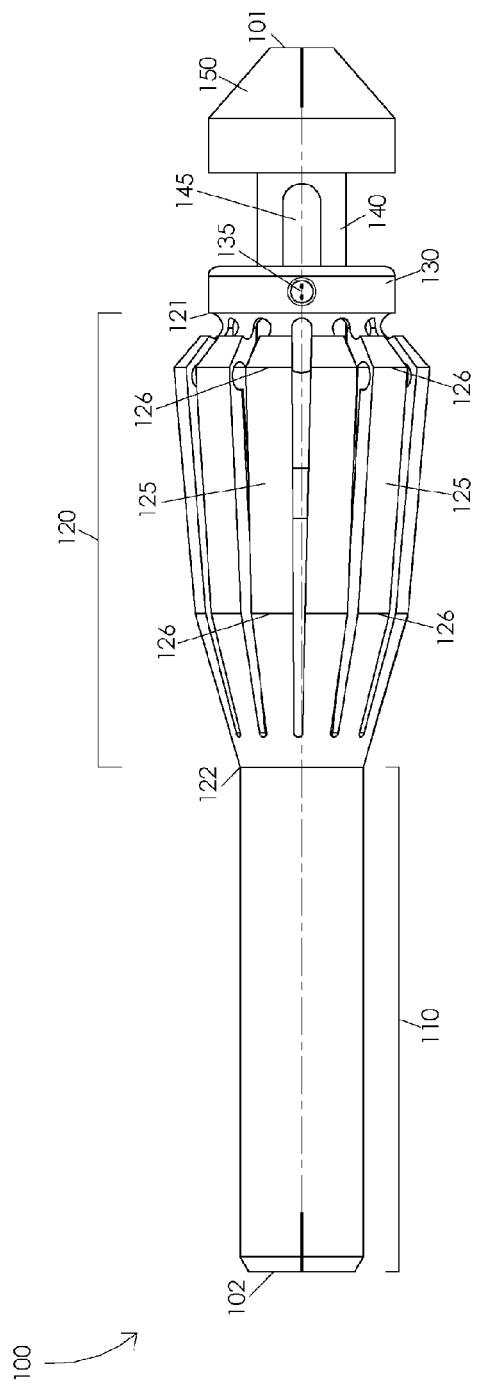
FIGS. 1A and 1B are schematic diagrams illustrating a handle.
Figure 1B:
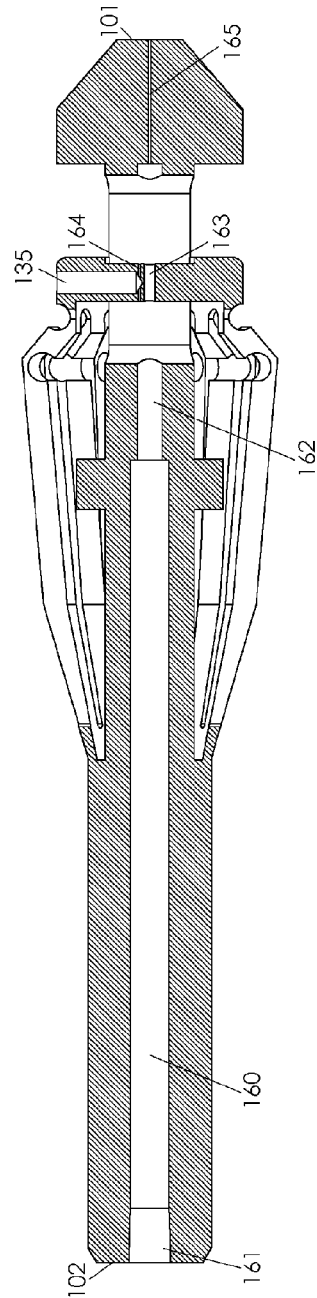

FIGS. 1A and 1B are schematic diagrams illustrating a handle 100. FIG. 1A illustrates a top view of handle 100. In one or more embodiments, handle 100 may comprise a handle distal end 101, a handle proximal end 102, a handle base 110, an actuation structure 120, an actuation ring 130, an actuation mechanism housing 135, a platform base 140, an actuation mechanism guide 145, and a housing tube platform 150. Illustratively, actuation structure 120 may comprise an actuation structure distal end 121 and an actuation structure proximal end 122. In one or more embodiments, actuation structure 120 may comprise a plurality of actuation arms 125. Illustratively, each actuation arm 125 may comprise at least one extension mechanism 126. In one or more embodiments, actuation structure 120 may comprise a shape memory material configured to project actuation structure distal end 121 a first distance from actuation structure proximal end 122, e.g., when actuation structure 120 is fully decompressed. Illustratively, actuation structure 120 may comprise a shape memory material configured to project actuation structure distal end 121 a second distance from actuation structure proximal end 122, e.g., when actuation structure 120 is fully compressed. In one or more embodiments, the second distance from actuation structure proximal end 122 may be greater than the first distance from actuation structure proximal end 122. Actuation structure 120 may be manufactured from any suitable material, e.g., polymers, metals, metal alloys, etc., or from any combination of suitable materials.

Illustratively, actuation structure 120 may be compressed by an application of a compressive force to actuation structure 120. In one or more embodiments, actuation structure 120 may be compressed by an application of one or more compressive forces located at one or more locations around an outer perimeter of actuation structure 120. Illustratively, the one or more locations may comprise any of a plurality of locations around the outer perimeter of actuation structure 120. For example, a surgeon may compress actuation structure 120 by squeezing actuation structure 120. Illustratively, the surgeon may compress actuation structure 120 by squeezing actuation structure 120 at any particular location of a plurality of locations around an outer perimeter of actuation structure 120. For example, a surgeon may rotate handle 100 and compress actuation structure 120 from any rotational position of a plurality of rotational positions of handle 100.

In one or more embodiments, actuation structure 120 may be compressed by an application of a compressive force to any one or more of the plurality of actuation arms 125. Illustratively, each actuation arm 125 may be configured to actuate independently. In one or more embodiments, each actuation arm 125 may be connected to one or more of the plurality of actuation arms 125 wherein an actuation of a particular actuation arm 125 may be configured to actuate every actuation arm 125 of the plurality of actuation arms 125. Illustratively, one or more actuation arms 125 may be configured to actuate in pairs or groups. For example, an actuation of a first actuation arm 125 may be configured to actuate a second actuation arm 125.

In one or more embodiments, a compression of actuation structure 120, e.g., due to an application of a compressive force to a particular actuation arm 125, may be configured to actuate the particular actuation arm 125. Illustratively, an actuation of the particular actuation arm 125 may be configured to actuate every actuation arm 125 of the plurality of actuation arms 125. In one or more embodiments, an application of a compressive force to a particular actuation arm 125 may be configured to extend at least one extension mechanism 126 of the particular actuation arm 125. Illustratively, a particular actuation arm 125 may be configured to extend a first length from handle base 110. An extension of an extension mechanism 126 of the particular actuation arm 125, e.g., due to an application of a compressive force to the particular actuation arm 125, may be configured to extend the particular actuation arm 125 a second length from handle base 110. Illustratively, the second length from handle base 110 may be greater than the first length from handle base 110.

In one or more embodiments, actuation ring 130 may be fixed to actuation structure distal end 121. Illustratively, a compression of actuation structure 120 may be configured to gradually extend actuation ring 130 from handle base 110. For example, actuation ring 130 may be configured to extend a first distance from actuation structure proximal end 122, e.g., when actuation structure 120 is fully decompressed. Actuation ring 130 may be configured to extend a second distance from actuation structure proximal end 122, e.g., due to a compression of actuation structure 120. Illustratively, the second distance from actuation structure proximal end 122 may be greater than the first distance from actuation structure proximal end 122.

FIG. 1B illustrates a cross-sectional view of handle 100. In one or more embodiments, handle 100 may comprise an inner bore 160, an inner bore proximal taper 161, an inner bore distal chamber 162, an optic fiber proximal guide 163, a wire housing 164, and an optic fiber distal guide 165. Handle 100 may be manufactured from any suitable material, e.g., polymers, metals, metal alloys, etc., or from any combination of suitable materials.

Figure 2C:
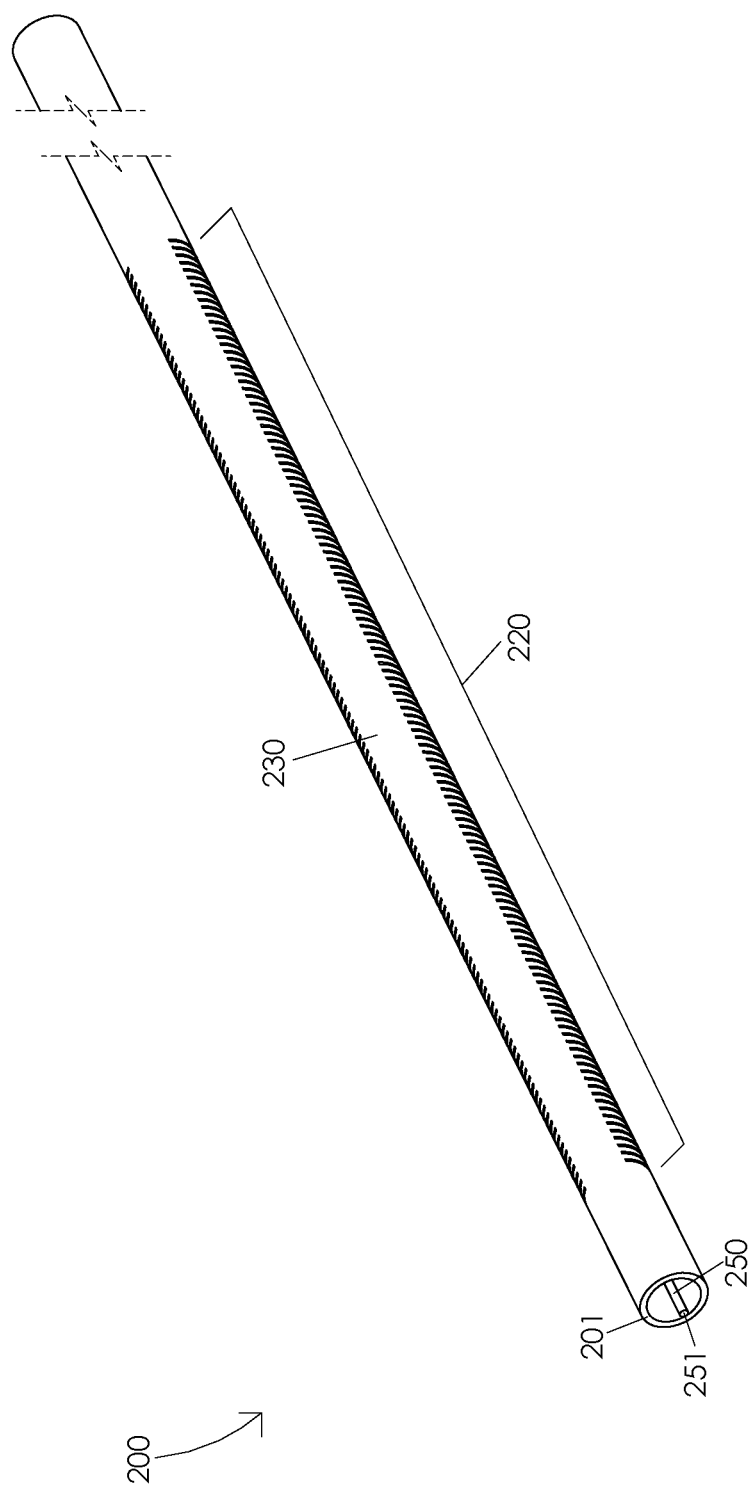

FIGS. 2A, 2B, and 2C are schematic diagrams illustrating a housing tube 200. In one or more embodiments, housing tube 200 may comprise a housing tube distal end 201 and a housing tube proximal end 202. Housing tube 200 may be manufactured from any suitable material, e.g., polymers, metals, metal alloys, etc., or from any combination of suitable materials. Illustratively, housing tube 200 may be manufactured at dimensions configured to perform microsurgical procedures, e.g., ophthalmic surgical procedures.

FIG. 2A illustrates a housing tube 200 oriented to illustrate a first housing tube portion 220. Illustratively, first housing tube portion 220 may have a first stiffness. FIG. 2B illustrates a housing tube 200 oriented to illustrate a second housing tube portion 230. Illustratively, second housing tube portion 230 may have a second stiffness. In one or more embodiments, the second stiffness may be greater than the first stiffness. Illustratively, first housing tube portion 220 may comprise a first material having a first stiffness. In one or more embodiments, second housing tube portion 230 may comprise a second material having a second stiffness. Illustratively, the second stiffness may be greater than the first stiffness.

In one or more embodiments, housing tube 200 may comprise a non-uniform inner diameter or a non-uniform outer diameter, e.g., to vary a stiffness of one or more portions of housing tube 200. Illustratively, a first housing tube portion 220 may comprise a first inner diameter of housing tube 200 and a second housing tube portion 230 may comprise a second inner diameter of housing tube 200. In one or more embodiments, the first inner diameter of housing tube 200 may be larger than the second inner diameter of housing tube 200. Illustratively, a first housing tube portion 220 may comprise a first outer diameter of housing tube 200 and a second housing tube portion 230 may comprise a second outer diameter of housing tube 200. In one or more embodiments, the first outer diameter of housing tube 200 may be smaller than the second outer diameter of housing tube 200.

In one or more embodiments, first housing tube portion 220 may comprise one or more apertures configured to produce a first stiffness of first housing tube portion 220. Illustratively, second housing tube portion 230 may comprise a solid portion of housing tube 200 having a second stiffness. In one or more embodiments, the second stiffness may be greater than the first stiffness. Illustratively, first housing tube portion 220 may comprise one or more apertures configured to produce a first stiffness of first housing tube portion 220. In one or more embodiments, second housing tube portion 230 may comprise one or more apertures configured to produce a second stiffness of second housing tube portion 230. Illustratively, the second stiffness may be greater than the first stiffness.

In one or more embodiments, first housing tube portion 220 may comprise a plurality of slits configured to separate one or more solid portions of housing tube 200. Illustratively, a plurality of slits may be cut, e.g., laser cut, into first housing tube portion 220. In one or more embodiments, first housing tube portion 220 may comprise a plurality of slits configured to minimize a force of friction between housing tube 200 and a cannula, e.g., as housing tube 200 is inserted into the cannula or as housing tube 200 is extracted from the cannula. For example, each slit of the plurality of slits may comprise one or more arches configured to minimize a force of friction between housing tube 200 and a cannula.

FIG. 2C illustrates an angled view of housing tube 200. Illustratively, an optic fiber 250 may be disposed within housing tube 200. In one or more embodiments, optic fiber 250 may be disposed within housing tube 200 wherein an optic fiber distal end 251 is adjacent to housing tube distal end 201. Illustratively, optic fiber 250 may be disposed within housing tube 200 wherein optic fiber 250 may be adjacent to a portion of first housing tube portion 220. In one or more embodiments, a portion of optic fiber 250 may be fixed to an inner portion of housing tube 200, e.g., by an adhesive or any suitable fixation means.

Figure 3:
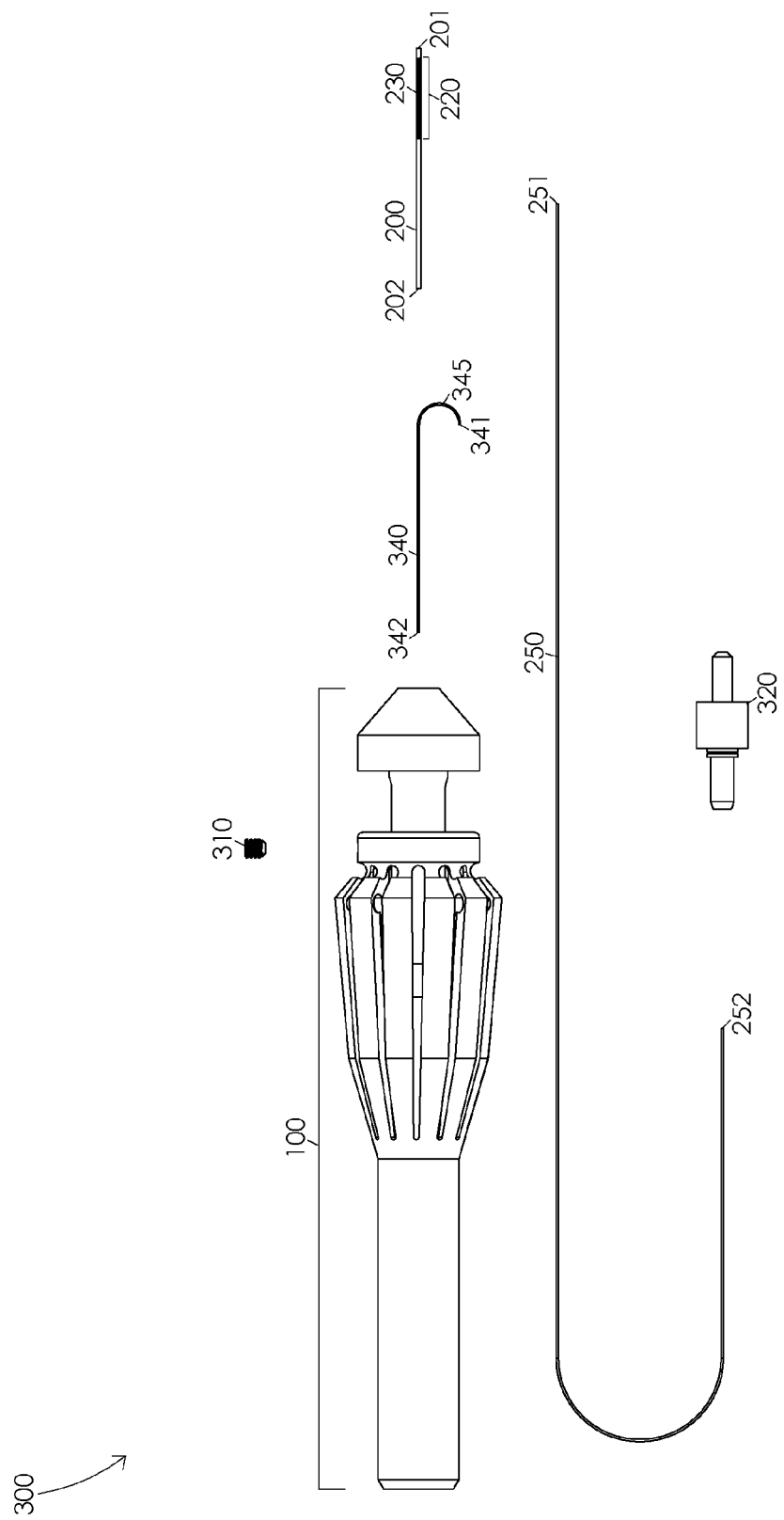
FIG. 3 is a schematic diagram illustrating an exploded view of a steerable laser probe assembly.

FIG. 3 is a schematic diagram illustrating an exploded view of a steerable laser probe assembly 300. In one or more embodiments, steerable laser probe assembly 300 may comprise a handle 100, a housing tube 200 having a housing tube distal end 201 and a housing tube proximal end 202, an optic fiber 250 having an optic fiber distal end 251 and an optic fiber proximal end 252, a wire 340 having a wire distal end 341 and a wire proximal end 342, an actuation mechanism 310, and a light source interface 320. Illustratively, light source interface 320 may be configured to interface with optic fiber 250, e.g., at optic fiber proximal end 252. In one or more embodiments, light source interface 320 may comprise a standard light source connector, e.g., an SMA connector.

Illustratively, housing tube 200 may be fixed to housing tube platform 150, e.g., housing tube proximal end 202 may be fixed to handle proximal end 101. In one or more embodiments, housing tube 200 may be fixed to housing tube platform 150, e.g., by an adhesive or by any suitable fixation means. Illustratively, a portion of housing tube 200 may be disposed within optic fiber distal guide 165, e.g., housing tube proximal end 202 may be disposed within optic fiber distal guide 165. In one or more embodiments, a portion of housing tube 200 may be fixed within optic fiber distal guide 165, e.g., by an adhesive or by any suitable fixation means.

Illustratively, optic fiber 250 may be disposed within inner bore 160, inner bore distal chamber 162, optic fiber proximal guide 163, optic fiber distal guide 165, and housing tube 200. In one or more embodiments, optic fiber 250 may be disposed within housing tube 200 wherein optic fiber distal end 251 is adjacent to housing tube distal end 201. Illustratively, a portion of optic fiber 250 may be fixed to an inner portion of housing tube 200, e.g., by an adhesive or by any suitable fixation means.

Illustratively, a portion of wire 340 may comprise a preformed curve 345. In one or more embodiments, a portion of wire 340 may comprise a shape memory material, e.g., Nitinol. Illustratively, pre-formed curve 345 may comprise a shape memory material, e.g., Nitinol. In one or more embodiments, wire 340 may be disposed within wire housing 164, optic fiber distal guide 165, and housing tube 200. Illustratively, actuation mechanism 310 may be housed within actuation mechanism housing 135. In one or more embodiments, a portion of actuation mechanism 310 may be disposed within wire housing 164. Illustratively, actuation mechanism 310 may be configured to fix a portion of wire 340, e.g., wire proximal end 342, in a position relative to actuation ring 130. In one or more embodiments, actuation mechanism 310 may comprise a set screw configured to fix wire 340 in a position relative to actuation ring 130, e.g., by a press fit or any other suitable fixation means. Illustratively, a portion of wire 340, e.g., wire proximal end 342, may be fixed to actuation mechanism 310, e.g., by an adhesive or any other suitable fixation means. Wire 340 may be manufactured from any suitable material, e.g., polymers, metals, metal alloys, etc., or from any combination of suitable materials.

In one or more embodiments, a compression of actuation structure 120 may be configured to actuate actuation ring 130, e.g., away from handle proximal end 102 and towards handle distal end 101. Illustratively, a compression of actuation structure 120 may be configured to actuate actuation mechanism 310 along actuation mechanism guide 145, e.g., away from handle proximal end 102 and towards handle distal end 101. In one or more embodiments, a compression of actuation structure 120 may be configured to extend wire 340 relative to housing tube 200. Illustratively, an extension of wire 340 relative to housing tube 200 may be configured to extend a portion of wire 340, e.g., pre-formed curve 345, within housing tube 200. In one or more embodiments, a compression of actuation structure 120 may be configured to actuate preformed curve 345 within housing tube 200, e.g., away from housing tube proximal end 202 and towards housing tube distal end 201. Illustratively, a compression of actuation structure 120 may be configured to extend pre-formed curve 345 within housing tube 200, e.g., away from housing tube proximal end 202 and towards first housing tube portion 220.

In one or more embodiments, a portion of housing tube 200 may be configured to generally straighten pre-formed curve 345. Illustratively, an actuation of pre-formed curve 345 out of a portion of housing tube 200 configured to generally straighten pre-formed curve 345 may be configured to cause housing tube 200 to gradually curve. In one or more embodiments, an actuation of pre-formed curve 345 into a portion of housing tube 200, e.g., first housing tube portion 220, may be configured to cause housing tube 200 to gradually curve. For example, as pre-formed curve 345 is actuated out from a portion of housing tube 200 and into first housing tube portion 220, one or more properties, e.g., a stiffness, of first housing tube portion 220 may be configured to allow pre-formed curve 345 to gradually curve. Illustratively, a compression of actuation structure 120 may be configured to gradually curve housing tube 200. In one or more embodiments, a gradual curving of housing tube 200 may be configured to gradually curve optic fiber 250. Illustratively, a compression of actuation structure 120 may be configured to gradually curve optic fiber 250.

In one or more embodiments, a decompression of actuation structure 120 may be configured to actuate actuation ring 130, e.g., away from handle distal end 101 and towards handle proximal end 102. Illustratively, a decompression of actuation structure 120 may be configured to actuate actuation mechanism 310 along actuation mechanism guide 145, e.g., away from handle distal end 101 and towards handle proximal end 102. In one or more embodiments, a decompression of actuation structure 120 may be configured to retract wire 340 relative to housing tube 200. Illustratively, a retraction of wire 340 relative to housing tube 200 may be configured to retract a portion of wire 340, e.g., pre-formed curve 345, within housing tube 200. In one or more embodiments, a decompression of actuation structure 120 may be configured to actuate pre-formed curve 345 within housing tube 200, e.g., away from housing tube distal end 201 and towards housing tube proximal end 202. Illustratively, a decompression of actuation structure 120 may be configured to retract pre-formed curve 345 within housing tube 200, e.g., towards housing tube proximal end 202 and away from first housing tube portion 220.

In one or more embodiments, a portion of housing tube 200 may be configured to generally straighten pre-formed curve 345. Illustratively, an actuation of pre-formed curve 345 into a portion of housing tube 200 configured to generally straighten pre-formed curve 345 may be configured to cause housing tube 200 to gradually straighten. In one or more embodiments, an actuation of pre-formed curve 345 out from a portion of housing tube 200, e.g., first housing tube portion 220, may be configured to cause housing tube 200 to gradually straighten. For example, as pre-formed curve 345 is actuated into a portion of housing tube 200 and out from first housing tube portion 220, one or more properties, e.g., a stiffness, of the housing tube 200 portion may be configured to cause pre-formed curve 345 to gradually straighten. Illustratively, a decompression of actuation structure 120 may be configured to gradually straighten housing tube 200. In one or more embodiments, a gradual straightening of housing tube 200 may be configured to gradually straighten optic fiber 250. Illustratively, a decompression of actuation structure 120 may be configured to gradually straighten optic fiber 250.

Figure 4A:
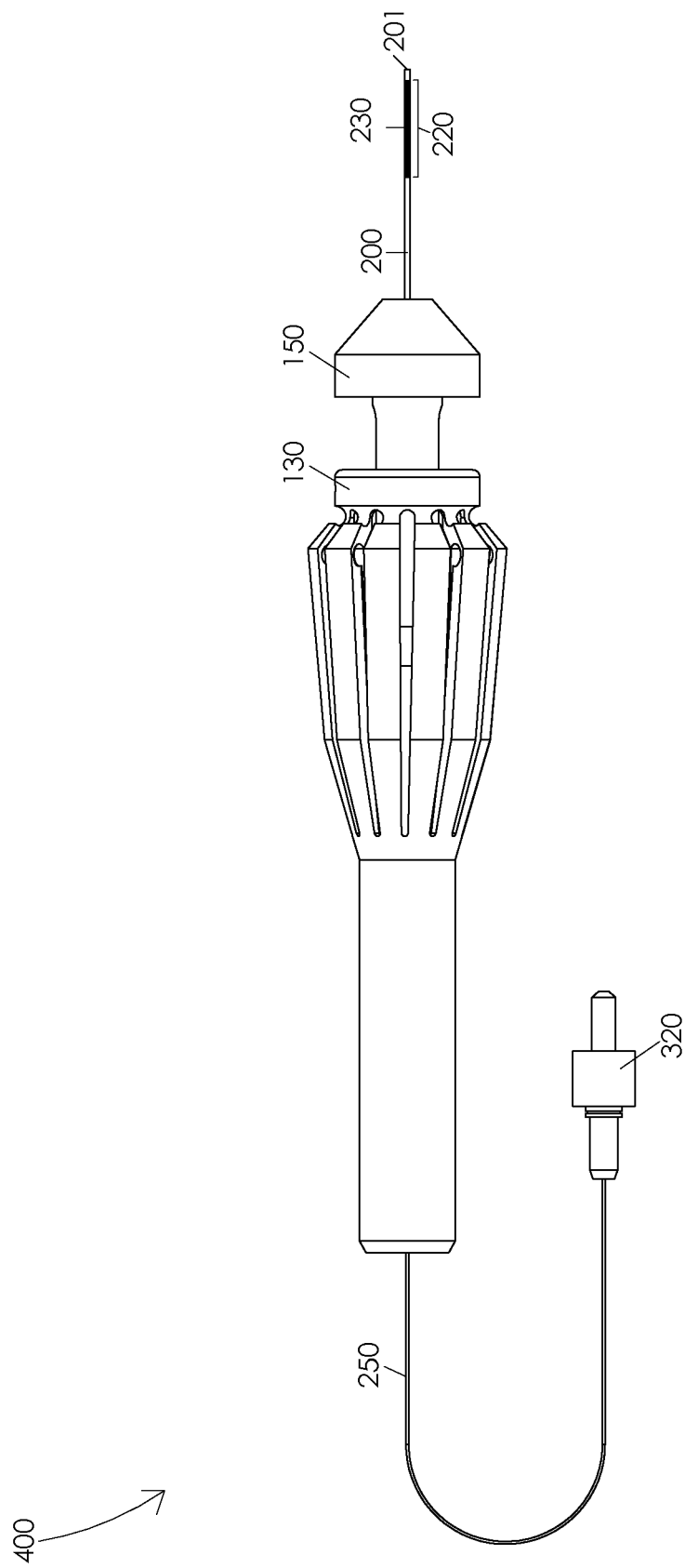
FIGS. 4A, 4B, 4C, 4D, and 4E illustrate a gradual curving of an optic fiber.

FIGS. 4A, 4B, 4C, 4D, and 4E illustrate a gradual curving of an optic fiber 250. FIG. 4A illustrates a straight optic fiber 400. In one or more embodiments, optic fiber 250 may comprise a straight optic fiber 400, e.g., when actuation ring 130 is fully retracted relative to handle base 110. Illustratively, optic fiber 250 may comprise a straight optic fiber 400, e.g., when wire 340 is fully refracted relative to housing tube 200. In one or more embodiments, optic fiber 250 may comprise a straight optic fiber 400, e.g., when actuation structure 120 is fully decompressed. Illustratively, a line tangent to optic fiber distal end 251 may be parallel to a line tangent to housing tube proximal end 202, e.g., when optic fiber 250 comprises a straight optic fiber 400.

Figure 4B:
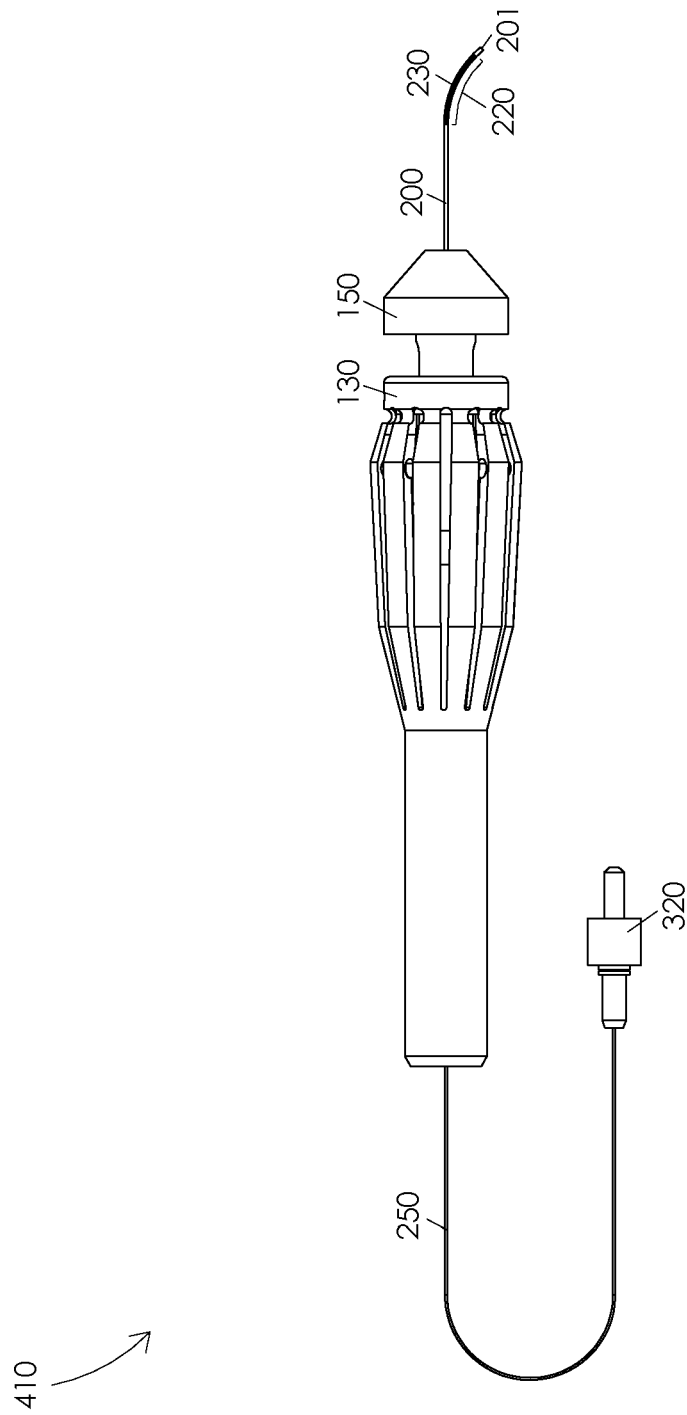

FIG. 4B illustrates an optic fiber in a first curved position 410. In one or more embodiments, a compression of actuation structure 120 may be configured to gradually curve optic fiber 250 from a straight optic fiber 400 to an optic fiber in a first curved position 410. Illustratively, a compression of actuation structure 120 may be configured to gradually extend wire 340 relative to housing tube 200. In one or more embodiments, an extension of wire 340 relative to housing tube 200 may be configured to actuate a portion of pre-formed curve 345 out from a portion of housing tube 200, e.g., a portion of housing tube 200 configured to generally straighten pre-formed curve 345. Illustratively, an extension of wire 340 relative to housing tube 200 may be configured to actuate a portion of pre-formed curve 345 into a portion of housing tube 200, e.g., first housing tube portion 220. In one or more embodiments, a compression of actuation structure 120 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from a straight optic fiber 400 to an optic fiber in a first curved position 410. Illustratively, a line tangent to optic fiber distal end 251 may intersect a line tangent to housing tube proximal end 202 at a first angle, e.g., when optic fiber 250 comprises an optic fiber in a first curved position 410. In one or more embodiments, the first angle may comprise any angle greater than zero degrees. For example, the first angle may comprise a 45 degree angle.

Figure 4C:
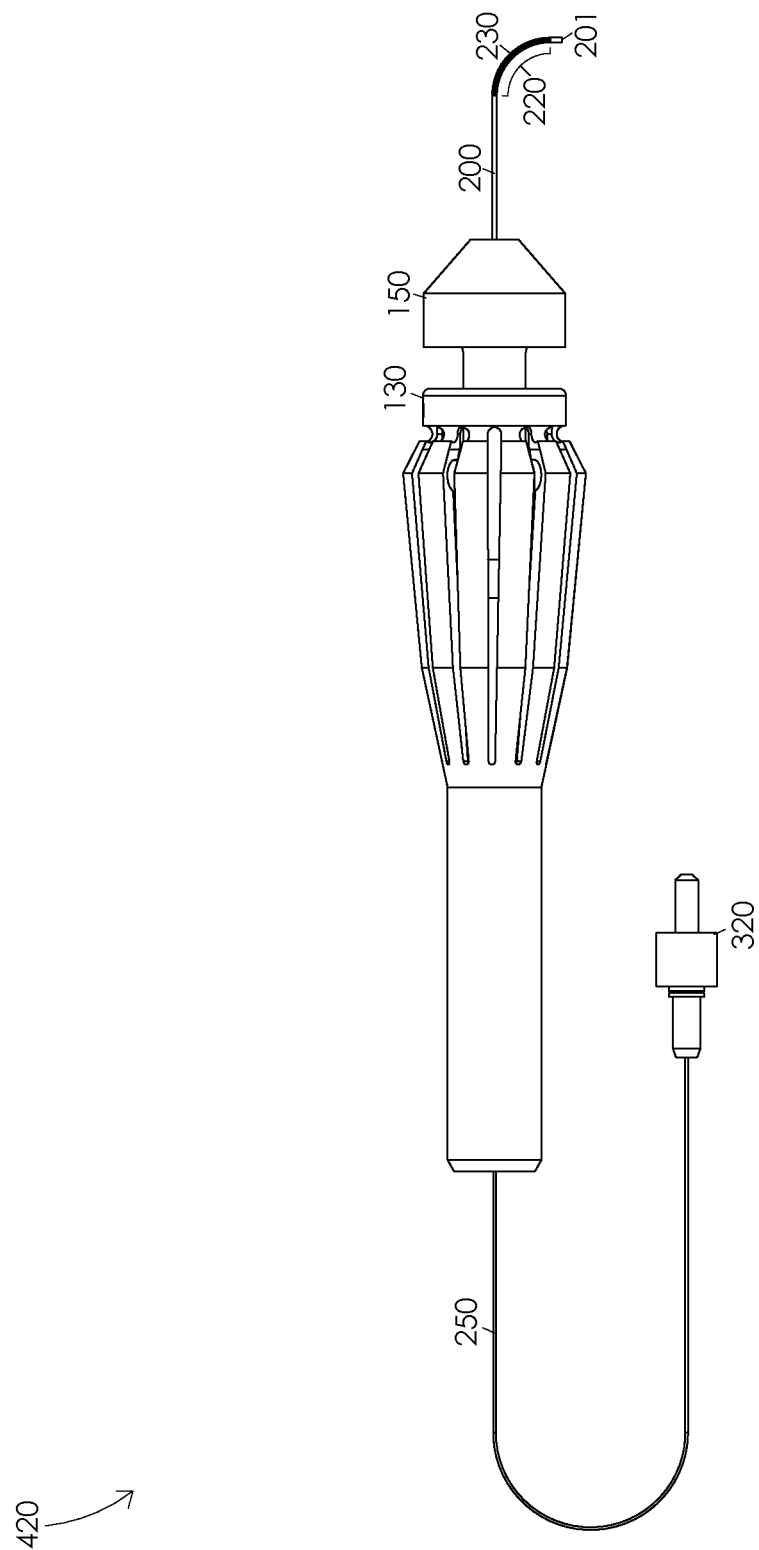

FIG. 4C illustrates an optic fiber in a second curved position 420. In one or more embodiments, a compression of actuation structure 120 may be configured to gradually curve optic fiber 250 from an optic fiber in a first curved position 410 to an optic fiber in a second curved position 420. Illustratively, a compression of actuation structure 120 may be configured to gradually extend wire 340 relative to housing tube 200. In one or more embodiments, an extension of wire 340 relative to housing tube 200 may be configured to actuate a portion of pre-formed curve 345 out from a portion of housing tube 200, e.g., a portion of housing tube 200 configured to generally straighten pre-formed curve 345. Illustratively, an extension of wire 340 relative to housing tube 200 may be configured to actuate a portion of pre-formed curve 345 into a portion of housing tube 200, e.g., first housing tube portion 220. In one or more embodiments, a compression of actuation structure 120 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from an optic fiber in a first curved position 410 to an optic fiber in a second curved position 420. Illustratively, a line tangent to optic fiber distal end 251 may intersect a line tangent to housing tube proximal end 202 at a second angle, e.g., when optic fiber 250 comprises an optic fiber in a second curved position 420. In one or more embodiments, the second angle may comprise any angle greater than the first angle. For example, the second angle may comprise a 90 degree angle.

Figure 4D:
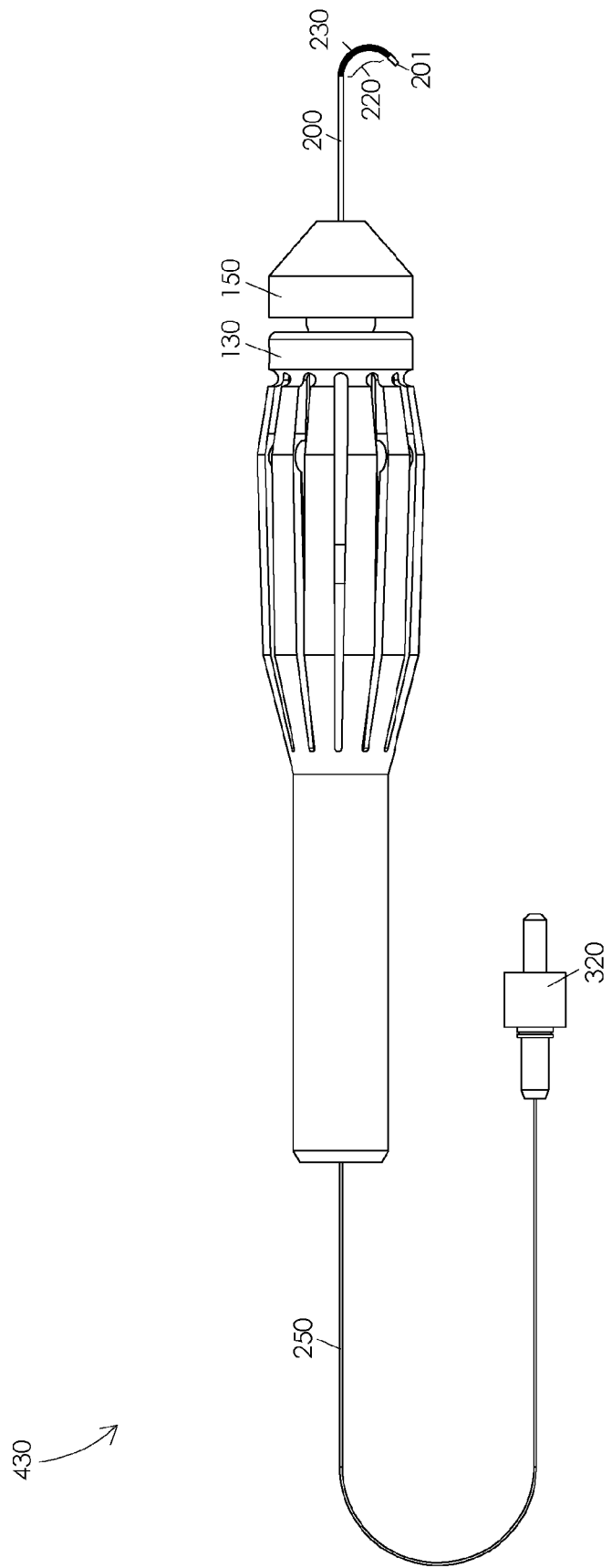

FIG. 4D illustrates an optic fiber in a third curved position 430. In one or more embodiments, a compression of actuation structure 120 may be configured to gradually curve optic fiber 250 from an optic fiber in a second curved position 420 to an optic fiber in a third curved position 430. Illustratively, a compression of actuation structure 120 may be configured to gradually extend wire 340 relative to housing tube 200. In one or more embodiments, an extension of wire 340 relative to housing tube 200 may be configured to actuate a portion of pre-formed curve 345 out from a portion of housing tube 200, e.g., a portion of housing tube 200 configured to generally straighten pre-formed curve 345. Illustratively, an extension of wire 340 relative to housing tube 200 may be configured to actuate a portion of pre-formed curve 345 into a portion of housing tube 200, e.g., first housing tube portion 220. In one or more embodiments, a compression of actuation structure 120 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from an optic fiber in a second curved position 420 to an optic fiber in a third curved position 430. Illustratively, a line tangent to optic fiber distal end 251 may intersect a line tangent to housing tube proximal end 202 at a third angle, e.g., when optic fiber 250 comprises an optic fiber in a third curved position 430. In one or more embodiments, the third angle may comprise any angle greater than the second angle. For example, the third angle may comprise a 135 degree angle.

Figure 4E:
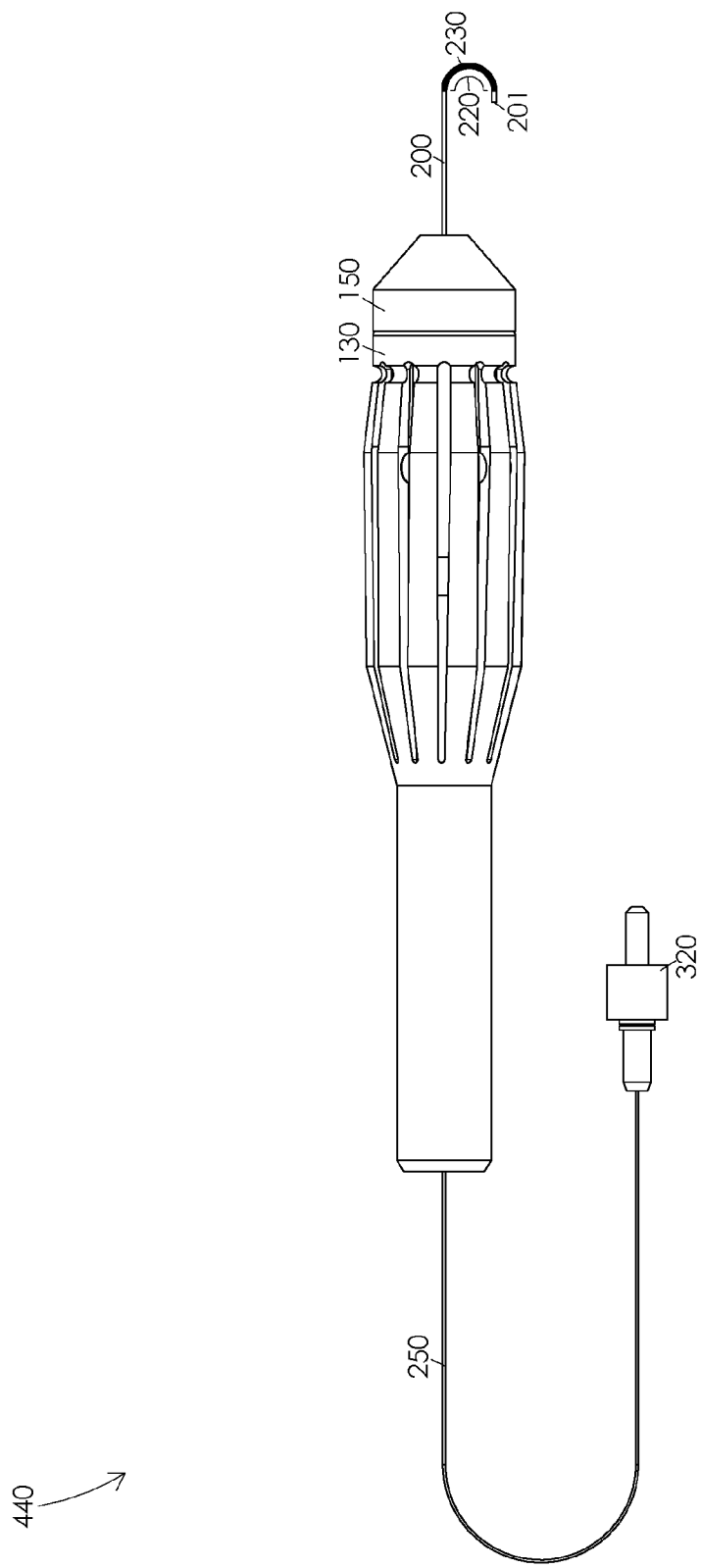

FIG. 4E illustrates an optic fiber in a fourth curved position 440. In one or more embodiments, a compression of actuation structure 120 may be configured to gradually curve optic fiber 250 from an optic fiber in a third curved position 430 to an optic fiber in a fourth curved position 440. Illustratively, a compression of actuation structure 120 may be configured to gradually extend wire 340 relative to housing tube 200. In one or more embodiments, an extension of wire 340 relative to housing tube 200 may be configured to actuate a portion of pre-formed curve 345 out from a portion of housing tube 200, e.g., a portion of housing tube 200 configured to generally straighten pre-formed curve 345. Illustratively, an extension of wire 340 relative to housing tube 200 may be configured to actuate a portion of pre-formed curve 345 into a portion of housing tube 200, e.g., first housing tube portion 220. In one or more embodiments, a compression of actuation structure 120 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from an optic fiber in a third curved position 430 to an optic fiber in a fourth curved position 440. Illustratively, a line tangent to optic fiber distal end 251 may be parallel to a line tangent to housing tube proximal end 202, e.g., when optic fiber 250 comprises an optic fiber in a fourth curved position 440.

In one or more embodiments, one or more properties of a steerable laser probe may be adjusted to attain one or more desired steerable laser probe features. For example, a length that housing tube 200 extends from housing tube platform 150 may be adjusted to vary an amount of compression of actuation structure 120 configured to curve housing tube 200 to a particular curved position. Illustratively, a length of wire 340 may be adjusted to vary an amount of compression of actuation structure 120 configured to curve housing tube 200 to a particular curved position. In one or more embodiments, a stiffness of first housing tube portion 220 or a stiffness of second housing tube portion 230 may be adjusted to vary an amount of compression of actuation structure 120 configured to curve housing tube 200 to a particular curved position. Illustratively, a geometry of pre-formed curve 345 may be adjusted to vary an amount of compression of actuation structure 120 configured to curve housing tube 200 to a particular curved position. In one or more embodiments, a material comprising wire 340 or a material comprising a portion of wire 340, e.g., pre-formed curve 345, may be adjusted to vary an amount of compression of actuation structure 120 configured to curve housing tube 200 to a particular curved position. Illustratively, a material comprising first housing tube portion 220 or a material comprising second housing tube portion 230 may be adjusted to vary an amount of compression of actuation structure 120 configured to curve housing tube 200 to a particular curved position.

In one or more embodiments, a number of apertures in housing tube 200 may be adjusted to vary an amount of compression of actuation structure 120 configured to curve housing tube 200 to a particular curved position. Illustratively, a location of one or more apertures in housing tube 200 may be adjusted to vary an amount of compression of actuation structure 120 configured to curve housing tube 200 to a particular curved position. In one or more embodiments, a geometry of one or more apertures in housing tube 200 may be adjusted to vary an amount of compression of action structure 120 configured to curve housing tube 200 to a particular curved position. Illustratively, a geometry of one or more apertures in housing tube 200 may be uniform, e.g., each aperture of the one or more apertures may have a same geometry. In one or more embodiments, a geometry of one or more apertures in housing tube 200 may be non-uniform, e.g., a first aperture in housing tube 200 may have a first geometry and a second aperture in housing tube 200 may have a second geometry.

Illustratively, a distance that housing tube platform 150 extends from handle proximal end 102 may be adjusted to vary an amount of compression of actuation structure 120 configured to curve housing tube 200 to a particular curved position. In one or more embodiments, a geometry of actuation structure 120 may be adjusted to vary an amount of compression of actuation structure 120 configured to curve housing tube 200 to a particular curved position. Illustratively, at least a portion of optic fiber 250 may be enclosed in an optic fiber sleeve configured to, e.g., protect optic fiber 250, vary a stiffness of optic fiber 250, vary an optical property of optic fiber 250, etc.

Illustratively, a stiffness of first housing tube portion 220 or a stiffness of second housing tube portion 230 may be adjusted to vary a bend radius of housing tube 200. In one or more embodiments, a stiffness of first housing tube portion 220 or a stiffness of second housing tube portion 230 may be adjusted to vary a radius of curvature of housing tube 200, e.g., when housing tube 200 is in a particular curved position. Illustratively, a number of apertures in housing tube 200 may be adjusted to vary a bend radius of housing tube 200. In one or more embodiments, a number of apertures in housing tube 200 may be adjusted to vary a radius of curvature of housing tube 200, e.g., when housing tube 200 is in a particular curved position. Illustratively, a location or a geometry of one or more apertures in housing tube 200 may be adjusted to vary a bend radius of housing tube 200. In one or more embodiments, a location or a geometry of one or more apertures in housing tube 200 may be adjusted to vary a radius of curvature of housing tube 200, e.g., when housing tube 200 is in a particular curved position.

In one or more embodiments, a location of pre-formed curve 345 of wire 340 or a location of first housing tube portion 220 of housing tube 200 may be adjusted to vary one or more steerable laser probe features. Illustratively, a location of pre-formed curve 345 or a location of first housing tube portion 220 may be adjusted wherein a portion of pre-formed curve 345 may be disposed within first housing tube portion 220. In one or more embodiments, a relative location of pre-formed curve 345 and first housing tube portion 220 may be adjusted wherein a compression of actuation structure 120 may be configured to extend a portion of pre-formed curve 345 out from first housing tube portion 220 and into a portion of housing tube 200 configured to generally straighten pre-formed curve 345. Illustratively, a compression of actuation structure 120 may be configured to gradually straighten housing tube 200. In one or more embodiments, a gradual straightening of housing tube 200 may be configured to gradually straighten optic fiber 250.

Illustratively, wire 340 may comprise any suitable structure, e.g., wire 340 may comprise a cable. For example, wire 340 may comprise a cable having a pre-formed curve 345. In one or more embodiments, wire 340 may be replaced with a tube or a portion of wire 340 may comprise an inner bore. For example, wire 340 may be replaced with a tube having a pre-formed curve 345.

Illustratively, a location of pre-formed curve 345 or a location of first housing tube portion 220 may be adjusted wherein a portion of pre-formed curve 345 may be disposed within a portion of housing tube 200 configured to generally straighten pre-formed curve 345. In one or more embodiments, a relative location of pre-formed curve 345 and first housing tube portion 220 may be adjusted wherein a decompression of actuation structure 120 may be configured to retract a portion of pre-formed curve 345 into first housing tube portion 220 and out from a portion of housing tube 200 configured to generally straighten pre-formed curve 345. Illustratively, a decompression of actuation structure 120 may be configured to gradually curve housing tube 200. In one or more embodiments, a gradual curving of housing tube 200 may be configured to gradually curve optic fiber 250.

Figure 5A:
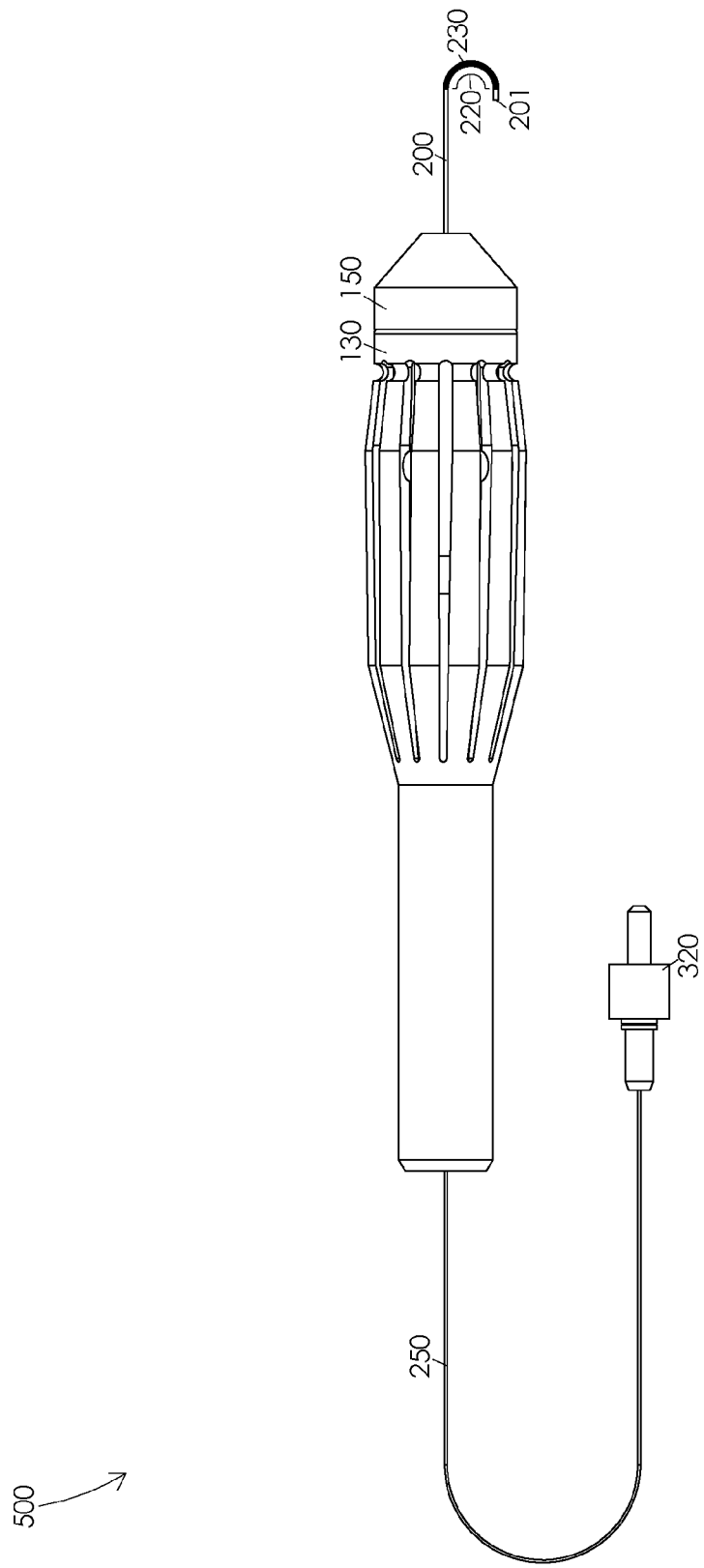
FIGS. 5A, 5B, 5C, 5D, and 5E illustrate a gradual straightening of an optic fiber.

FIGS. 5A, 5B, 5C, 5D, and 5E illustrate a gradual straightening of an optic fiber 250. FIG. 5A illustrates a fully curved optic fiber 500. In one or more embodiments, optic fiber 250 may comprise a fully curved optic fiber 500, e.g., when actuation ring 130 is fully extended relative to handle base 110. Illustratively, optic fiber 250 may comprise a fully curved optic fiber 500, e.g., when wire 340 is fully extended relative to housing tube 200. In one or more embodiments, optic fiber 250 may comprise a fully curved optic fiber 500, e.g., when actuation structure 120 is fully compressed. Illustratively, a line tangent to optic fiber distal end 251 may be parallel to a line tangent to housing tube proxies mal end 202, e.g., when optic fiber 250 comprises a fully curved optic fiber 500.

Figure 5B:
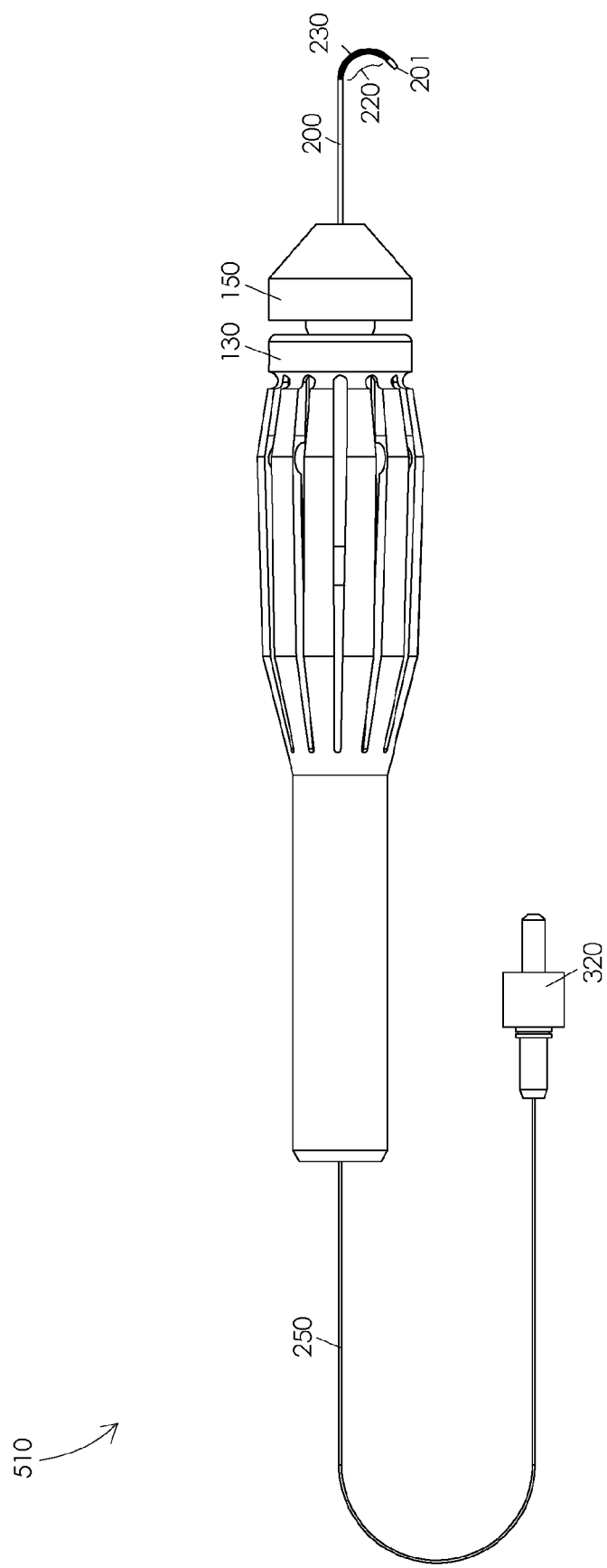

FIG. 5B illustrates an optic fiber in a first partially straightened position 510. In one or more embodiments, a decompression of actuation structure 120 may be configured to gradually straighten optic fiber 250 from a fully curved optic fiber 500 to an optic fiber in a first partially straightened position 510. Illustratively, a decompression of actuation structure 120 may be configured to gradually retract wire 340 relative to housing tube 200. In one or more embodiments, a retraction of wire 340 relative to housing tube 200 may be configured to actuate a portion of pre-formed curve 345 into a portion of housing tube 200, e.g., a portion of housing tube 200 configured to generally straighten pre-formed curve 345. Illustratively, a retraction of wire 340 relative to housing tube 200 may be configured to actuate a portion of pre-formed curve 345 out from a portion of housing tube 200, e.g., first housing tube portion 220. In one or more embodiments, a decompression of actuation structure 120 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from a fully curved optic fiber 500 to an optic fiber in a first partially straightened position 510. Illustratively, a line tangent to optic fiber distal end 251 may intersect a line tangent to housing tube proximal end 202 at a first partially straightened angle, e.g., when optic fiber 250 comprises an optic fiber in a first partially straightened position 510. In one or more embodiments, the first partially straightened angle may comprise any angle less than 180 degrees. For example, the first partially straightened angle may comprise a 135 degree angle.

Figure 5C:
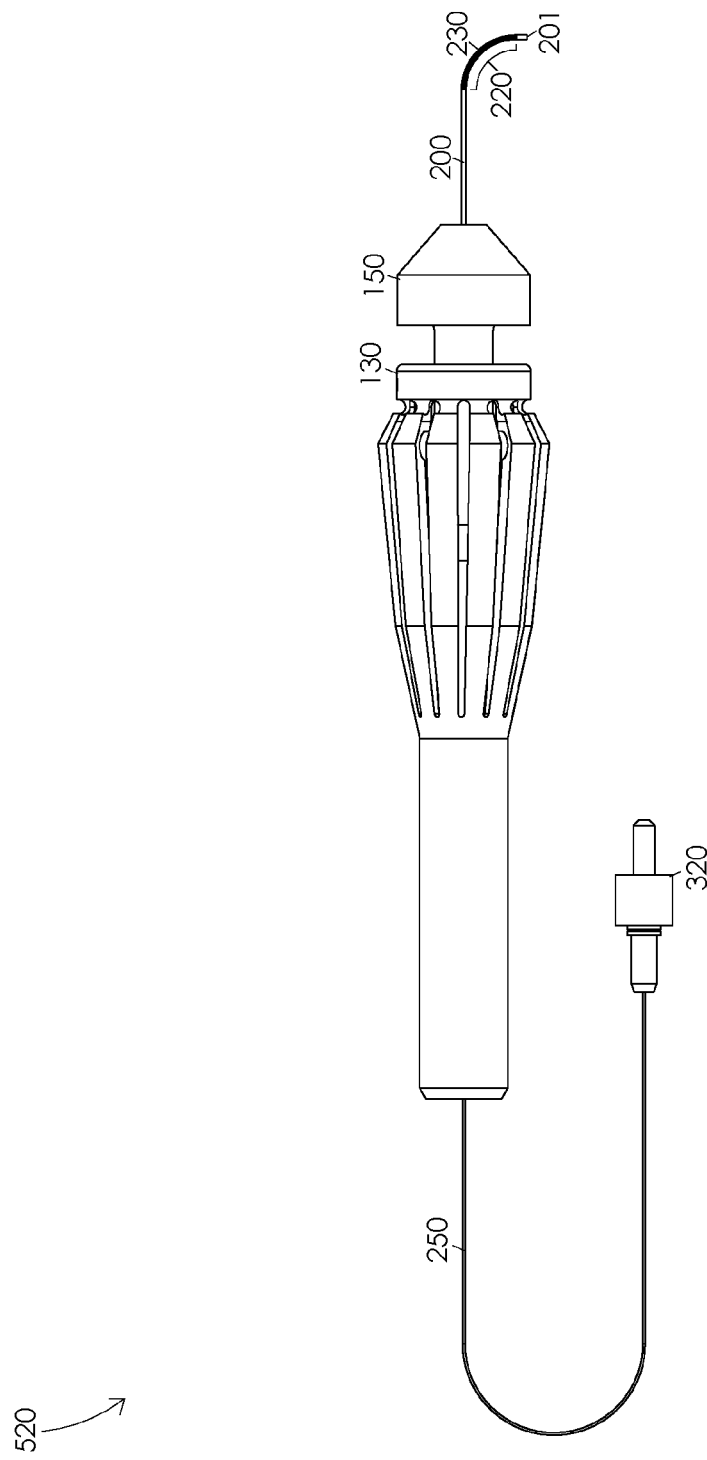

FIG. 5C illustrates an optic fiber in a second partially straightened position 520. In one or more embodiments, a decompression of actuation structure 120 may be configured to gradually straighten optic fiber 250 from an optic fiber in a first partially straightened position 510 to an optic fiber in a second partially straightened position 520. Illustratively, a decompression of actuation structure 120 may be configured to gradually retract wire 340 relative to housing tube 200. In one or more embodiments, a retraction of wire 340 relative to housing tube 200 may be configured to actuate a portion of pre-formed curve 345 into a portion of housing tube 200, e.g., a portion of housing tube 200 configured to generally straighten pre-formed curve 345. Illustratively, a retraction of wire 340 relative to housing tube 200 may be configured to actuate a portion of pre-formed curve 345 out from a portion of housing tube 200, e.g., first housing tube portion 220. In one or more embodiments, a decompression of actuation structure 120 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from an optic fiber in a first partially straightened position 510 to an optic fiber in a second partially straightened position 520. Illustratively, a line tangent to optic fiber distal end 251 may intersect a line tangent to housing tube proximal end 202 at a second partially straightened angle, e.g., when optic fiber 250 comprises an optic fiber in a second partially straightened position 520. In one or more embodiments, the second partially straightened angle may comprise any angle less than the first partially straightened angle. For example, the second partially straightened angle may comprise a 90 degree angle.

Figure 5D:
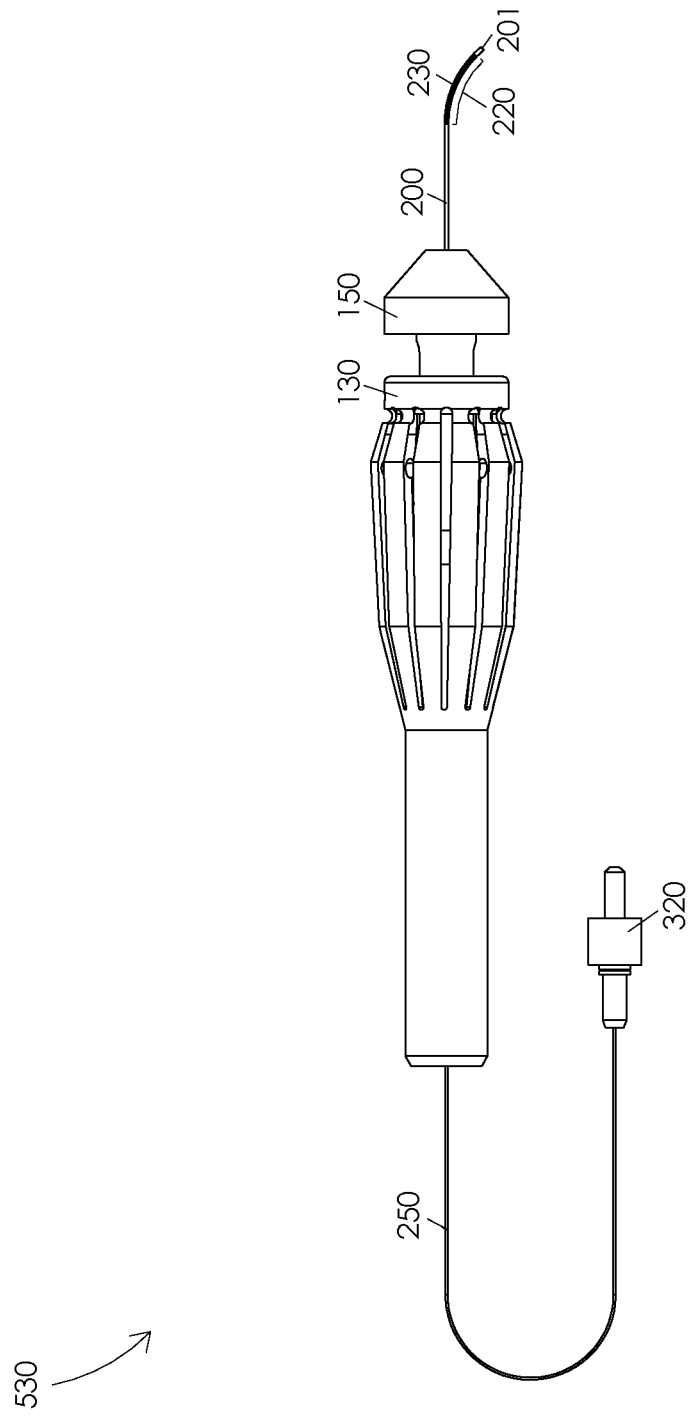

FIG. 5D illustrates an optic fiber in a third partially straightened position 530. In one or more embodiments, a decompression of actuation structure 120 may be configured to gradually straighten optic fiber 250 from an optic fiber in a second partially straightened position 520 to an optic fiber in a third partially straightened position 530. Illustratively, a decompression of actuation structure 120 may be configured to gradually retract wire 340 relative to housing tube 200. In one or more embodiments, a retraction of wire 340 relative to housing tube 200 may be configured to actuate a portion of pre-formed curve 345 into a portion of housing tube 200, e.g., a portion of housing tube 200 configured to generally straighten pre-formed curve 345. Illustratively, a retraction of wire 340 relative to housing tube 200 may be configured to actuate a portion of pre-formed curve 345 out from a portion of housing tube 200, e.g., first housing tube portion 220. In one or more embodiments, a decompression of actuation structure 120 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from an optic fiber in a second partially straightened position 520 to an optic fiber in a third partially straightened position 530. Illustratively, a line tangent to optic fiber distal end 251 may intersect a line tangent to housing tube proximal end 202 at a third partially straightened angle, e.g., when optic fiber 250 comprises an optic fiber in a third partially straightened position 530. In one or more embodiments, the third partially straightened angle may comprise any angle less than the second partially straightened angle. For example, the third partially straightened angle may comprise a 45 degree angle.

Figure 5E:
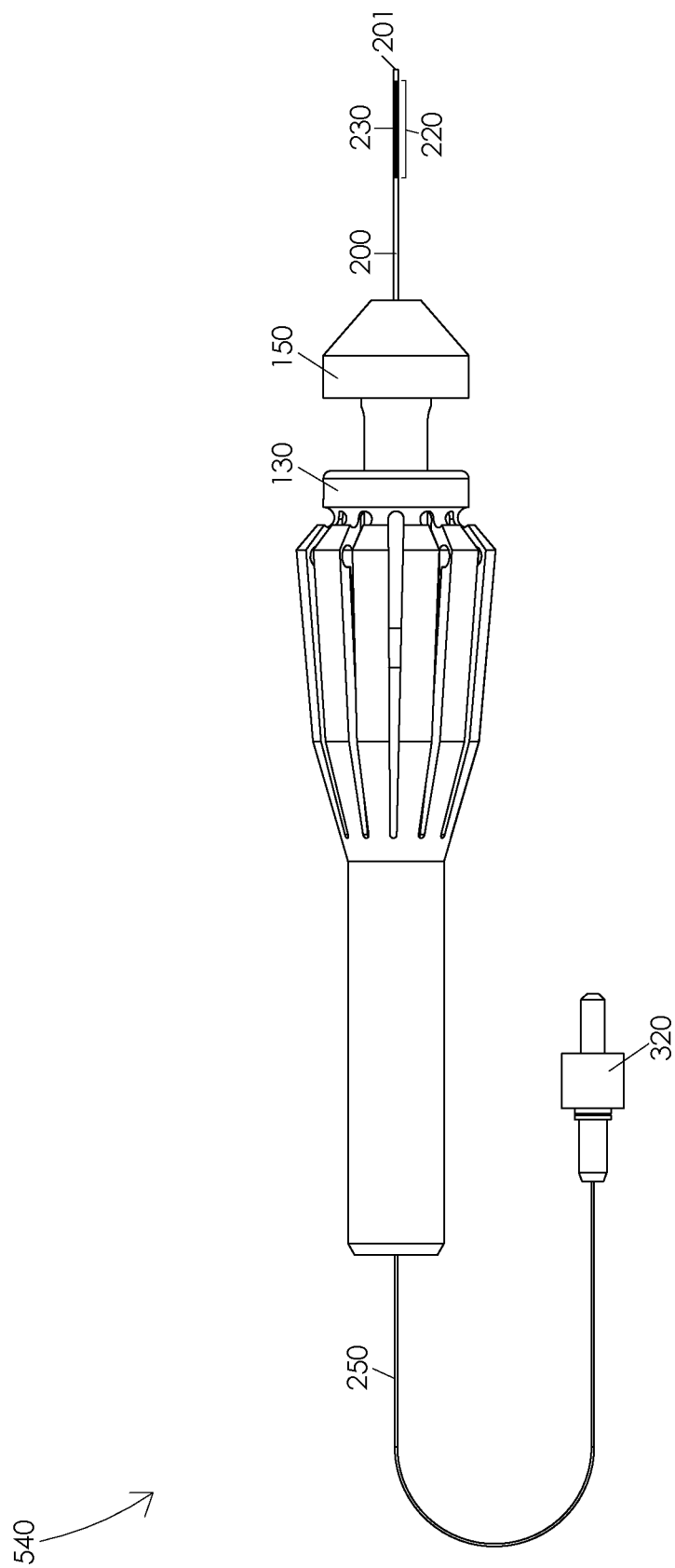

FIG. 5E illustrates an optic fiber in a fully straightened position 540. In one or more embodiments, a decompression of actuation structure 120 may be configured to gradually straighten optic fiber 250 from an optic fiber in a third partially straightened position 530 to an optic fiber in a fully straightened position 540. Illustratively, a decompression of actuation structure 120 may be configured to gradually retract wire 340 relative to housing tube 200. In one or more embodiments, a retraction of wire 340 relative to housing tube 200 may be configured to actuate a portion of pre-formed curve 345 into a portion of housing tube 200, e.g., a portion of housing tube 200 configured to generally straighten pre-formed curve 345. Illustratively, a retraction of wire 340 relative to housing tube 200 may be configured to actuate a portion of pre-formed curve 345 out from a portion of housing tube 200, e.g., first housing tube portion 220. In one or more embodiments, a decompression of actuation structure 120 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from an optic fiber in a third partially straightened position 530 to an optic fiber in a fully straightened position 540. Illustratively, a line tangent to optic fiber distal end 251 may be parallel to a line tangent to housing tube proximal end 202, e.g., when optic fiber 250 comprises an optic fiber in a fully straightened position 540.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 100 to orient housing tube 200 in an orientation configured to cause a curvature of housing tube 200 within the particular transverse plane of the inner eye and varying an amount of compression of actuation structure 120. Illustratively, a surgeon may aim optic fiber distal end 251 at any target within a particular sagittal plane of the inner eye by, e.g., rotating handle 100 to orient housing tube 200 in an orientation configured to cause a curvature of housing tube 200 within the particular sagittal plane of the inner eye and varying an amount of compression of actuation structure 120. In one or more embodiments, a surgeon may aim optic fiber distal end 251 at any target within a particular frontal plane of the inner eye by, e.g., varying an amount of compression of actuation structure 120 to orient a line tangent to optic fiber distal end 251 wherein the line tangent to optic fiber distal end 251 is within the particular frontal plane of the inner eye and rotating handle 100. Illustratively, a surgeon may aim optic fiber distal end 251 at any target located outside of the particular transverse plane, the particular sagittal plane, and the particular frontal plane of the inner eye, e.g., by varying a rotational orientation of handle 100 and varying an amount of compression of actuation structure 120. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

FIGS. 6A and 6B are schematic diagrams illustrating a handle 600. FIG. 6A illustrates a top view of handle 600. In one or more embodiments, handle 600 may comprise a handle distal end 601, a handle proximal end 602, a handle base 610, an actuation structure 620, a housing tube platform 630, and an actuation platform 640. Illustratively, actuation platform 640 may comprise an actuation platform distal end 641 and an actuation platform proximal end 642. In one or more embodiments, actuation structure 620 may comprise a plurality of actuation arms 625. Illustratively, each actuation arm 625 may comprise at least one extension mechanism 626. In one or more embodiments, each actuation arm 625 may comprise an inverted actuation joint 627.

Illustratively, actuation structure 620 may be compressed, e.g., by an application of a compressive force to actuation structure 620. In one or more embodiments, actuation structure 620 may be compressed by an application of one or more compressive forces located at one or more locations around an outer perimeter of actuation structure 620. Illustratively, the one or more locations may comprise any of a plurality of locations around the outer perimeter of actuation structure 620. For example, a surgeon may compress actuation structure 620, e.g., by squeezing actuation structure 620. Illustratively, the surgeon may compress actuation structure 620 by squeezing actuation structure 620 at any particular location of a plurality of locations around an outer perimeter of actuation structure 620. For example, a surgeon may rotate handle 600 and compress actuation structure 620 from any rotational position of a plurality of rotational positions of handle 600.

In one or more embodiments, actuation structure 620 may be compressed by an application of a compressive force to any one or more of the plurality of actuation arms 625. Illustratively, each actuation arm 625 may be configured to actuate independently. In one or more embodiments, each actuation arm 625 may be connected to one or more of the plurality of actuation arms 625 wherein an actuation of a particular actuation arm 625 may be configured to actuate every actuation arm 625 of the plurality of actuation arms 625. In one or more embodiments, a compression of actuation structure 620, e.g., due to an application of a compressive force to a particular actuation arm 625, may be configured to actuate the particular actuation arm 625. Illustratively, an actuation of the particular actuation arm 625 may be configured to actuate every actuation arm 625 of the plurality of actuation arms 625. In one or more embodiments, an application of a compressive force to a particular actuation arm 625 may be configured to extend at least one extension mechanism 626 of the particular actuation arm 625.

Illustratively, an application of a compressive force to a particular actuation arm 625 may be configured to retract actuation platform 640 relative to handle base 610. In one or more embodiments, as a particular actuation arm 625 is compressed, e.g., due to an application of a compressive force to the particular actuation arm 625, an inverted actuation joint 627 of the particular actuation arm 625 may be configured to gradually retract actuation platform 640 relative to handle base 610. Illustratively, inverted actuation joint 627 may be configured to retract actuation platform 640 relative to handle base 610, e.g., by transferring a compressive force applied to actuation structure 620 to a force applied to actuation platform distal end 641. For example, when a compressive force is applied to a particular actuation arm 625, e.g., and the particular actuation arm 625 is extended by at least one extension mechanism 626 of the particular actuation arm 625, an inverted actuation joint 627 of the particular actuation arm 625 may be configured to retract actuation platform 640 relative to handle base 610.

FIG. 6B illustrates a cross-sectional view of handle 600. In one or more embodiments, handle 600 may comprise an inner bore 660, an inner bore proximal taper 661, an actuation mechanism housing 645, an inner bore distal chamber 662, a wire housing 663, and a wire guide 665. Handle 600 may be manufactured from any suitable material, e.g., polymers, metals, metal alloys, etc., or from any combination of suitable materials.

FIG. 7 is a schematic diagram illustrating an exploded view of a steerable laser probe assembly 700. In one or more embodiments, a steerable laser probe assembly 700 may comprise a housing tube 200 having a housing tube distal end 201, a housing tube proximal end 202, a first housing tube portion 220, and a second housing tube portion 230; a wire 340 having a wire distal end 341, a wire proximal end 342, and a pre-formed curve 345; an optic fiber 250 having an optic fiber distal end 251 and an optic fiber proximal end 252; a light source interface 320; and an actuation mechanism 710. Illustratively, light source interface 320 may be configured to interface with optic fiber 250, e.g., at optic fiber proximal end 252. In one or more embodiments, light source interface 320 may comprise a standard light source connector, e.g., an SMA connector.

Illustratively, housing tube 200 may be fixed to housing tube platform 630, e.g., housing tube proximal end 202 may be fixed to housing tube platform 630. In one or more embodiments, housing tube 200 may be fixed to housing tube platform 630, e.g., by an adhesive or by any suitable fixation means. Illustratively, a portion of housing tube 200 may be disposed within wire guide 665, e.g., housing tube proximal end 202 may be disposed within wire guide 665. In one or more embodiments, housing tube proximal end 202 may be fixed within wire guide 665, e.g., by an adhesive or by any suitable fixation means.

Illustratively, optic fiber 250 may be disposed within inner bore 660, inner bore distal chamber 662, wire housing 663, wire guide 665, and housing tube 200. In one or more embodiments, optic fiber 250 may be disposed within housing tube 200 wherein optic fiber distal end 251 is adjacent to housing tube distal end 201. Illustratively, a portion of optic fiber 250 may be fixed to an inner portion of housing tube 200, e.g., by an adhesive or by any suitable fixation means.

Illustratively, a portion of wire 340 may comprise a preformed curve 345. In one or more embodiments, a portion of wire 340 may comprise a shape memory material, e.g., Nitinol. Illustratively, pre-formed curve 345 may comprise a shape memory material, e.g., Nitinol. In one or more embodiments, wire 340 may be disposed within wire housing 663, wire guide 665, and housing tube 200. Illustratively, actuation mechanism 710 may be disposed within actuation mechanism housing 645. In one or more embodiments, actuation mechanism 710 may be configured to fix a portion of wire 340, e.g., wire proximal end 342, in a position relative to actuation platform 640. Illustratively, a portion of actuation mechanism 710 may be disposed within wire housing 663. In one or more embodiments, actuation mechanism 710 may comprise a set screw configured to firmly fix wire 340 in a position relative to actuation platform 640, e.g., by a press fit or any other suitable fixation means. Illustratively, a portion of wire 340, e.g., wire proximal end 342, may be fixed to actuation mechanism 710, e.g., by an adhesive or by any suitable fixation means. Wire 340 may be manufactured from any suitable material, e.g., polymers, metals, metal alloys, etc., or from any combination of suitable materials.

In one or more embodiments, a compression of actuation structure 620 may be configured to actuate actuation platform 640, e.g., towards handle proximal end 602 and away from handle distal end 601. Illustratively, a compression of actuation structure 620 may be configured to retract actuation platform 640 relative to housing tube 200. In one or more embodiments, a compression of actuation structure 620 may be configured to retract wire 340 relative to housing tube 200. Illustratively, a retraction of wire 340 relative to housing tube 200 may be configured to retract a portion of wire 340, e.g., pre-formed curve 345, within housing tube 200. In one or more embodiments, a compression of actuation structure 620 may be configured to actuate pre-formed curve 345 within housing tube 200, e.g., away from housing tube distal end 201 and towards housing tube proximal end 202. Illustratively, a compression of actuation structure 620 may be configured to retract pre-formed curve 345 within housing tube 200, e.g., away from housing tube distal end 201 and towards first housing tube portion 220.

In one or more embodiments, a portion of housing tube 200 may be configured to generally straighten pre-formed curve 345. Illustratively, an actuation of pre-formed curve 345 out of a portion of housing tube 200 configured to generally straighten pre-formed curve 345 may be configured to cause housing tube 200 to gradually curve. In one or more embodiments, an actuation of pre-formed curve 345 into a portion of housing tube 200, e.g., first housing tube portion 220, may be configured to cause housing tube 200 to gradually curve. For example, as pre-formed curve 345 is actuated out from a portion of housing tube 200 and into first housing tube portion 220, one or more properties, e.g., a stiffness, of first housing tube portion 220 may be configured to allow pre-formed curve 345 to gradually curve. Illustratively, a compression of actuation structure 620 may be configured to gradually curve housing tube 200. In one or more embodiments, a gradual curving of housing tube 200 may be configured to gradually curve optic fiber 250. Illustratively, a compression of actuation structure 620 may be configured to gradually curve optic fiber 250.

In one or more embodiments, a decompression of actuation structure 620 may be configured to actuate actuation platform 640, e.g., towards handle distal end 601 and away from handle proximal end 602. Illustratively, a decompression of actuation structure 620 may be configured to extend actuation platform 640 relative to housing tube 200. In one or more embodiments, a decompression of actuation structure 620 may be configured to extend wire 340 relative to housing tube 200. Illustratively, an extension of wire 340 relative to housing tube 200 may be configured to extend a portion of wire 340, e.g., pre-formed curve 345, within housing tube 200. In one or more embodiments, a decompression of actuation structure 620 may be configured to actuate pre-formed curve 345 within housing tube 200, e.g., away from housing tube proximal end 202 and towards housing tube distal end 201. Illustratively, a decompression of actuation structure 620 may be configured to extend pre-formed curve 345 within housing tube 200, e.g., towards housing tube distal end 201 and away from first housing tube portion 220.

In one or more embodiments, a portion of housing tube 200 may be configured to generally straighten pre-formed curve 345. Illustratively, an actuation of pre-formed curve 345 into a portion of housing tube 200 configured to generally straighten pre-formed curve 345 may be configured to cause housing tube 200 to gradually straighten. In one or more embodiments, an actuation of pre-formed curve 345 out from a portion of housing tube 200, e.g., first housing tube portion 220, may be configured to cause housing tube 200 to gradually straighten. For example, as pre-formed curve 345 is actuated into a portion of housing tube 200 and out from first housing tube portion 220, one or more properties, e.g., a stiffness, of the housing tube 200 portion may be configured to cause pre-formed curve 345 to gradually straighten. Illustratively, a decompression of actuation structure 620 may be configured to gradually straighten housing tube 200. In one or more embodiments, a gradual straightening of housing tube 200 may be configured to gradually straighten optic fiber 250. Illustratively, a decompression of actuation structure 620 may be configured to gradually straighten optic fiber 250.

Figure 8A:
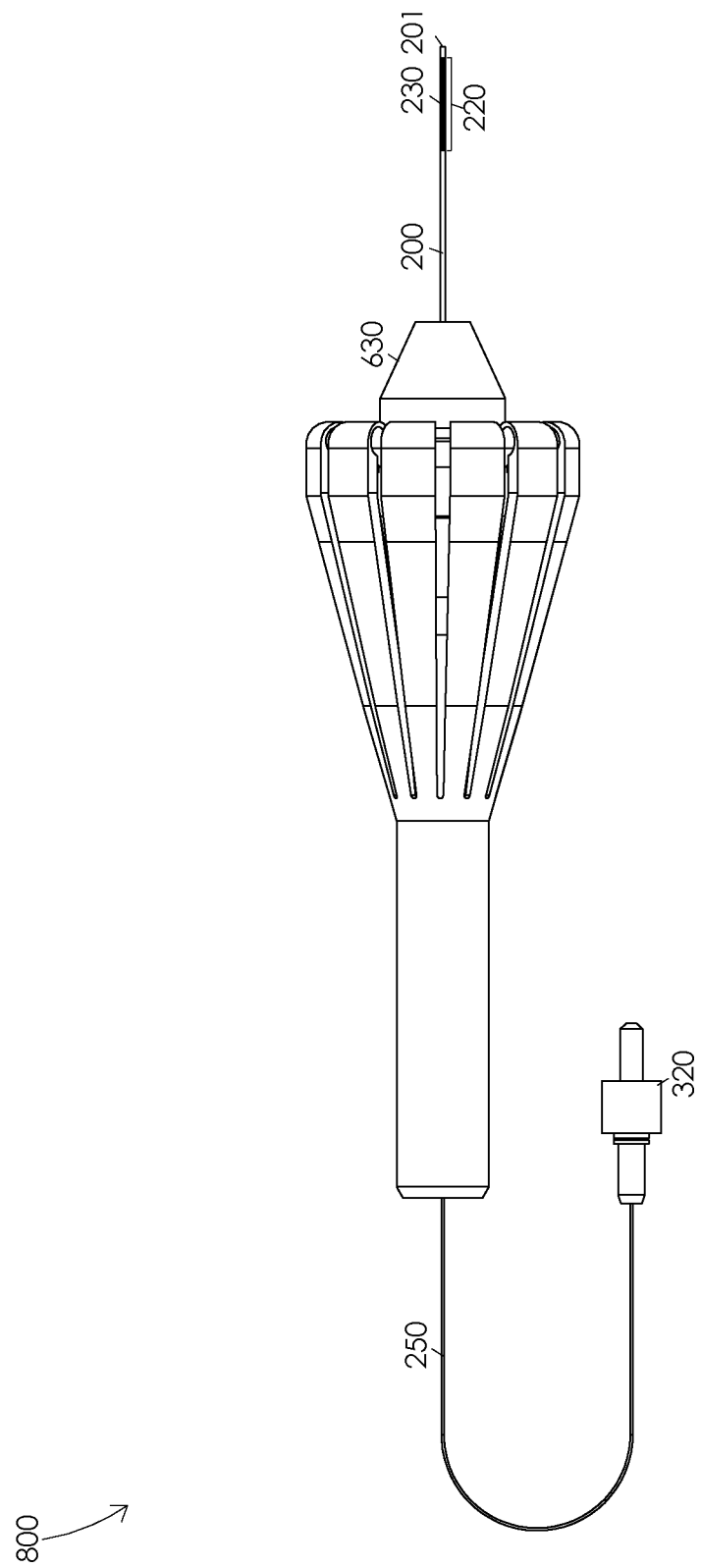
FIGS. 8A, 8B, 8C, 8D, and 8E illustrate a gradual curving of an optic fiber.

FIGS. 8A, 8B, 8C, 8D, and 8E illustrate a gradual curving of an optic fiber 250. FIG. 8A illustrates a straight optic fiber 800. In one or more embodiments, optic fiber 250 may comprise a straight optic fiber 800, e.g., when actuation platform 640 is fully extended relative to handle base 610. Illustratively, optic fiber 250 may comprise a straight optic fiber 800, e.g., when wire 340 is fully extended relative to housing tube 200. In one or more embodiments, optic fiber 250 may comprise a straight optic fiber 800, e.g., when actuation structure 620 is fully decompressed. Illustratively, a line tangent to optic fiber distal end 251 may be parallel to a line tangent to housing tube proximal end 202, e.g., when optic fiber 250 comprises a straight optic fiber 800.

Figure 8B:
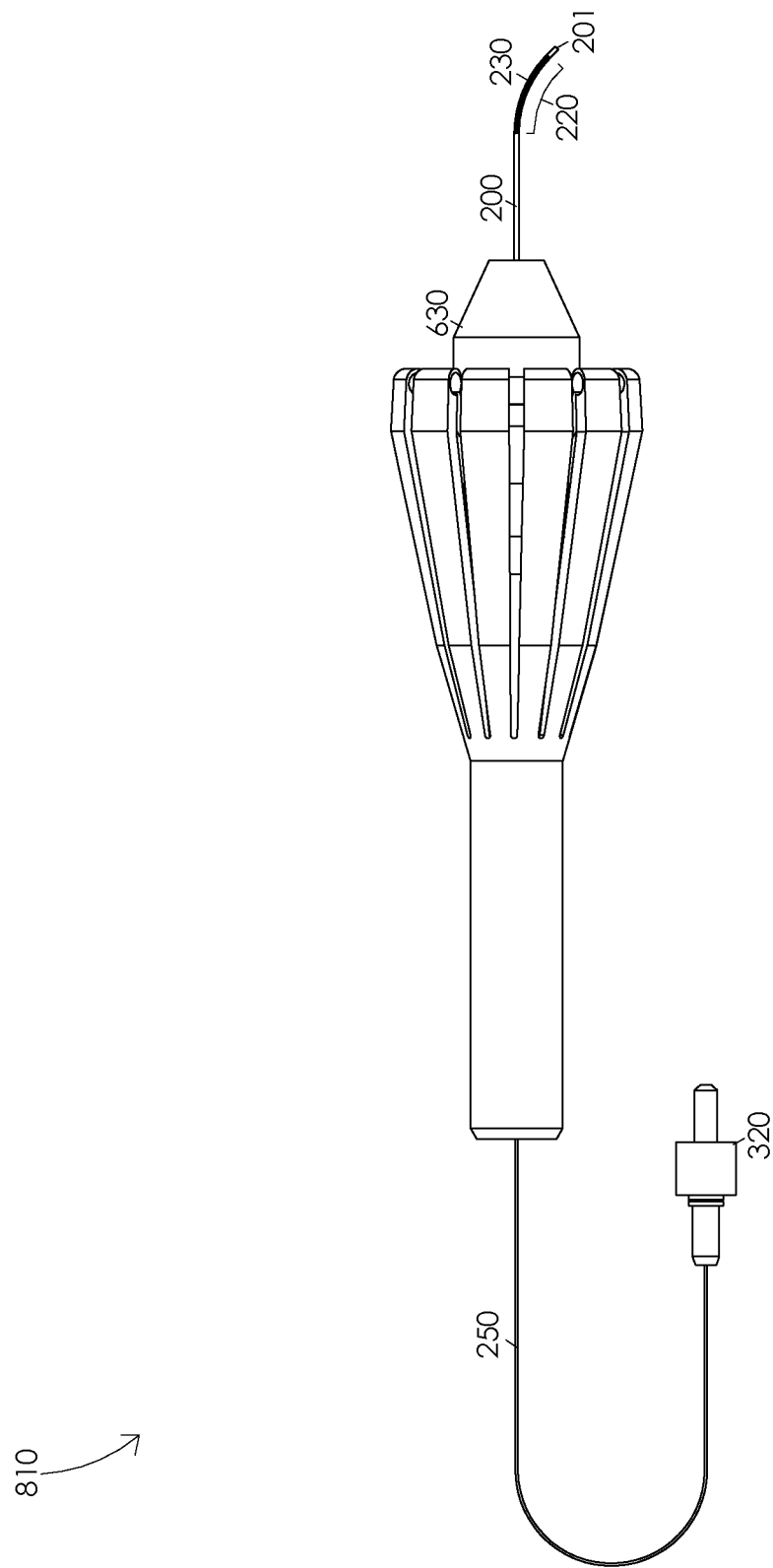

FIG. 8B illustrates an optic fiber in a first curved position 810. In one or more embodiments, a compression of actuation structure 620 may be configured to gradually curve optic fiber 250 from a straight optic fiber 800 to an optic fiber in a first curved position 810. Illustratively, a compression of actuation structure 620 may be configured to gradually retract wire 340 relative to housing tube 200. In one or more embodiments, a refraction of wire 340 relative to housing tube 200 may be configured to actuate a portion of pre-formed curve 345 out from a portion of housing tube 200, e.g., a portion of housing tube 200 configured to generally straighten pre-formed curve 345. Illustratively, a refraction of wire 340 relative to housing tube 200 may be configured to actuate a portion of pre-formed curve 345 into a portion of housing tube 200, e.g., first housing tube portion 220. In one or more embodiments, a compression of actuation structure 620 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from a straight optic fiber 800 to an optic fiber in a first curved position 810. Illustratively, a line tangent to optic fiber distal end 251 may intersect a line tangent to housing tube proximal end 202 at a first angle, e.g., when optic fiber 250 comprises an optic fiber in a first curved position 810. In one or more embodiments, the first angle may comprise any angle greater than zero degrees. For example, the first angle may comprise a 45 degree angle.

Figure 8C:
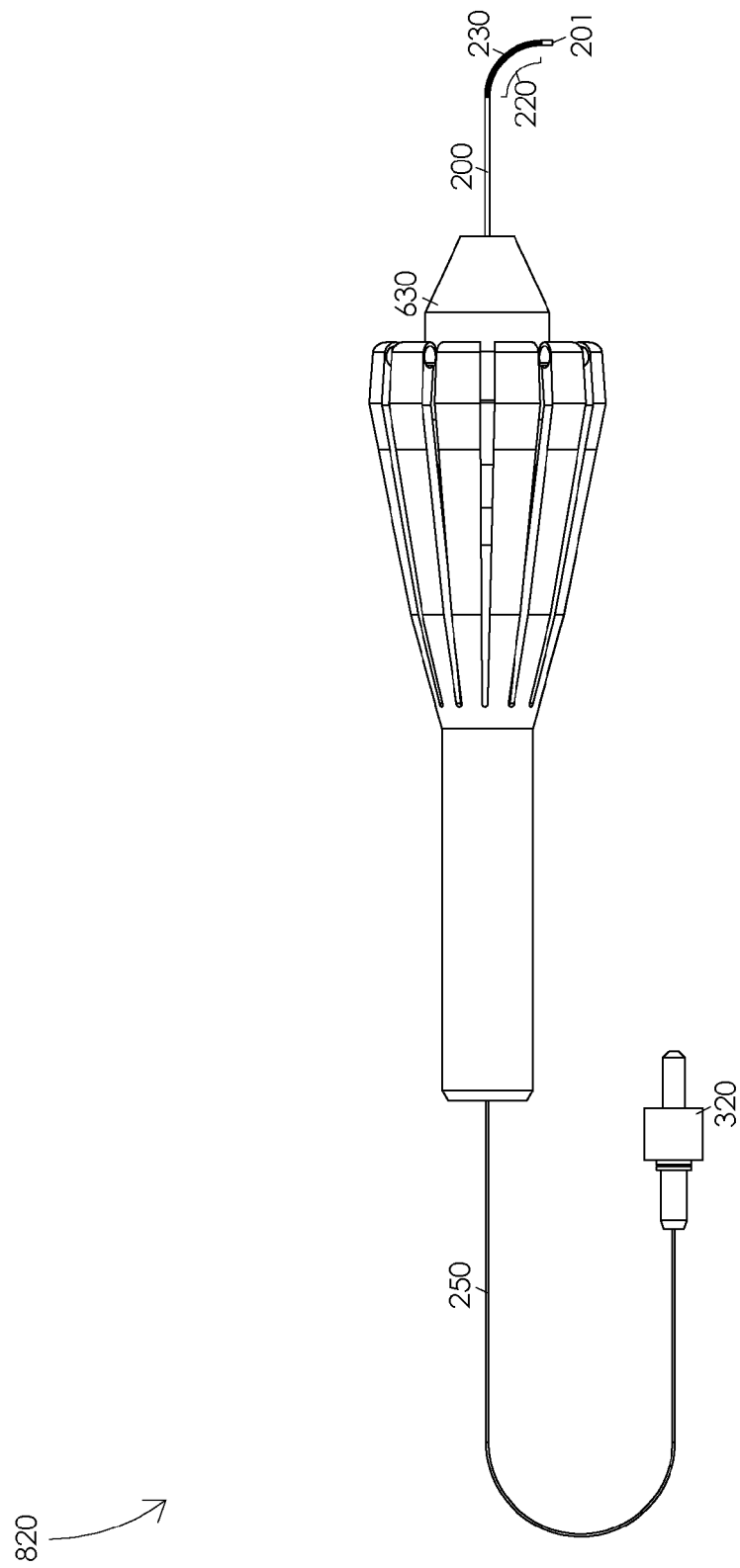

FIG. 8C illustrates an optic fiber in a second curved position 820. In one or more embodiments, a compression of actuation structure 620 may be configured to gradually curve optic fiber 250 from an optic fiber in a first curved position 810 to an optic fiber in a second curved position 820. Illustratively, a compression of actuation structure 620 may be configured to gradually retract wire 340 relative to housing tube 200. In one or more embodiments, a retraction of wire 340 relative to housing tube 200 may be configured to actuate a portion of pre-formed curve 345 out from a portion of housing tube 200, e.g., a portion of housing tube 200 configured to generally straighten pre-formed curve 345. Illustratively, a retraction of wire 340 relative to housing tube 200 may be configured to actuate a portion of pre-formed curve 345 into a portion of housing tube 200, e.g., first housing tube portion 220. In one or more embodiments, a compression of actuation structure 620 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from an optic fiber in a first curved position 810 to an optic fiber in a second curved position 820. Illustratively, a line tangent to optic fiber distal end 251 may intersect a line tangent to housing tube proximal end 202 at a second angle, e.g., when optic fiber 250 comprises an optic fiber in a second curved position 820. In one or more embodiments, the second angle may comprise any angle greater than the first angle. For example, the second angle may comprise a 90 degree angle.

Figure 8D:
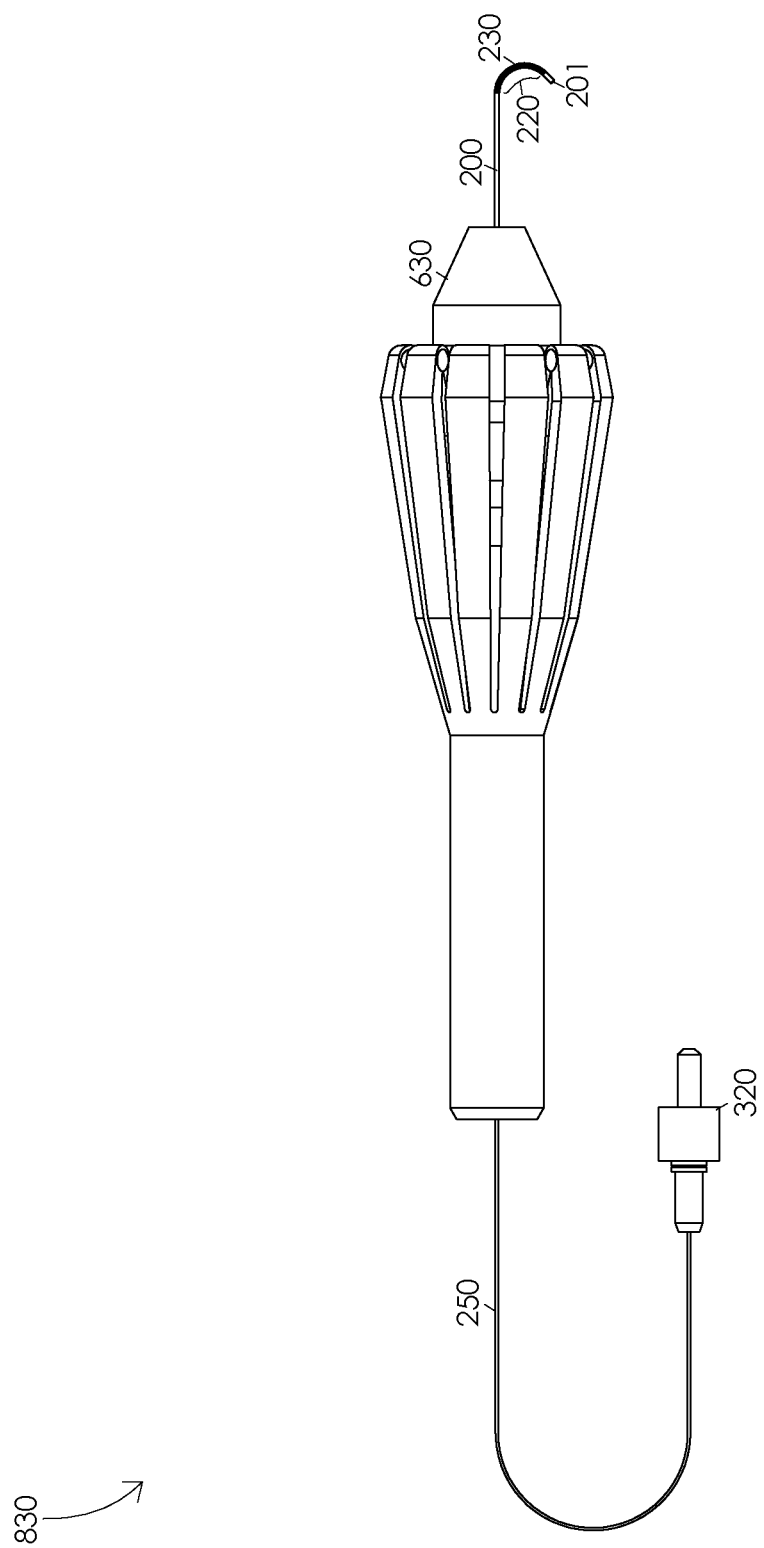

FIG. 8D illustrates an optic fiber in a third curved position 830. In one or more embodiments, a compression of actuation structure 620 may be configured to gradually curve optic fiber 250 from an optic fiber in a second curved position 820 to an optic fiber in a third curved position 830. Illustratively, a compression of actuation structure 620 may be configured to gradually retract wire 340 relative to housing tube 200. In one or more embodiments, a retraction of wire 340 relative to housing tube 200 may be configured to actuate a portion of pre-formed curve 345 out from a portion of housing tube 200, e.g., a portion of housing tube 200 configured to generally straighten pre-formed curve 345. Illustratively, a retraction of wire 340 relative to housing tube 200 may be configured to actuate a portion of pre-formed curve 345 into a portion of housing tube 200, e.g., first housing tube portion 220. In one or more embodiments, a compression of actuation structure 620 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from an optic fiber in a second curved position 820 to an optic fiber in a third curved position 830. Illustratively, a line tangent to optic fiber distal end 251 may intersect a line tangent to housing tube proximal end 202 at a third angle, e.g., when optic fiber 250 comprises an optic fiber in a third curved position 830. In one or more embodiments, the third angle may comprise any angle greater than the second angle. For example, the third angle may comprise a 135 degree angle.

Figure 8E:
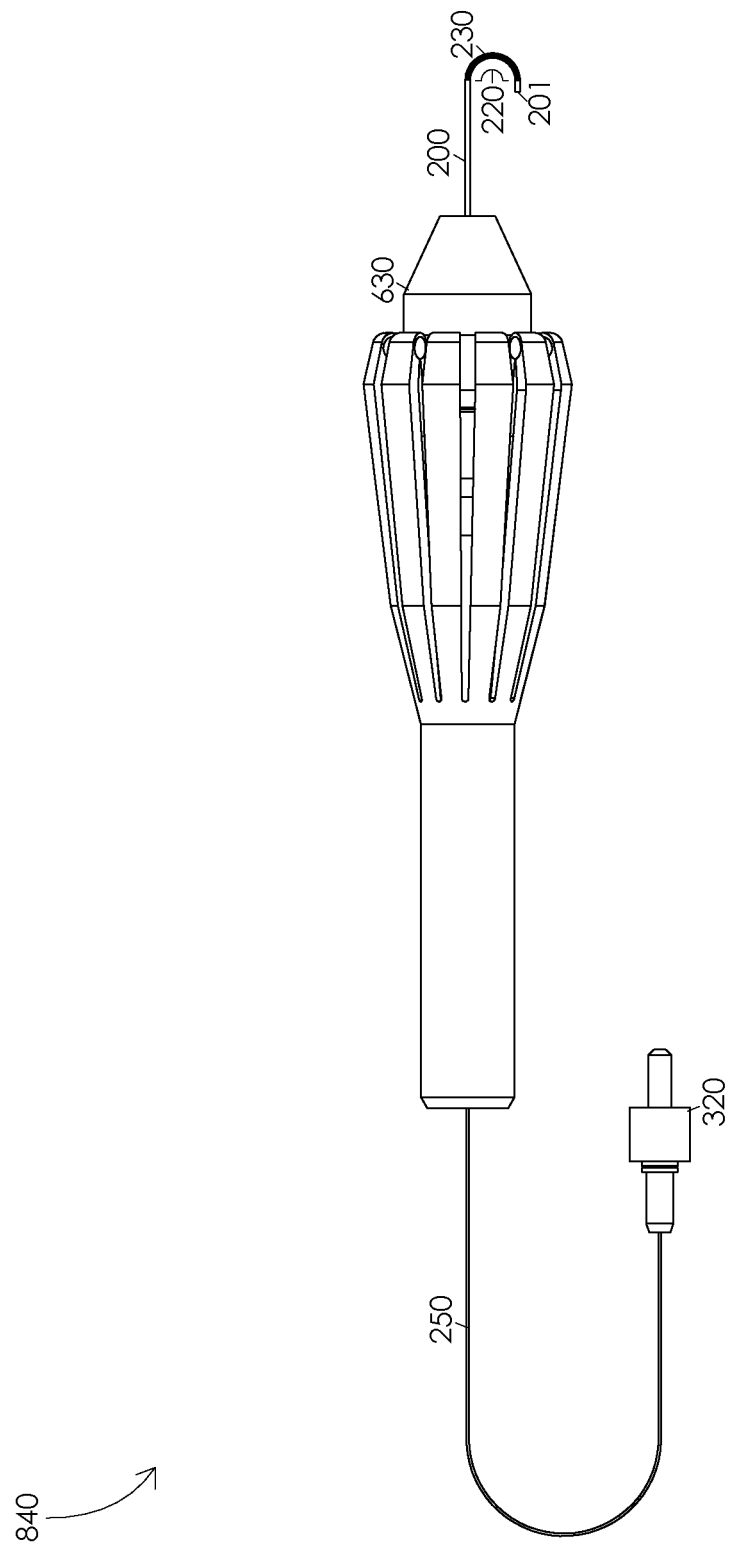

FIG. 8E illustrates an optic fiber in a fourth curved position 840. In one or more embodiments, a compression of actuation structure 620 may be configured to gradually curve optic fiber 250 from an optic fiber in a third curved position 830 to an optic fiber in a fourth curved position 840. Illustratively, a compression of actuation structure 620 may be configured to gradually retract wire 340 relative to housing tube 200. In one or more embodiments, a retraction of wire 340 relative to housing tube 200 may be configured to actuate a portion of pre-formed curve 345 out from a portion of housing tube 200, e.g., a portion of housing tube 200 configured to generally straighten pre-formed curve 345. Illustratively, a retraction of wire 340 relative to housing tube 200 may be configured to actuate a portion of pre-formed curve 345 into a portion of housing tube 200, e.g., first housing tube portion 220. In one or more embodiments, a compression of actuation structure 620 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from an optic fiber in a third curved position 830 to an optic fiber in a fourth curved position 840. Illustratively, a line tangent to optic fiber distal end 251 may be parallel to a line tangent to housing tube proximal end 202, e.g., when optic fiber 250 comprises an optic fiber in a fourth curved position 840.

In one or more embodiments, one or more properties of a steerable laser probe may be adjusted to attain one or more desired steerable laser probe features. For example, a length that housing tube 200 extends from housing tube platform 630 may be adjusted to vary an amount of compression of actuation structure 620 configured to curve housing tube 200 to a particular curved position. Illustratively, a length of wire 340 may be adjusted to vary an amount of compression of actuation structure 620 configured to curve housing tube 200 to a particular curved position. In one or more embodiments, a stiffness of first housing tube portion 220 or a stiffness of second housing tube portion 230 may be adjusted to vary an amount of compression of actuation structure 620 configured to curve housing tube 200 to a particular curved position. Illustratively, a geometry of pre-formed curve 345 may be adjusted to vary an amount of compression of actuation structure 620 configured to curve housing tube 200 to a particular curved position. In one or more embodiments, a material comprising wire 340 or a material comprising a portion of wire 340, e.g., pre-formed curve 345, may be adjusted to vary an amount of compression of actuation structure 620 configured to curve housing tube 200 to a particular curved position. Illustratively, a material comprising first housing tube portion 220 or a material comprising second housing tube portion 230 may be adjusted to vary an amount of compression of actuation structure 620 configured to curve housing tube 200 to a particular curved position.

In one or more embodiments, a number of apertures in housing tube 200 may be adjusted to vary an amount of compression of actuation structure 620 configured to curve housing tube 200 to a particular curved position. Illustratively, a location of one or more apertures in housing tube 200 may be adjusted to vary an amount of compression of actuation structure 620 configured to curve housing tube 200 to a particular curved position. In one or more embodiments, a geometry of one or more apertures in housing tube 200 may be adjusted to vary an amount of compression of action structure 620 configured to curve housing tube 200 to a particular curved position. Illustratively, a geometry of one or more apertures in housing tube 200 may be uniform, e.g., each aperture of the one or more apertures may have a same geometry. In one or more embodiments, a geometry of one or more apertures in housing tube 200 may be non-uniform, e.g., a first aperture in housing tube 200 may have a first geometry and a second aperture in housing tube 200 may have a second geometry.

Illustratively, a distance that housing tube platform 630 extends from handle proximal end 602 may be adjusted to vary an amount of compression of actuation structure 620 configured to curve housing tube 200 to a particular curved position. In one or more embodiments, a geometry of actuation structure 620 may be adjusted to vary an amount of compression of actuation structure 620 configured to curve housing tube 200 to a particular curved position. Illustratively, at least a portion of optic fiber 250 may be enclosed in an optic fiber sleeve configured to, e.g., protect optic fiber 250, vary a stiffness of optic fiber 250, vary an optical property of optic fiber 250, etc.

Illustratively, a stiffness of first housing tube portion 220 or a stiffness of second housing tube portion 230 may be adjusted to vary a bend radius of housing tube 200. In one or more embodiments, a stiffness of first housing tube portion 220 or a stiffness of second housing tube portion 230 may be adjusted to vary a radius of curvature of housing tube 200, e.g., when housing tube 200 is in a particular curved position. Illustratively, a number of apertures in housing tube 200 may be adjusted to vary a bend radius of housing tube 200. In one or more embodiments, a number of apertures in housing tube 200 may be adjusted to vary a radius of curvature of housing tube 200, e.g., when housing tube 200 is in a particular curved position. Illustratively, a location or a geometry of one or more apertures in housing tube 200 may be adjusted to vary a bend radius of housing tube 200. In one or more embodiments, a location or a geometry of one or more apertures in housing tube 200 may be adjusted to vary a radius of curvature of housing tube 200, e.g., when housing tube 200 is in a particular curved position.

In one or more embodiments, a location of pre-formed curve 345 of wire 340 or a location of first housing tube portion 220 of housing tube 200 may be adjusted to vary one or more steerable laser probe features. Illustratively, a location of pre-formed curve 345 or a location of first housing tube portion 220 may be adjusted wherein a portion of pre-formed curve 345 may be disposed within first housing tube portion 220. In one or more embodiments, a relative location of pre-formed curve 345 and first housing tube portion 220 may be adjusted wherein a compression of actuation structure 620 may be configured to retract a portion of pre-formed curve 345 out from first housing tube portion 220 and into a portion of housing tube 200 configured to generally straighten pre-formed curve 345. Illustratively, a compression of actuation structure 620 may be configured to gradually straighten housing tube 200. In one or more embodiments, a gradual straightening of housing tube 200 may be configured to gradually straighten optic fiber 250.

Illustratively, wire 340 may comprise any suitable structure, e.g., wire 340 may comprise a cable. For example, wire 340 may comprise a cable having a pre-formed curve 345. In one or more embodiments, wire 340 may be replaced with a tube or a portion of wire 340 may comprise an inner bore. For example, wire 340 may be replaced with a tube having a pre-formed curve 345.

Illustratively, a location of pre-formed curve 345 or a location of first housing tube portion 220 may be adjusted wherein a portion of pre-formed curve 345 may be disposed within a portion of housing tube 200 configured to generally straighten pre-formed curve 345. In one or more embodiments, a relative location of pre-formed curve 345 and first housing tube portion 220 may be adjusted wherein a decompression of actuation structure 620 may be configured to extend a portion of pre-formed curve 345 into first housing tube portion 220 and out from a portion of housing tube 200 configured to generally straighten pre-formed curve 345. Illustratively, a decompression of actuation structure 620 may be configured to gradually curve housing tube 200. In one or more embodiments, a gradual curving of housing tube 200 may be configured to gradually curve optic fiber 250.

Figure 9A:
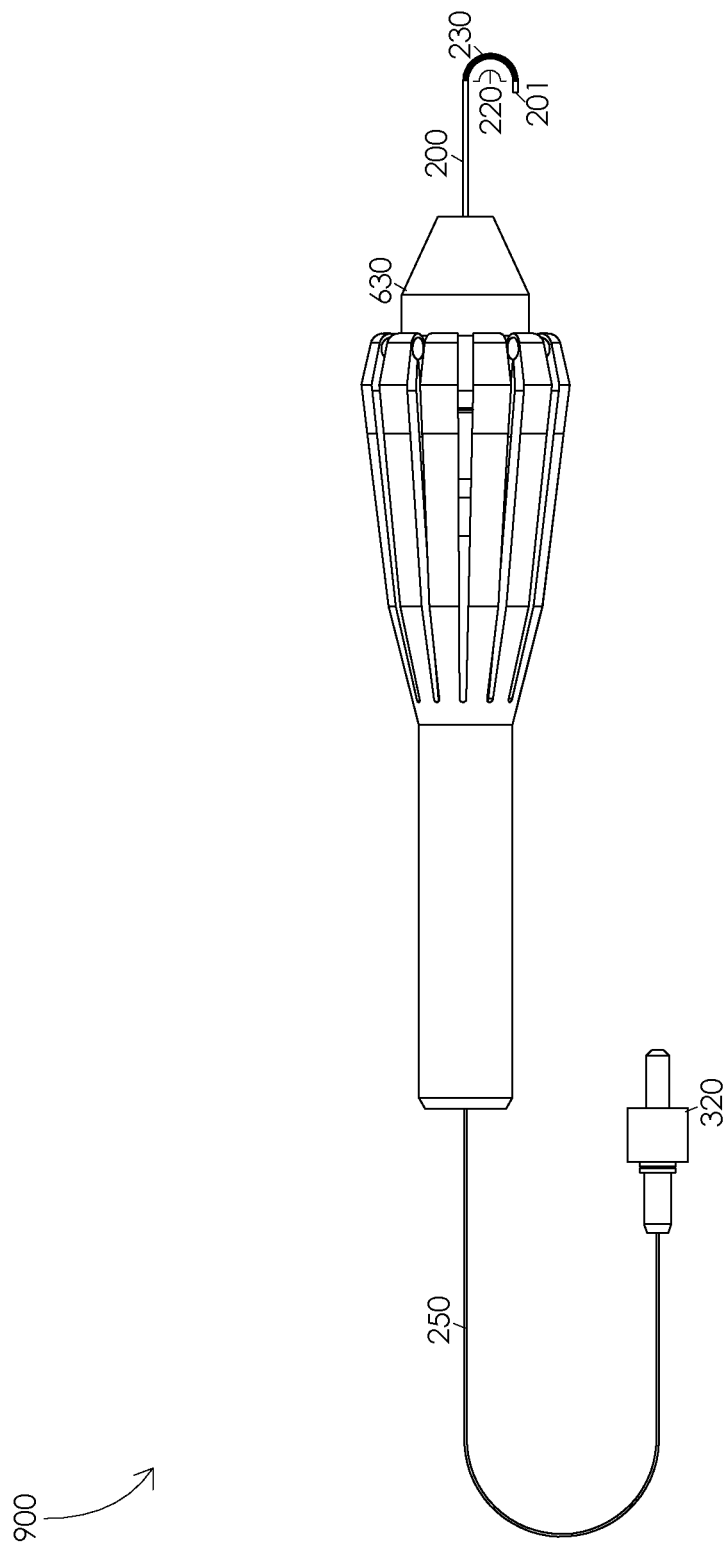
FIGS. 9A, 9B, 9C, 9D, and 9E illustrate a gradual straightening of an optic fiber.

FIGS. 9A, 9B, 9C, 9D, and 9E illustrate a gradual straightening of an optic fiber 250. FIG. 9A illustrates a fully curved optic fiber 900. In one or more embodiments, optic fiber 250 may comprise a fully curved optic fiber 900, e.g., when actuation platform 640 is fully retracted relative to handle base 610. Illustratively, optic fiber 250 may comprise a fully curved optic fiber 900, e.g., when wire 340 is fully retracted relative to housing tube 200. In one or more embodiments, optic fiber 250 may comprise a fully curved optic fiber 900, e.g., when actuation structure 620 is fully compressed. Illustratively, a line tangent to optic fiber distal end 251 may be parallel to a line tangent to housing tube proximal end 202, e.g., when optic fiber 250 comprises a fully curved optic fiber 900.

Figure 9B:
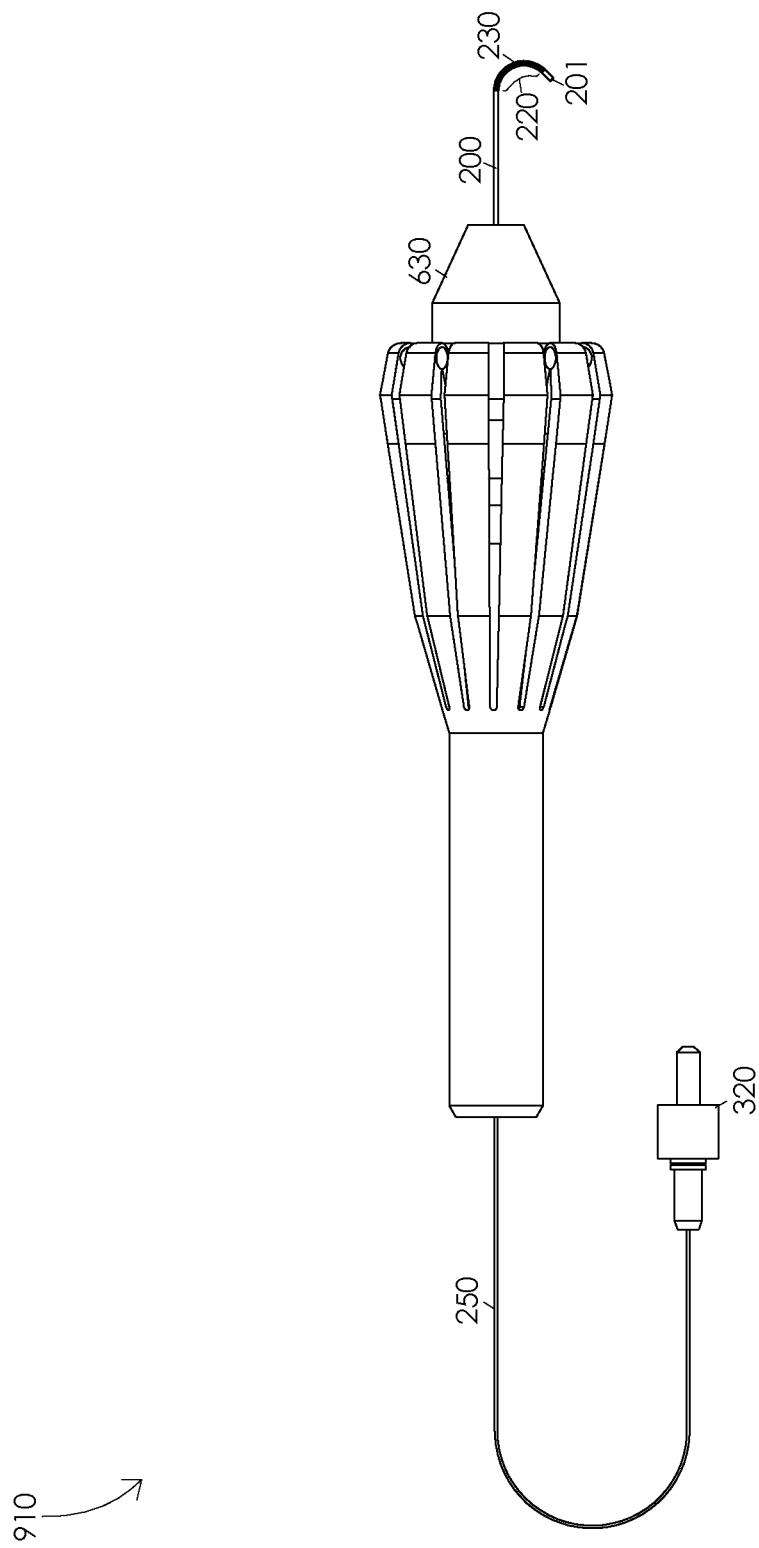

FIG. 9B illustrates an optic fiber in a first partially straightened position 910. In one or more embodiments, a decompression of actuation structure 620 may be configured to gradually straighten optic fiber 250 from a fully curved optic fiber 900 to an optic fiber in a first partially straightened position 910. Illustratively, a decompression of actuation structure 920 may be configured to gradually extend wire 340 relative to housing tube 200. In one or more embodiments, an extension of wire 340 relative to housing tube 200 may be configured to actuate a portion of pre-formed curve 345 into a portion of housing tube 200, e.g., a portion of housing tube 200 configured to generally straighten pre-formed curve 345. Illustratively, an extension of wire 340 relative to housing tube 200 may be configured to actuate a portion of pre-formed curve 345 out from a portion of housing tube 200, e.g., first housing tube portion 220. In one or more embodiments, a decompression of actuation structure 620 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from a fully curved optic fiber 900 to an optic fiber in a first partially straightened position 910. Illustratively, a line tangent to optic fiber distal end 251 may intersect a line tangent to housing tube proximal end 202 at a first partially straightened angle, e.g., when optic fiber 250 comprises an optic fiber in a first partially straightened position 910. In one or more embodiments, the first partially straightened angle may comprise any angle less than 180 degrees. For example, the first partially straightened angle may comprise a 135 degree angle.

Figure 9C:
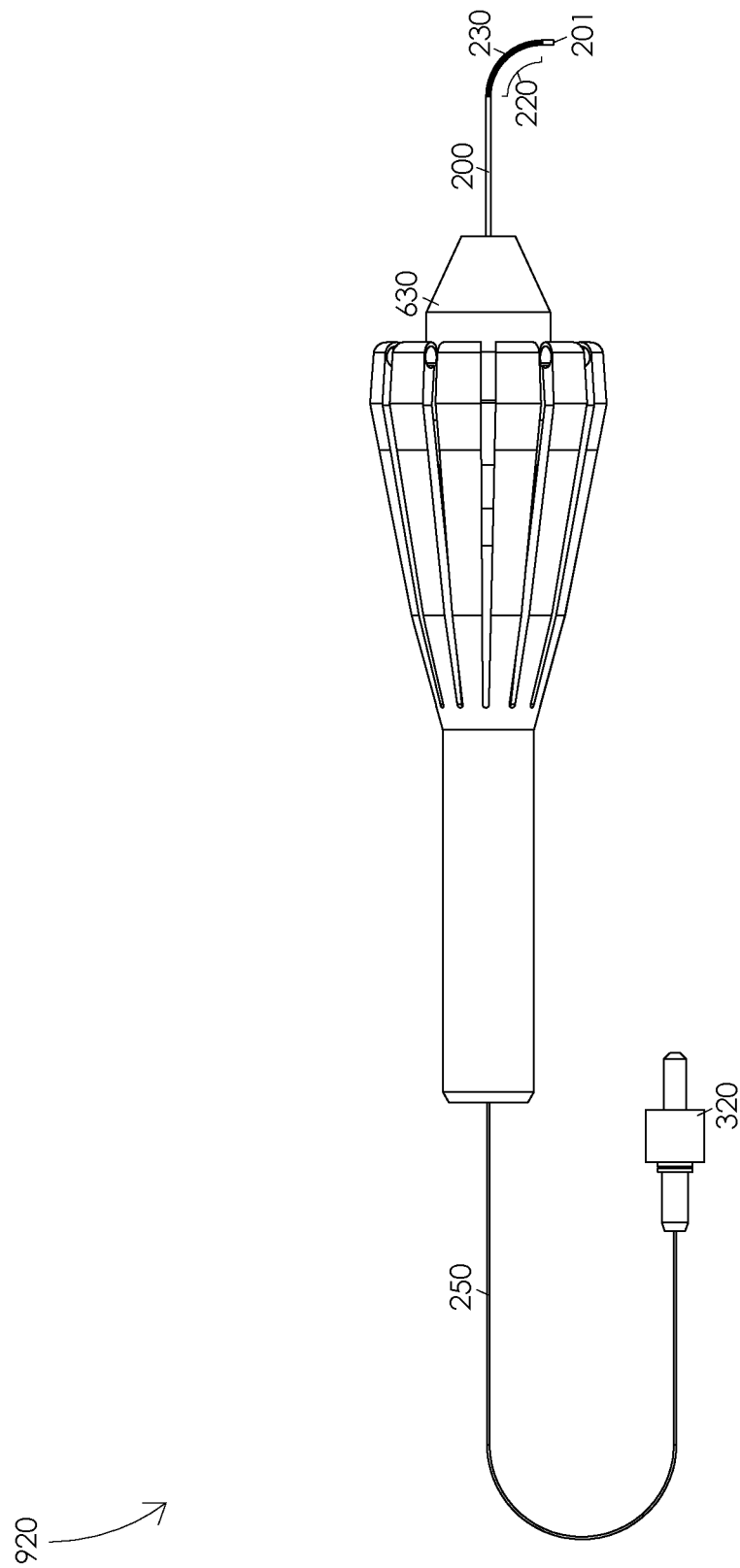

FIG. 9C illustrates an optic fiber in a second partially straightened position 920. In one or more embodiments, a decompression of actuation structure 620 may be configured to gradually straighten optic fiber 250 from an optic fiber in a first partially straightened position 910 to an optic fiber in a second partially straightened position 920. Illustratively, a decompression of actuation structure 920 may be configured to gradually extend wire 340 relative to housing tube 200. In one or more embodiments, an extension of wire 340 relative to housing tube 200 may be configured to actuate a portion of pre-formed curve 345 into a portion of housing tube 200, e.g., a portion of housing tube 200 configured to generally straighten pre-formed curve 345. Illustratively, an extension of wire 340 relative to housing tube 200 may be configured to actuate a portion of pre-formed curve 345 out from a portion of housing tube 200, e.g., first housing tube portion 220. In one or more embodiments, a decompression of actuation structure 620 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from an optic fiber in a first partially straightened position 910 to an optic fiber in a second partially straightened position 920. Illustratively, a line tangent to optic fiber distal end 251 may intersect a line tangent to housing tube proximal end 202 at a second partially straightened angle, e.g., when optic fiber 250 comprises an optic fiber in a second partially straightened position 920. In one or more embodiments, the second partially straightened angle may comprise any angle less than the first partially straightened angle. For example, the second partially straightened angle may comprise a 90 degree angle.

Figure 9D:
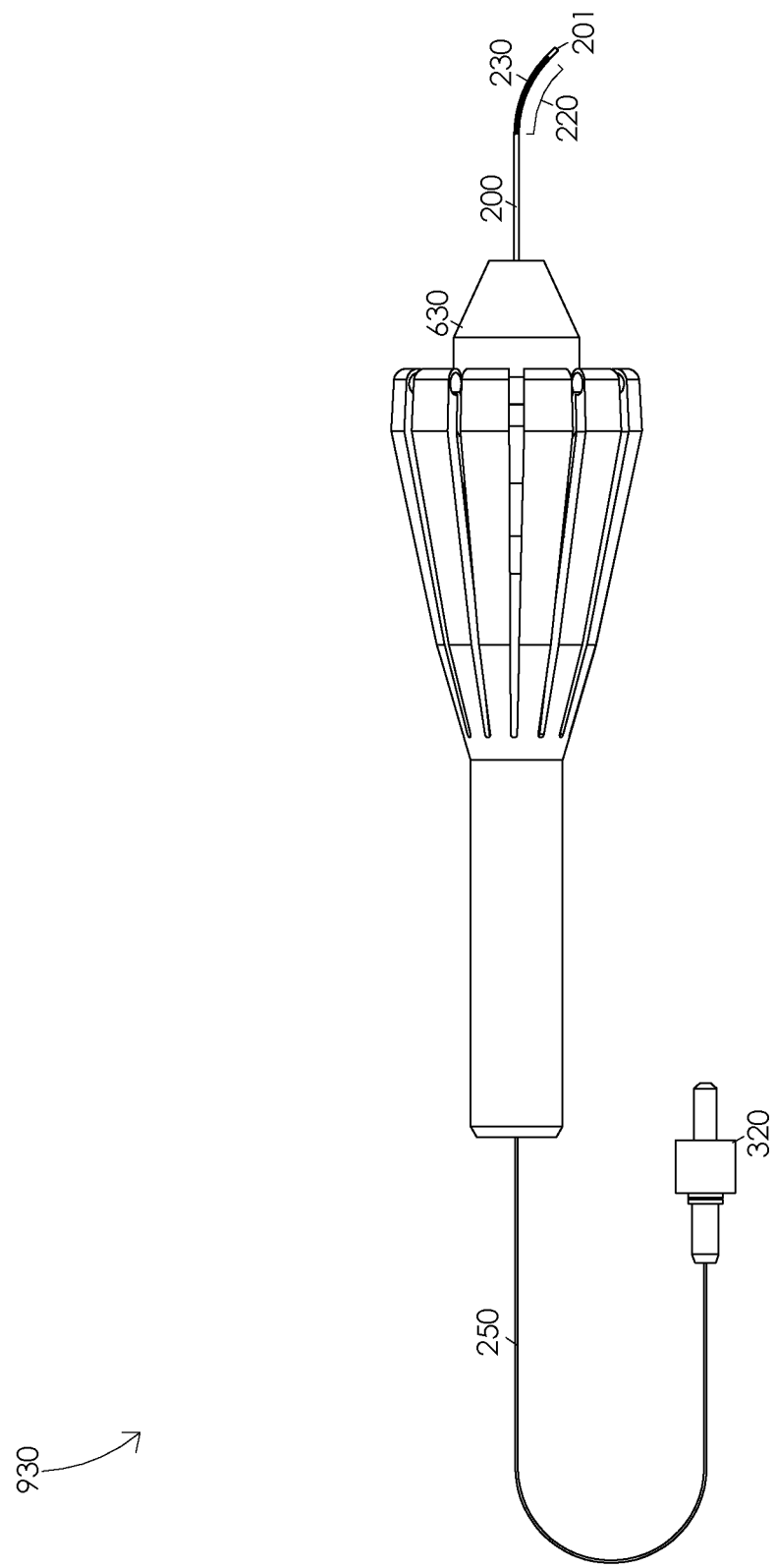

FIG. 9D illustrates an optic fiber in a third partially straightened position 930. In one or more embodiments, a decompression of actuation structure 620 may be configured to gradually straighten optic fiber 250 from an optic fiber in a second partially straightened position 920 to an optic fiber in a third partially straightened position 930. Illustratively, a decompression of actuation structure 920 may be configured to gradually extend wire 340 relative to housing tube 200. In one or more embodiments, an extension of wire 340 relative to housing tube 200 may be configured to actuate a portion of pre-formed curve 345 into a portion of housing tube 200, e.g., a portion of housing tube 200 configured to generally straighten pre-formed curve 345. Illustratively, an extension of wire 340 relative to housing tube 200 may be configured to actuate a portion of pre-formed curve 345 out from a portion of housing tube 200, e.g., first housing tube portion 220. In one or more embodiments, a decompression of actuation structure 620 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from an optic fiber in a second partially straightened position 920 to an optic fiber in a third partially straightened position 930. Illustratively, a line tangent to optic fiber distal end 251 may intersect a line tangent to housing tube proximal end 202 at a third partially straightened angle, e.g., when optic fiber 250 comprises an optic fiber in a third partially straightened position 930. In one or more embodiments, the third partially straightened angle may comprise any angle less than the second partially straightened angle. For example, the third partially straightened angle may comprise a 45 degree angle.

Figure 9E:
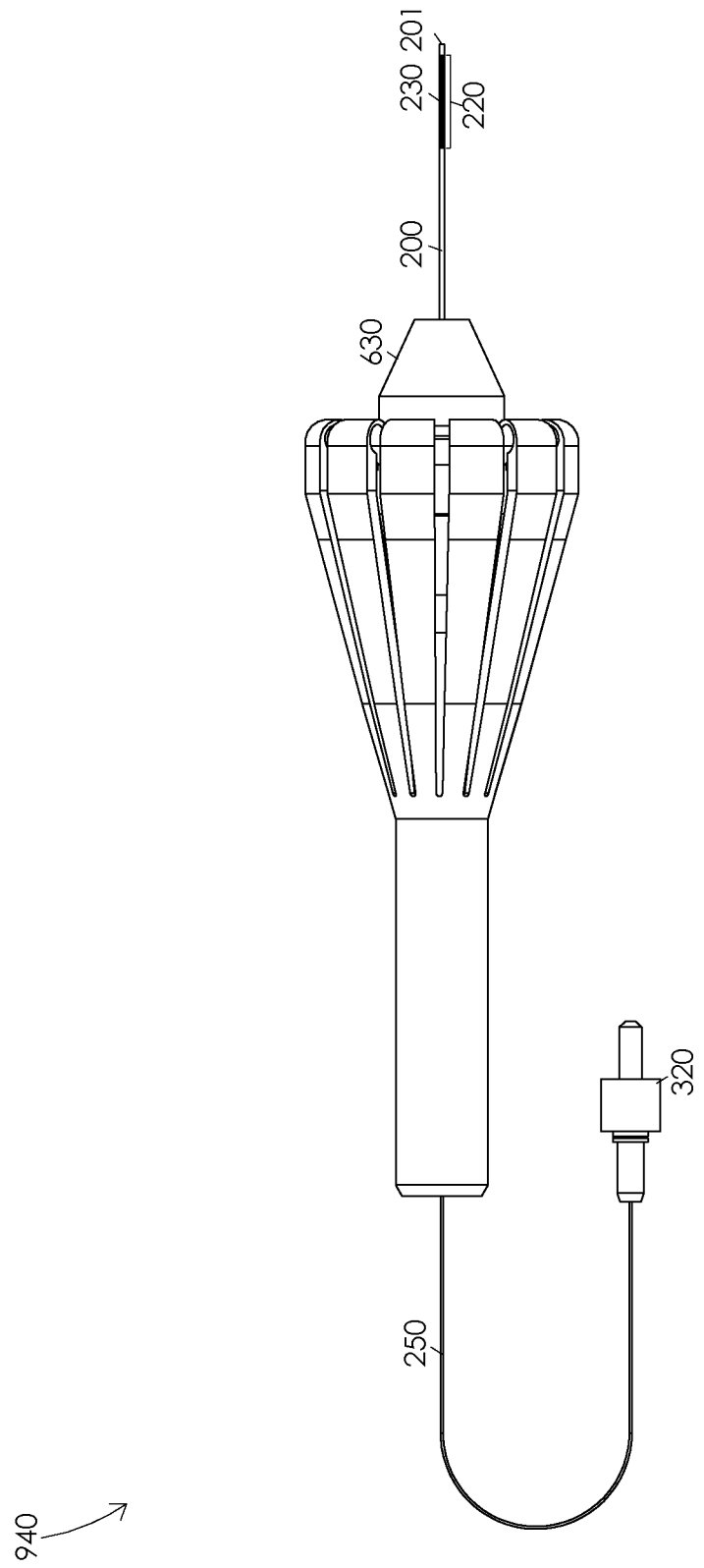

FIG. 9E illustrates an optic fiber in a fully straightened position 940. In one or more embodiments, a decompression of actuation structure 620 may be configured to gradually straighten optic fiber 250 from an optic fiber in a third partially straightened position 930 to an optic fiber in a fully straightened position 940. Illustratively, a decompression of actuation structure 920 may be configured to gradually extend wire 340 relative to housing tube 200. In one or more embodiments, an extension of wire 340 relative to housing tube 200 may be configured to actuate a portion of pre-formed curve 345 into a portion of housing tube 200, e.g., a portion of housing tube 200 configured to generally straighten pre-formed curve 345. Illustratively, an extension of wire 340 relative to housing tube 200 may be configured to actuate a portion of pre-formed curve 345 out from a portion of housing tube 200, e.g., first housing tube portion 220. In one or more embodiments, a decompression of actuation structure 620 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from an optic fiber in a third partially straightened position 930 to an optic fiber in a fully straightened position 940. Illustratively, a line tangent to optic fiber distal end 251 may be parallel to a line tangent to housing tube proximal end 202, e.g., when optic fiber 250 comprises an optic fiber in a fully straightened position 940.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 600 to orient housing tube 200 in an orientation configured to cause a curvature of housing tube 200 within the particular transverse plane of the inner eye and varying an amount of compression of actuation structure 620. Illustratively, a surgeon may aim optic fiber distal end 251 at any target within a particular sagittal plane of the inner eye by, e.g., rotating handle 600 to orient housing tube 200 in an orientation configured to cause a curvature of housing tube 200 within the particular sagittal plane of the inner eye and varying an amount of compression of actuation structure 620. In one or more embodiments, a surgeon may aim optic fiber distal end 251 at any target within a particular frontal plane of the inner eye by, e.g., varying an amount of compression of actuation structure 620 to orient a line tangent to optic fiber distal end 251 wherein the line tangent to optic fiber distal end 251 is within the particular frontal plane of the inner eye and rotating handle 600. Illustratively, a surgeon may aim optic fiber distal end 251 at any target located outside of the particular transverse plane, the particular sagittal plane, and the particular frontal plane of the inner eye, e.g., by varying a rotational orientation of handle 600 and varying an amount of compression of actuation structure 620. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

FIGS. 10A and 10B are schematic diagrams illustrating a handle 1000. FIG. 10A illustrates a top view of handle 1000. Illustratively, handle 1000 may comprise a handle distal end 1001, a handle proximal end 1002, a handle base 1010, an actuation structure 1020 having an actuation structure distal end 1021 and an actuation structure proximal end 1022, and an actuation ring 1030. In one or more embodiments, actuation structure 1020 may comprise a plurality of actuation arms 1025. Illustratively, each actuation arm 1025 may comprise at least one extension mechanism 1026. In one or more embodiments, actuation structure 1020 may comprise a shape memory material configured to project actuation structure distal end 1021 a first distance from actuation structure proximal end 1022, e.g., when actuation structure 1020 is fully decompressed. Illustratively, actuation structure 1020 may comprise a shape memory material configured to project actuation structure distal end 1021 a second distance from actuation structure proximal end 1022, e.g., when actuation structure 1020 is fully compressed. In one or more embodiments, the second distance from actuation structure proximal end 1022 may be greater than the first distance from actuation structure proximal end 1022. Actuation structure 1020 may be manufactured from any suitable material, e.g., polymers, metals, metal alloys, etc., or from any combination of suitable materials.

Illustratively, actuation structure 1020 may be compressed by an application of a compressive force to actuation structure 1020. In one or more embodiments, actuation structure 1020 may be compressed by an application of one or more compressive forces located at one or more locations around an outer perimeter of actuation structure 1020. Illustratively, the one or more locations may comprise any of a plurality of locations around the outer perimeter of actuation structure 1020. For example, a surgeon may compress actuation structure 1020, e.g., by squeezing actuation structure 1020. Illustratively, the surgeon may compress actuation structure 1020 by squeezing actuation structure 1020 at any particular location of a plurality of locations around an outer perimeter of actuation structure 1020. For example, a surgeon may rotate handle 1000 and compress actuation structure 1020 from any rotational position of a plurality of rotational positions of handle 1000.

In one or more embodiments, actuation structure 1020 may be compressed by an application of a compressive force to any one or more of the plurality of actuation arms 1025. Illustratively, each actuation arm 1025 may be configured to actuate independently. In one or more embodiments, each actuation arm 1025 may be connected to one or more of the plurality of actuation arms 1025 wherein an actuation of a particular actuation arm 1025 may be configured to actuate every actuation arm 1025 of the plurality of actuation arms 1025. Illustratively, one or more actuation arms 1025 may be configured to actuate in pairs or groups. For example, an actuation of a first actuation arm 1025 may be configured to actuate a second actuation arm 1025.

In one or more embodiments, a compression of actuation structure 1020, e.g., due to an application of a compressive force to a particular actuation arm 1025, may be configured to actuate the particular actuation arm 1025. Illustratively, an actuation of the particular actuation arm 1025 may be configured to actuate every actuation arm 1025 of the plurality of actuation arms 1025. In one or more embodiments, an application of a compressive force to a particular actuation arm 1025 may be configured to extend at least one extension mechanism 1026 of the particular actuation arm 1025. Illustratively, a particular actuation arm 1025 may be configured to extend a first length from handle base 1010. In one or more embodiments, an extension of an extension mechanism 1026 of the particular actuation arm 1025, e.g., due to an application of a compressive force to the particular actuation arm 1025, may be configured to extend the particular actuation arm 1025 a second length from handle base 1010. Illustratively, the second length from handle base 1010 may be greater than the first length from handle base 1010.

In one or more embodiments, actuation ring 1030 may be fixed to actuation structure distal end 1021. Illustratively, a compression of actuation structure 1020 may be configured to gradually extend actuation ring 1030 from handle base 1010. For example, actuation ring 1030 may be configured to extend a first distance from actuation structure proximal end 1022, e.g., when actuation structure 1020 is fully decompressed. In one or more embodiments, actuation ring 1030 may be configured to extend a second distance from actuation structure proximal end 1022, e.g., due to a compression of actuation structure 1020. Illustratively, the second distance from actuation structure proximal end 1022 may be greater than the first distance from actuation structure proximal end 1022.

FIG. 10B illustrates a cross-sectional view of handle 1000. In one or more embodiments, handle 1000 may comprise a fixation mechanism housing 1040, an inner bore 1060, an inner bore proximal taper 1061, an inner bore distal chamber 1062, an optic fiber guide 1063, and a wire housing 1064. Handle 1000 may be manufactured from any suitable material, e.g., polymers, metals, metal alloys, etc., or from any combination of suitable materials.

Figure 11:
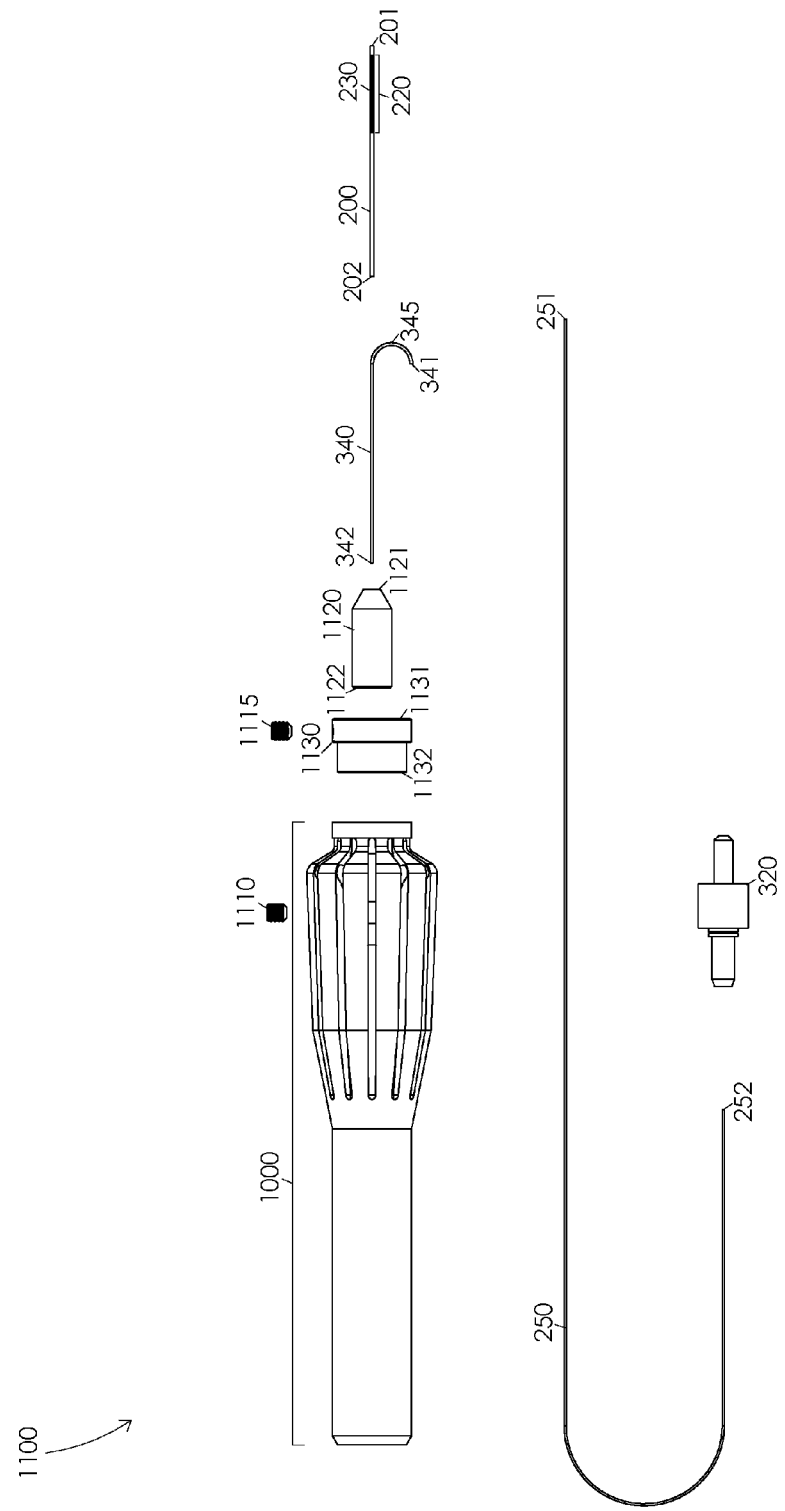
FIG. 11 is a schematic diagram illustrating an exploded view of a steerable laser probe assembly.

FIG. 11 is a schematic diagram illustrating an exploded view of a steerable laser probe assembly 1100. In one or more embodiments, steerable laser probe assembly 1100 may comprise a handle 1000; a fixation mechanism 1110; a nosecone fixation mechanism 1115; an inner nosecone 1120 having an inner nosecone distal end 1121 and an inner nosecone proximal end 1122; an outer nosecone 1130 having an outer nosecone distal end 1131 and an outer nosecone proximal end 1132; a housing tube 200 having a housing tube distal end 201, a housing tube proximal end 202, a first housing tube portion 220, and a second housing tube portion 230; a wire 340 having a wire distal end 341, a wire proximal end 342, and a pre-formed curve 345; an optic fiber 250 having an optic fiber distal end 251 and an optic fiber proximal end 252; and a light source interface 320. Illustratively, light source interface 320 may be configured to interface with optic fiber 250, e.g., at optic fiber proximal end 252. In one or more embodiments, light source interface 320 may comprise a standard light source connector, e.g., an SMA connector.

Illustratively, inner nosecone 1120 may be fixed to outer nosecone 1130, e.g., inner nosecone proximal end 1122 may be fixed to outer nosecone distal end 1131. In one or more embodiments, a portion of inner nosecone 1120 may be disposed within a portion of outer nosecone 1130, e.g., inner nosecone proximal end 1122 may be disposed within outer nosecone 1130. Illustratively, a portion of inner nosecone 1120 may be disposed within a portion of outer nosecone 1130 wherein inner nosecone 1120 is fixed to outer nosecone 1130. In one or more embodiments, inner nosecone 1120 may be fixed to outer nosecone 1130, e.g., by an adhesive or any suitable fixation means. Illustratively, nosecone fixation mechanism 1115 may be configured to fix inner nosecone 1120 to outer nosecone 1130. For example, nosecone fixation mechanism 1115 may comprise a set screw configured to firmly attach inner nosecone 1120 to outer nosecone 1130. In one or more embodiments, inner nosecone 1120 and outer nosecone 1130 may be manufactured as a single unit. Inner nosecone 1120 and outer nosecone 1130 may be manufactured from any suitable material, e.g., polymers, metals, metal alloys, etc., or from any combination of suitable materials.

Illustratively, outer nosecone 1130 may be fixed to actuation structure 1020, e.g., outer nosecone proximal end 1132 may be fixed to handle distal end 1001. In one or more embodiments, a portion of outer nosecone 1130 may be disposed within actuation ring 1030, e.g., outer nosecone proximal end 1132 may be disposed within actuation ring 1030. Illustratively, a portion of outer nosecone 1130 may be disposed within actuation ring 1030 wherein outer nosecone 1130 is fixed to actuation ring 1030. In one or more embodiments, outer nosecone 1130 may be fixed to actuation structure 1020, e.g., by an adhesive or any suitable fixation means.

Illustratively, housing tube 200 may be fixed to inner nosecone 1120, e.g., housing tube proximal end 202 may be fixed to inner nosecone distal end 1121. In one or more embodiments, housing tube 200 may be fixed to inner nosecone 1120, e.g., by an adhesive or any suitable fixation means. Illustratively, a portion of housing tube 200 may be disposed within a portion of inner nosecone 1120, e.g., housing tube proximal end 202 may be disposed within inner nosecone 1120. In one or more embodiments, a portion of housing tube 200 may be fixed within inner nosecone 1120, e.g., by an adhesive or any suitable fixation means.

Illustratively, optic fiber 250 may be disposed within inner bore 1060, optic fiber guide 1063, inner bore distal chamber 1062, and housing tube 200. In one or more embodiments, optic fiber 250 may be disposed within housing tube 200 wherein optic fiber distal end 251 may be adjacent to housing tube distal end 201. Illustratively, a portion of optic fiber 250 may be fixed to an inner portion of housing tube 200, e.g., by an adhesive or any suitable fixation means.

In one or more embodiments, a portion of wire 340 may comprise a shape memory material, e.g., Nitinol. Illustratively, pre-formed curve 345 may comprise a shape memory material, e.g., Nitinol. In one or more embodiments, wire 340 may be disposed within wire housing 1064, inner bore distal chamber 1062, and housing tube 200. Illustratively, fixation mechanism 1110 may be disposed within fixation mechanism housing 1040. For example, a portion of fixation mechanism 1110 may be disposed within wire housing 1064. Illustratively, fixation mechanism 1110 may be configured to fix a portion of wire 230, e.g., wire proximal end 342, in a position relative to handle 1000. In one or more embodiments, fixation mechanism 1110 may comprise a set screw configured to fix wire 340 in a position relative to handle 1000, e.g., by a press fit or any suitable fixation means. Illustratively, a portion of wire 340, e.g., wire proximal end 342, may be fixed to fixation mechanism 1110, e.g., by an adhesive or any suitable fixation means. Wire 340 may be manufactured from any suitable material, e.g., polymers, metals, metal alloys, etc., or from any combination of suitable materials.

In one or more embodiments, a compression of actuation structure 1020 may be configured to extend actuation ring 1030 relative to handle base 1010. Illustratively, an extension of actuation ring 1030 relative to handle base 1010 may be configured to extend outer nosecone 1130, inner nosecone 1120, and housing tube 200 relative to handle base 1010. In one or more embodiments, a compression of actuation structure 1020 may be configured to actuate housing tube 200 relative to wire 340. Illustratively, a compression of actuation structure 1020 may be configured to extend housing tube 200 relative to wire 340. In one or more embodiments, an extension of housing tube 200 relative to wire 340 may be configured to extend a portion of housing tube 200 over a portion of wire 340, e.g., pre-formed curve 345. Illustratively, a compression of actuation structure 1020 may be configured to actuate a portion of housing tube 200 over wire 340, e.g., away from wire proximal end 342 and towards wire distal end 341.

In one or more embodiments, a portion of housing tube 200 may be configured to generally straighten pre-formed curve 345. Illustratively, an actuation of a portion of housing tube 200, e.g., a portion of housing tube 200 configured to generally straighten pre-formed curve 345, over a portion of pre-formed curve 345 may be configured to cause housing tube 200 to gradually straighten. In one or more embodiments, an actuation of a portion of housing tube 200, e.g., first housing tube portion 220, away from a portion of pre-formed curve 345 may be configured to cause housing tube 200 to gradually straighten. For example, as a portion of housing tube 200 configured to generally straighten pre-formed curve 345 is actuated over a portion of pre-formed curve 345 one or more properties, e.g., a stiffness, of the portion of housing tube 200 may cause housing tube 200 to gradually straighten. Illustratively, a compression of actuation structure 1020 may be configured to gradually straighten housing tube 200. In one or more embodiments, a gradual straightening of housing tube 200 may be configured to gradually straighten optic fiber 250. Illustratively, a compression of actuation structure 1020 may be configured to gradually straighten optic fiber 250.

In one or more embodiments, a decompression of actuation structure 1020 may be configured to retract actuation ring 1030 relative to handle base 1010. Illustratively, a refraction of actuation ring 1030 relative to handle base 1010 may be configured to retract outer nosecone 1130, inner nosecone 1120, and housing tube 200 relative to handle base 1010. In one or more embodiments, a decompression of actuation structure 1020 may be configured to actuate housing tube 200 relative to wire 340. Illustratively, a decompression of actuation structure 1020 may be configured to retract housing tube 200 relative to wire 340. In one or more embodiments, a retraction of housing tube 200 relative to wire 340 may be configured to retract a portion of housing tube 200 over a portion of wire 340, e.g., pre-formed curve 345. Illustratively, a decompression of actuation structure 1020 may be configured to actuate a portion of housing tube 200 over wire 340, e.g., towards wire proximal end 342 and away from wire distal end 341.

In one or more embodiments, a portion of housing tube 200 may be configured to generally straighten pre-formed curve 345. Illustratively, an actuation of a portion of housing tube 200, e.g., a portion of housing tube 200 configured to generally straighten pre-formed curve 345, away from pre-formed curve 345 may be configured to cause housing tube 200 to gradually curve. In one or more embodiments, an actuation of a portion of housing tube 200, e.g., first housing tube portion 220, over a portion of pre-formed curve 345 may be configured to cause housing tube 200 to gradually curve. For example, as a portion of first housing tube portion 220 is actuated over a portion of pre-formed curve 345 one or more properties, e.g., a stiffness, of first housing tube portion 220 may be configured to allow pre-formed curve 345 to gradually curve. Illustratively, a decompression of actuation structure 1020 may be configured to gradually curve housing tube 200. In one or more embodiments, a gradual curving of housing tube 200 may be configured to gradually curve optic fiber 250. Illustratively, a decompression of actuation structure 1020 may be configured to gradually curve optic fiber 250.

Figure 12A:
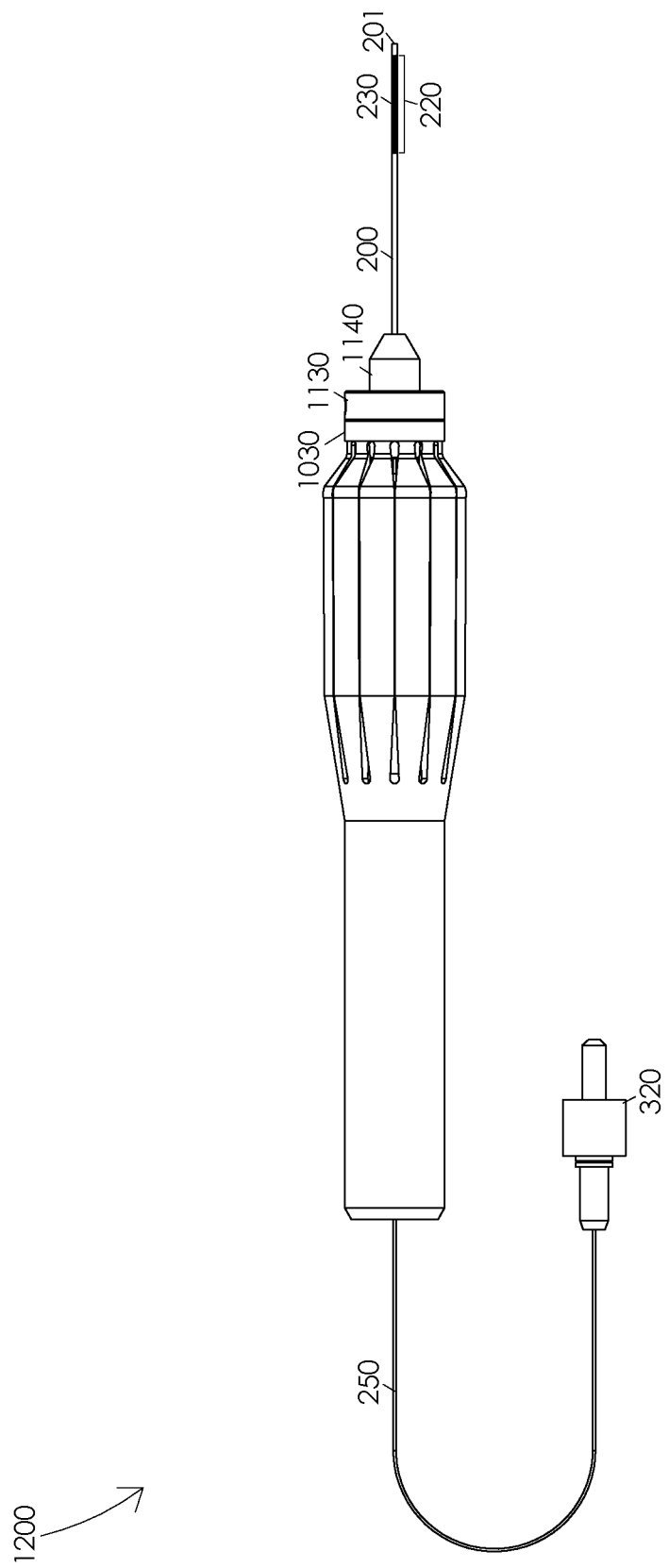
FIGS. 12A, 12B, 12C, 12D, and 12E illustrate a gradual curving of an optic fiber.

FIGS. 12A, 12B, 12C, 12D, and 12E illustrate a gradual curving of an optic fiber 250. FIG. 12A illustrates a straight optic fiber 1200. In one or more embodiments, optic fiber 250 may comprise a straight optic fiber 1200, e.g., when actuation ring 1030 is fully extended relative to handle base 1010. Illustratively, optic fiber 250 may comprise a straight optic fiber 1200, e.g., when housing tube 200 is fully extended relative to wire 340. In one or more embodiments, optic fiber 250 may comprise a straight optic fiber 1200, e.g., when actuation structure 1020 is fully compressed. Illustratively, a line tangent to optic fiber distal end 251 may be parallel to a line tangent to housing tube proximal end 202, e.g., when optic fiber 250 comprises a straight optic fiber 1200.

Figure 12B:
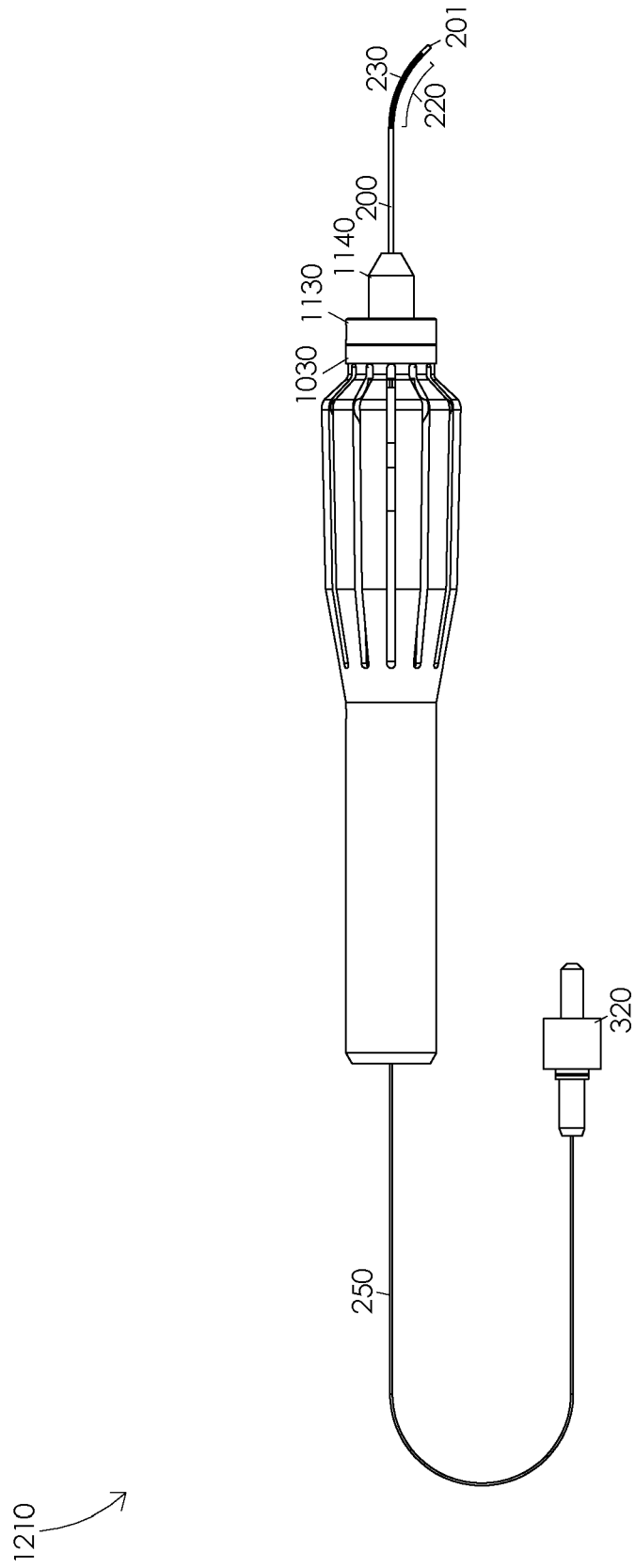

FIG. 12B illustrates an optic fiber in a first curved position 1210. In one or more embodiments, a decompression of actuation structure 1020 may be configured to gradually curve optic fiber 250 from a straight optic fiber 1200 to an optic fiber in a first curved position 1210. Illustratively, a decompression of actuation structure 1020 may be configured to gradually retract housing tube 200 relative to wire 340. In one or more embodiments, a refraction of housing tube 200 relative to wire 340 may be configured to actuate a portion of housing tube 200, e.g., a portion of housing tube 200 configured to generally straighten pre-formed curve 345, away from a portion of pre-formed curve 345. Illustratively, a retraction of housing tube 200 relative to wire 340 may be configured to actuate a portion of housing tube 200, e.g., first housing tube portion 220, over a portion of pre-formed curve 345. In one or more embodiments, a decompression of actuation structure 1020 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from a straight optic fiber 1200 to an optic fiber in a first curved position 1210. Illustratively, a line tangent to optic fiber distal end 251 may intersect a line tangent to housing tube proximal end 202 at a first angle, e.g., when optic fiber 250 comprises an optic fiber in a first curved position 1210. In one or more embodiments, the first angle may comprise any angle greater than zero degrees. For example, the first angle may comprise a 45 degree angle.

Figure 12C:
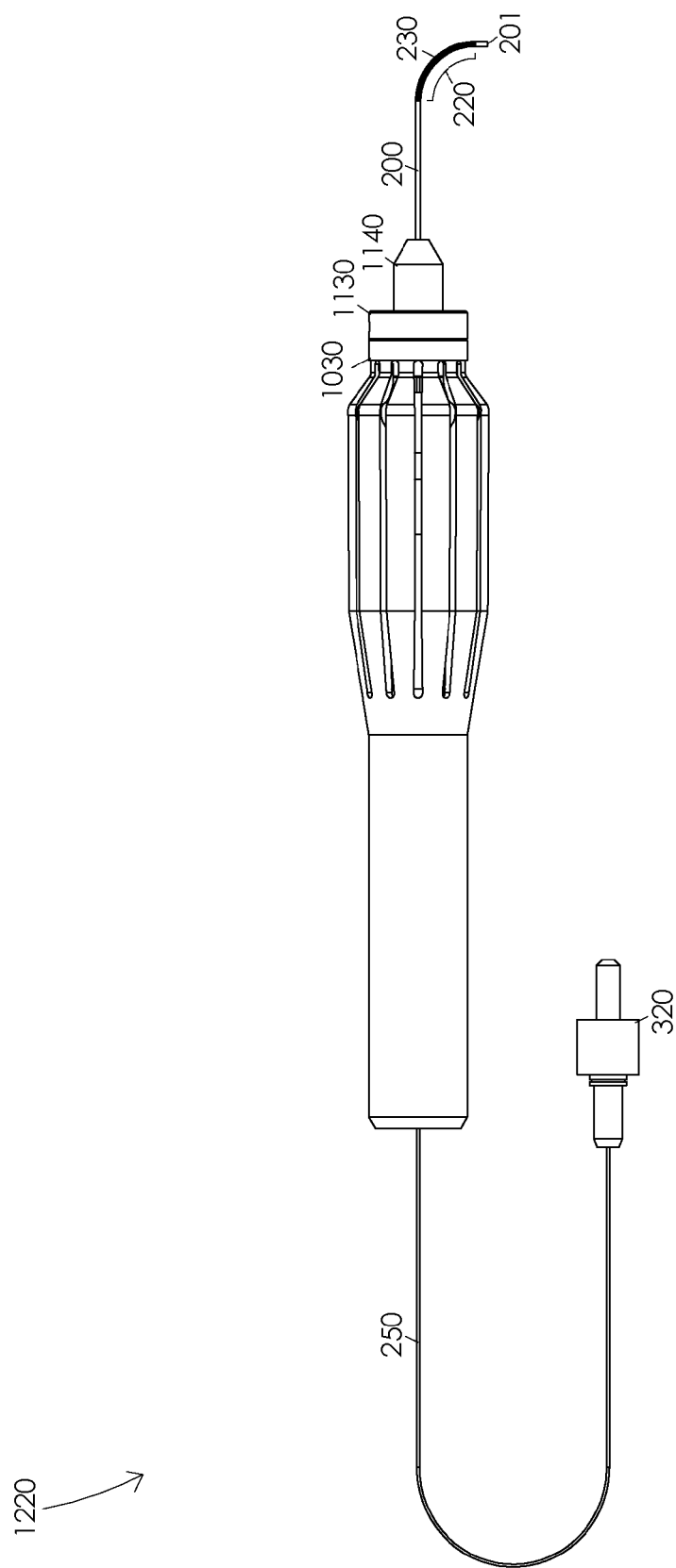

FIG. 12C illustrates an optic fiber in a second curved position 1220. In one or more embodiments, a decompression of actuation structure 1020 may be configured to gradually curve optic fiber 250 from an optic fiber in a first curved position 1210 to an optic fiber in a second curved position 1220. Illustratively, a decompression of actuation structure 1020 may be configured to gradually retract housing tube 200 relative to wire 340. In one or more embodiments, a retraction of housing tube 200 relative to wire 340 may be configured to actuate a portion of housing tube 200, e.g., a portion of housing tube 200 configured to generally straighten pre-formed curve 345, away from a portion of pre-formed curve 345. Illustratively, a retraction of housing tube 200 relative to wire 340 may be configured to actuate a portion of housing tube 200, e.g., first housing tube portion 220, over a portion of pre-formed curve 345. In one or more embodiments, a decompression of actuation structure 1020 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from an optic fiber in a first curved position 1210 to an optic fiber in a second curved position 1220. Illustratively, a line tangent to optic fiber distal end 251 may intersect a line tangent to housing tube proximal end 202 at a second angle, e.g., when optic fiber 250 comprises an optic fiber in a second curved position 1220. In one or more embodiments, the second angle may comprise any angle greater than the first angle. For example, the second angle may comprise a 90 degree angle.

Figure 12D:
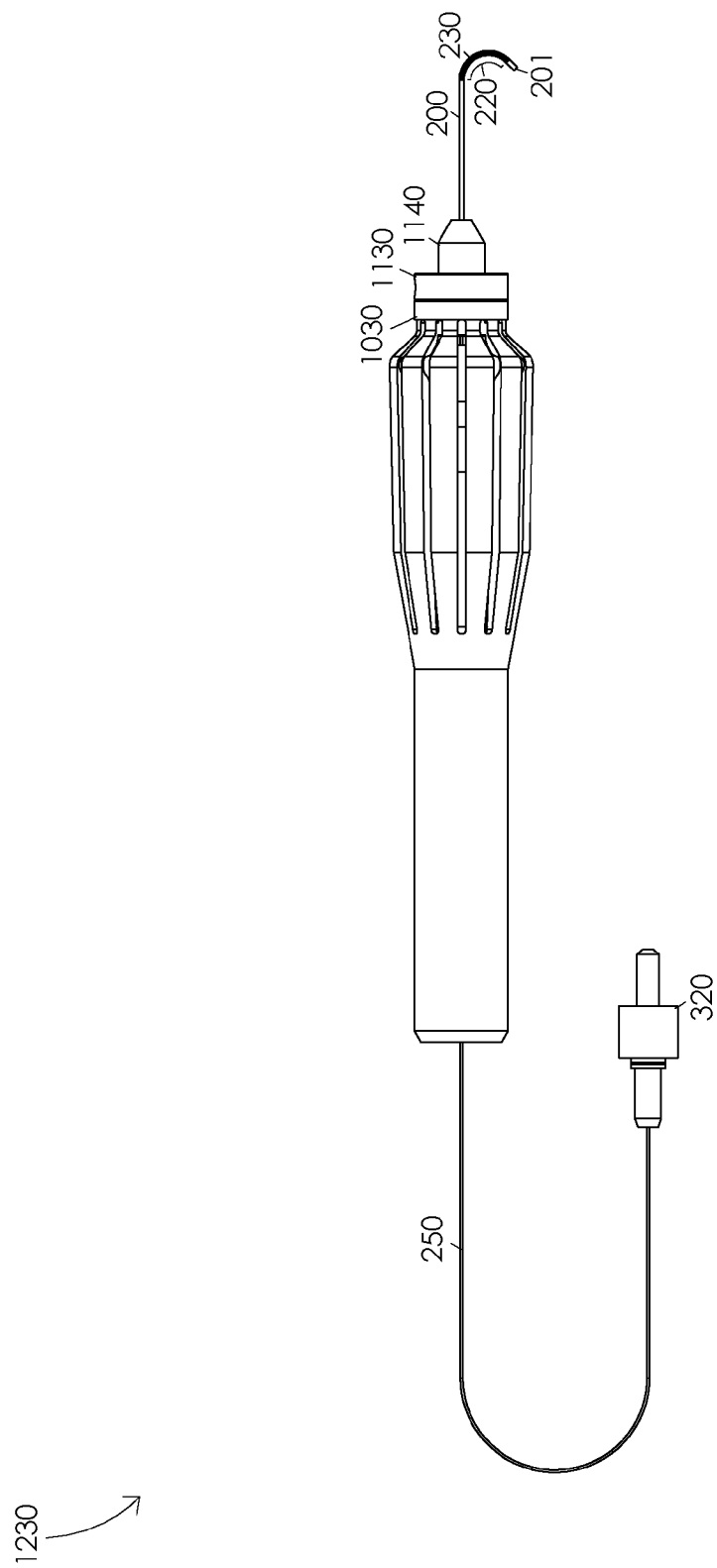

FIG. 12D illustrates an optic fiber in a third curved position 1230. In one or more embodiments, a decompression of actuation structure 1020 may be configured to gradually curve optic fiber 250 from an optic fiber in a second curved position 1220 to an optic fiber in a third curved position 1230. Illustratively, a decompression of actuation structure 1020 may be configured to gradually retract housing tube 200 relative to wire 340. In one or more embodiments, a retraction of housing tube 200 relative to wire 340 may be configured to actuate a portion of housing tube 200, e.g., a portion of housing tube 200 configured to generally straighten pre-formed curve 345, away from a portion of pre-formed curve 345. Illustratively, a retraction of housing tube 200 relative to wire 340 may be configured to actuate a portion of housing tube 200, e.g., first housing tube portion 220, over a portion of pre-formed curve 345. In one or more embodiments, a decompression of actuation structure 1020 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from an optic fiber in a second curved position 1220 to an optic fiber in a third curved position 1230. Illustratively, a line tangent to optic fiber distal end 251 may intersect a line tangent to housing tube proximal end 202 at a third angle, e.g., when optic fiber 250 comprises an optic fiber in a third curved position 1230. In one or more embodiments, the third angle may comprise any angle greater than the second angle. For example, the third angle may comprise a 135 degree angle.

Figure 12E:
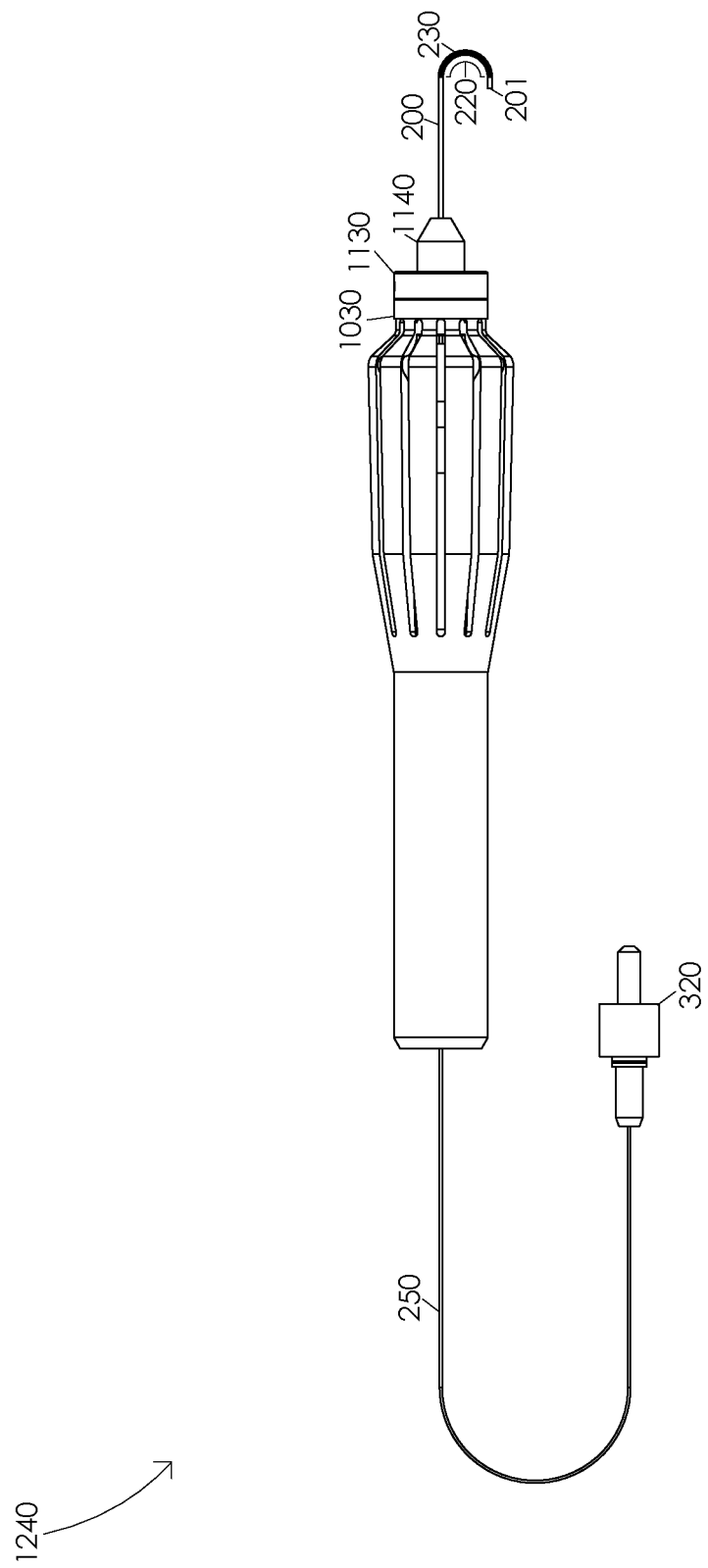

FIG. 12E illustrates an optic fiber in a fourth curved position 1240. In one or more embodiments, a decompression of actuation structure 1020 may be configured to gradually curve optic fiber 250 from an optic fiber in a third curved position 1230 to an optic fiber in a fourth curved position 1240. Illustratively, a decompression of actuation structure 1020 may be configured to gradually retract housing tube 200 relative to wire 340. In one or more embodiments, a retraction of housing tube 200 relative to wire 340 may be configured to actuate a portion of housing tube 200, e.g., a portion of housing tube 200 configured to generally straighten pre-formed curve 345, away from a portion of pre-formed curve 345. Illustratively, a retraction of housing tube 200 relative to wire 340 may be configured to actuate a portion of housing tube 200, e.g., first housing tube portion 220, over a portion of pre-formed curve 345. In one or more embodiments, a decompression of actuation structure 1020 may be configured to allow a portion of pre-formed curve 345 to gradually curve. Illustratively, a gradual curving of a portion of pre-formed curve 345 may be configured to gradually curve housing tube 200. In one or more embodiments, a gradual curving of housing tube 200 may be configured to gradually curve optic fiber 250, e.g., from an optic fiber in a third curved position 1230 to an optic fiber in a fourth curved position 1240. Illustratively, a line tangent to optic fiber distal end 251 may be parallel to a line tangent to housing tube proximal end 202, e.g., when optic fiber 250 comprises an optic fiber in a fourth curved position 1240.

In one or more embodiments, one or more properties of a steerable laser probe may be adjusted to attain one or more desired steerable laser probe features. For example, a length that housing tube 200 extends from inner nosecone 1120 may be adjusted to vary an amount of decompression of actuation structure 1020 configured to curve housing tube 200 to a particular curved position. Illustratively, a length of wire 340 may be adjusted to vary an amount of decompression of actuation structure 1020 configured to curve housing tube 200 to a particular curved position. In one or more embodiments, a stiffness of first housing tube portion 220 or a stiffness of second housing tube portion 230 may be adjusted to vary an amount of decompression of actuation structure 1020 configured to curve housing tube 200 to a particular curved position. Illustratively, a geometry of pre-formed curve 345 may be adjusted to vary an amount of decompression of actuation structure 1020 configured to curve housing tube 200 to a particular curved position. In one or more embodiments, a material comprising wire 340 or a material comprising a portion of wire 340, e.g., pre-formed curve 345, may be adjusted to vary an amount of decompression of actuation structure 1020 configured to curve housing tube 200 to a particular curved position. Illustratively, a material comprising first housing tube portion 220 or a material comprising second housing tube portion 230 may be adjusted to vary an amount of decompression of actuation structure 1020 configured to curve housing tube 200 to a particular curved position.

In one or more embodiments, a number of apertures in housing tube 200 may be adjusted to vary an amount of decompression of actuation structure 1020 configured to curve housing tube 200 to a particular curved position. Illustratively, a location of one or more apertures in housing tube 200 may be adjusted to vary an amount of decompression of actuation structure 1020 configured to curve housing tube 200 to a particular curved position. In one or more embodiments, a geometry of one or more apertures in housing tube 200 may be adjusted to vary an amount of decompression of action structure 1020 configured to curve housing tube 200 to a particular curved position. Illustratively, a geometry of one or more apertures in housing tube 200 may be uniform, e.g., each aperture of the one or more apertures may have a same geometry. In one or more embodiments, a geometry of one or more apertures in housing tube 200 may be non-uniform, e.g., a first aperture in housing tube 200 may have a first geometry and a second aperture in housing tube 200 may have a second geometry.

Illustratively, a distance that inner nosecone 1120 extends from handle proximal end 1002 may be adjusted to vary an amount of decompression of actuation structure 1020 configured to curve housing tube 200 to a particular curved position. For example, a distance that inner nosecone distal end 1121 extends from outer nosecone distal end 1131 may be adjusted to vary an amount of decompression of actuation structure 1020 configured to curve housing tube 200 to a particular curved position. In one or more embodiments, a geometry of actuation structure 1020 may be adjusted to vary an amount of decompression of actuation structure 1020 configured to curve housing tube 200 to a particular curved position. Illustratively, at least a portion of optic fiber 250 may be enclosed in an optic fiber sleeve configured to, e.g., protect optic fiber 250, vary a stiffness of optic fiber 250, vary an optical property of optic fiber 250, etc.

Illustratively, a stiffness of first housing tube portion 220 or a stiffness of second housing tube portion 230 may be adjusted to vary a bend radius of housing tube 200. In one or more embodiments, a stiffness of first housing tube portion 220 or a stiffness of second housing tube portion 230 may be adjusted to vary a radius of curvature of housing tube 200, e.g., when housing tube 200 is in a particular curved position. Illustratively, a number of apertures in housing tube 200 may be adjusted to vary a bend radius of housing tube 200. In one or more embodiments, a number of apertures in housing tube 200 may be adjusted to vary a radius of curvature of housing tube 200, e.g., when housing tube 200 is in a particular curved position. Illustratively, a location or a geometry of one or more apertures in housing tube 200 may be adjusted to vary a bend radius of housing tube 200. In one or more embodiments, a location or a geometry of one or more apertures in housing tube 200 may be adjusted to vary a radius of curvature of housing tube 200, e.g., when housing tube 200 is in a particular curved position.

In one or more embodiments, a location of pre-formed curve 345 of wire 340 or a location of first housing tube portion 220 of housing tube 200 may be adjusted to vary one or more steerable laser probe features. Illustratively, a location of pre-formed curve 345 or a location of first housing tube portion 220 may be adjusted wherein a portion of pre-formed curve 345 may be disposed within first housing tube portion 220. In one or more embodiments, a relative location of pre-formed curve 345 and first housing tube portion 220 may be adjusted wherein a decompression of actuation structure 1020 may retract first housing tube portion 220 away from pre-formed curve 345 and retract a portion of housing tube 200 configured to generally straighten pre-formed curve 345 over a portion of pre-formed curve 345. Illustratively, a decompression of actuation structure 1020 may be configured to gradually straighten housing tube 200. In one or more embodiments, a gradual straightening of housing tube 200 may be configured to gradually straighten optic fiber 250.

Illustratively, wire 340 may comprise any suitable structure, e.g., wire 340 may comprise a cable. For example, wire 340 may comprise a cable having a pre-formed curve 345. In one or more embodiments, wire 340 may be replaced with a tube or a portion of wire 340 may comprise an inner bore. For example, wire 340 may be replaced with a tube having a pre-formed curve 345.

Illustratively, a location of pre-formed curve 345 or a location of first housing tube portion 220 may be adjusted wherein a portion of pre-formed curve 345 may be disposed within a portion of housing tube 200 configured to generally straighten pre-formed curve 345. In one or more embodiments, a relative location of pre-formed curve 345 and first housing tube portion 220 may be adjusted wherein a compression of actuation structure 1020 may extend a portion of housing tube 200 configured to generally straighten pre-formed curve 345 away from pre-formed curve 345 and extend a portion of first housing tube portion 220 over a portion of pre-formed curve 345. Illustratively, a compression of actuation structure 1020 may be configured to gradually curve housing tube 200. In one or more embodiments, a gradual curving of housing tube 200 may be configured to gradually curve optic fiber 250.

Figure 13A:
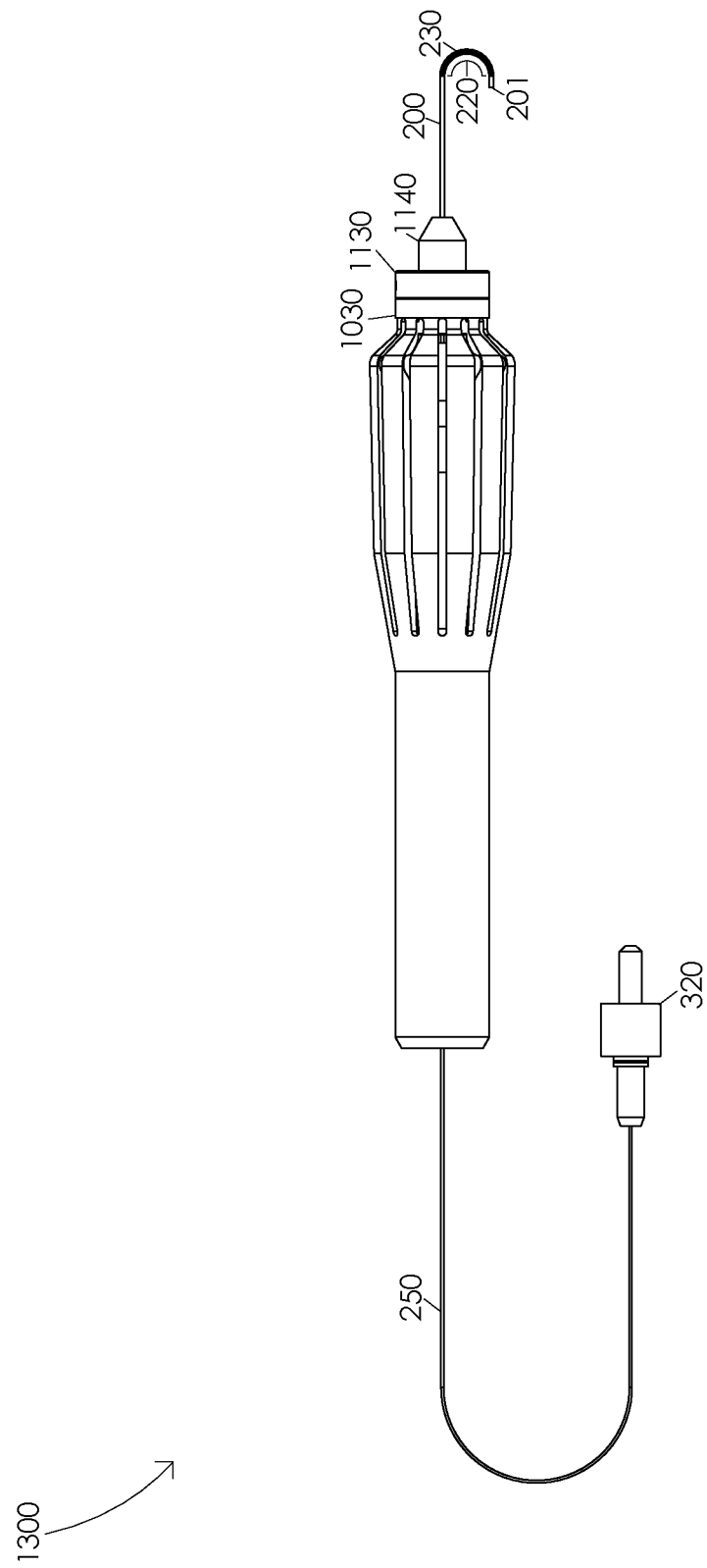
FIGS. 13A, 13B, 13C, 13D, and 13E illustrate a gradual straightening of an optic fiber.

FIGS. 13A, 13B, 13C, 13D, and 13E illustrate a gradual straightening of an optic fiber 250. FIG. 13A illustrates a fully curved optic fiber 1300. In one or more embodiments, optic fiber 250 may comprise a fully curved optic fiber 1300, e.g., when actuation ring 1030 is fully retracted relative to handle base 1010. Illustratively, optic fiber 250 may comprise a fully curved optic fiber 1300, e.g., when housing tube 200 is fully retracted relative to wire 340. In one or more embodiments, optic fiber 250 may comprise a fully curved optic fiber 1300, e.g., when actuation structure 1020 is fully decompressed. Illustratively, a line tangent to optic fiber distal end 251 may be parallel to a line tangent to housing tube proximal end 202, e.g., when optic fiber 250 comprises a fully curved optic fiber 1300.

Figure 13B:
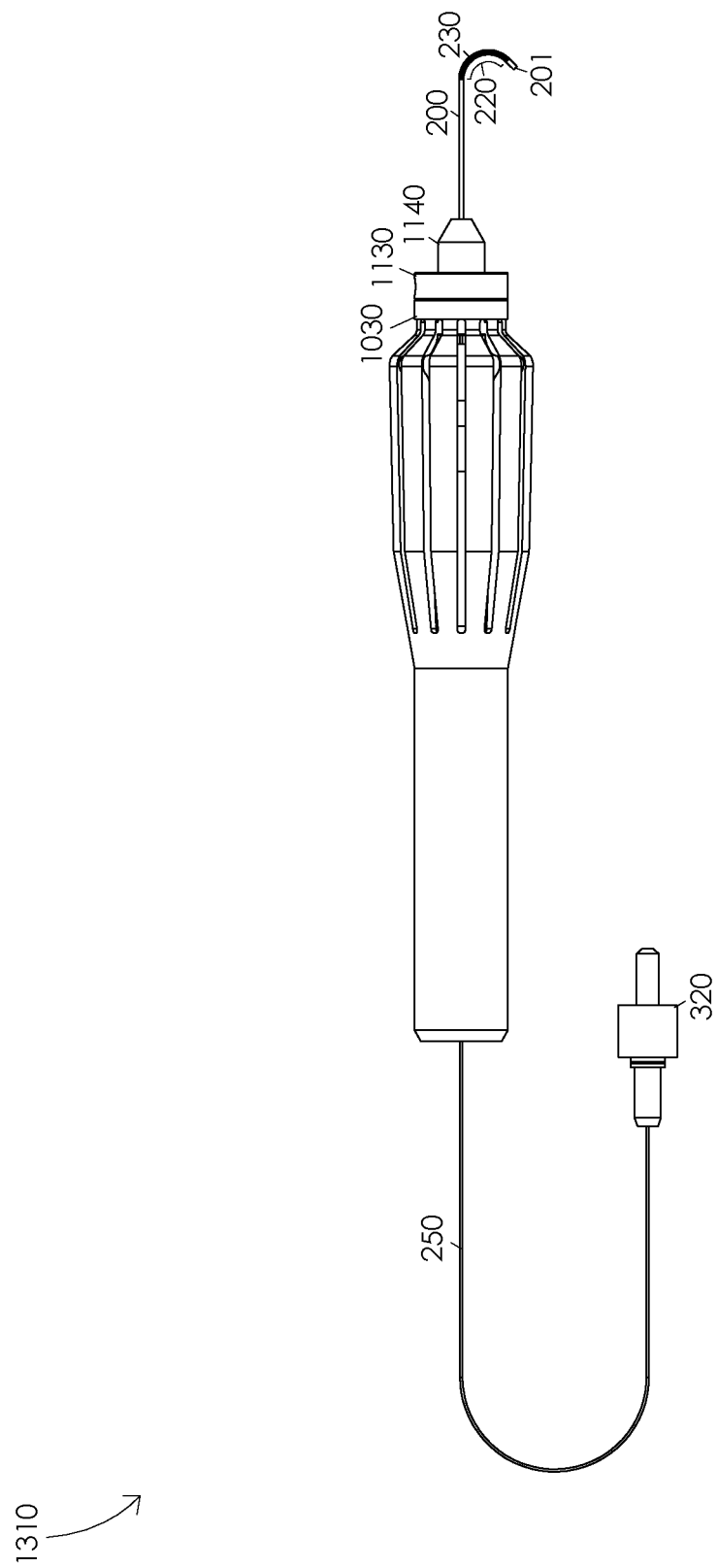

FIG. 13B illustrates an optic fiber in a first partially straightened position 1310. In one or more embodiments, a compression of actuation structure 1020 may be configured to gradually straighten optic fiber 250 from a fully curved optic fiber 1300 to an optic fiber in a first partially straightened position 1310. Illustratively, a compression of actuation structure 1020 may be configured to gradually extend housing tube 200 relative to wire 340. In one or more embodiments, an extension of housing tube 200 relative to wire 340 may be configured to extend a portion of housing tube 200, e.g., a portion of housing tube 200 configured to generally straighten pre-formed curve 345, over a portion of pre-formed curve 345. Illustratively, an extension of housing tube 200 relative to wire 340 may be configured to extend a portion of first housing tube portion 220 away from a portion of pre-formed curve 345. In one or more embodiments, a compression of actuation structure 1020 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from a fully curved optic fiber 1300 to an optic fiber in a first partially straightened position 1310. Illustratively, a line tangent to optic fiber distal end 251 may intersect a line tangent to housing tube proximal end 202 at a first partially straightened angle, e.g., when optic fiber 250 comprises an optic fiber in a first partially straightened position 1310. In one or more embodiments, the first partially straightened angle may comprise any angle less than 180 degrees. For example, the first partially straightened angle may comprise a 135 degree angle.

Figure 13C:
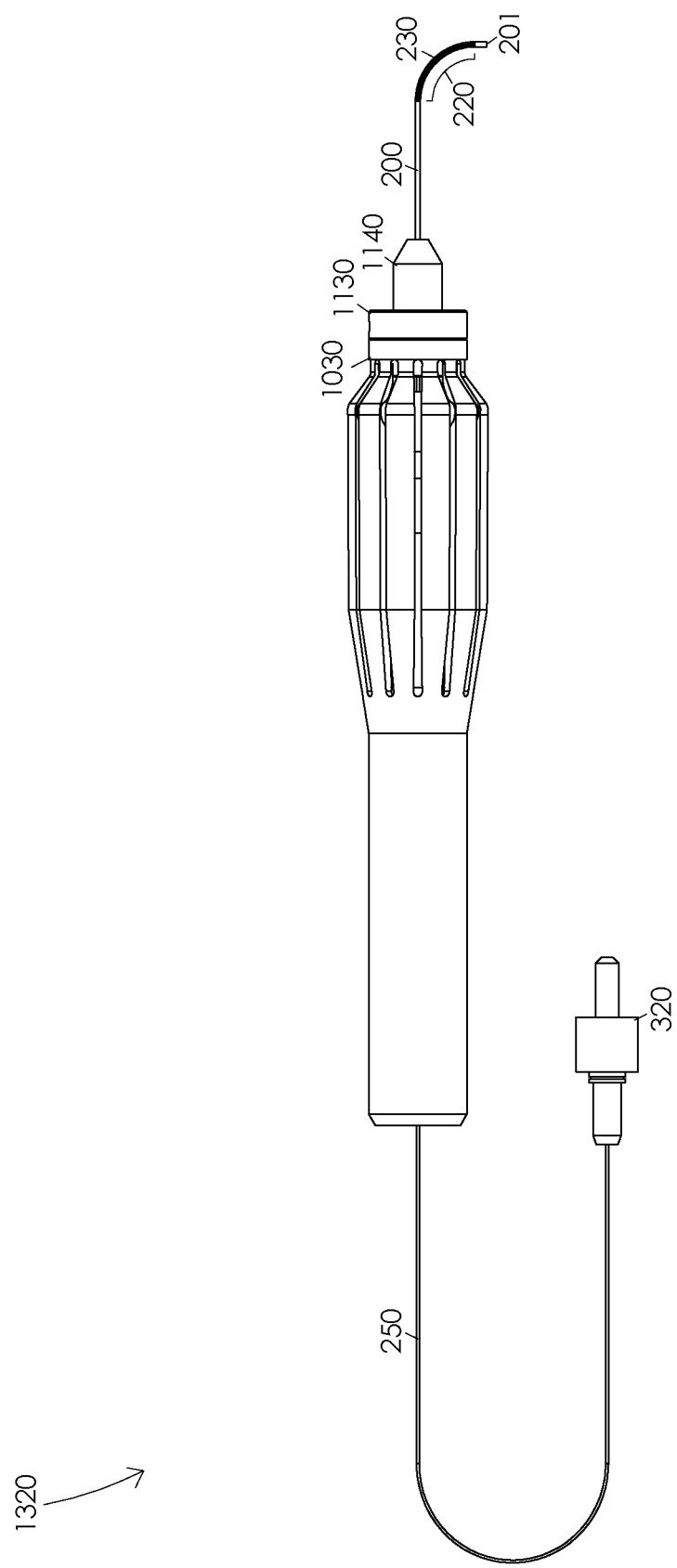

FIG. 13C illustrates an optic fiber in a second partially straightened position 1320. In one or more embodiments, a compression of actuation structure 1020 may be configured to gradually straighten optic fiber 250 from an optic fiber in a first partially straightened position 1310 to an optic fiber in a second partially straightened position 1320. Illustratively, a compression of actuation structure 1020 may be configured to gradually extend housing tube 200 relative to wire 340. In one or more embodiments, an extension of housing tube 200 relative to wire 340 may be configured to extend a portion of housing tube 200, e.g., a portion of housing tube 200 configured to generally straighten pre-formed curve 345, over a portion of pre-formed curve 345. Illustratively, an extension of housing tube 200 relative to wire 340 may be configured to extend a portion of first housing tube portion 220 away from a portion of pre-formed curve 345. In one or more embodiments, a compression of actuation structure 1020 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from an optic fiber in a first partially straightened position 1310 to an optic fiber in a second partially straightened position 1320. Illustratively, a line tangent to optic fiber distal end 251 may intersect a line tangent to housing tube proximal end 202 at a second partially straightened angle, e.g., when optic fiber 250 comprises an optic fiber in a second partially straightened position 1320. In one or more embodiments, the second partially straightened angle may comprise any angle less than the first partially straightened angle. For example, the second partially straightened angle may comprise a 90 degree angle.

Figure 13D:
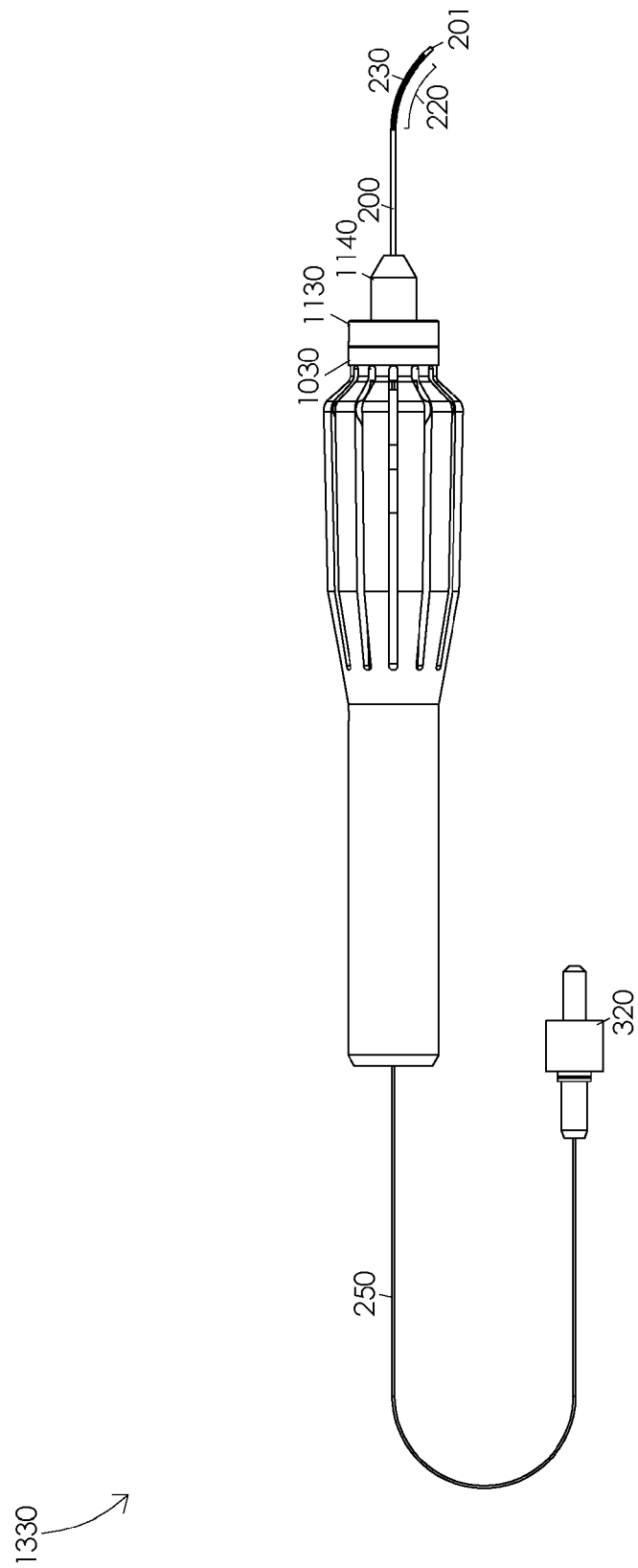

FIG. 13D illustrates an optic fiber in a third partially straightened position 1330. In one or more embodiments, a compression of actuation structure 1020 may be configured to gradually straighten optic fiber 250 from an optic fiber in a second partially straightened position 1320 to an optic fiber in a third partially straightened position 1330. Illustratively, a compression of actuation structure 1020 may be configured to gradually extend housing tube 200 relative to wire 340. In one or more embodiments, an extension of housing tube 200 relative to wire 340 may be configured to extend a portion of housing tube 200, e.g., a portion of housing tube 200 configured to generally straighten pre-formed curve 345, over a portion of pre-formed curve 345. Illustratively, an extension of housing tube 200 relative to wire 340 may be configured to extend a portion of first housing tube portion 220 away from a portion of pre-formed curve 345. In one or more embodiments, a compression of actuation structure 1020 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from an optic fiber in a second partially straightened position 1320 to an optic fiber in a third partially straightened position 1330. Illustratively, a line tangent to optic fiber distal end 251 may intersect a line tangent to housing tube proximal end 202 at a third partially straightened angle, e.g., when optic fiber 250 comprises an optic fiber in a third partially straightened position 1330. In one or more embodiments, the third partially straightened angle may comprise any angle less than the second partially straightened angle. For example, the third partially straightened angle may comprise a 45 degree angle.

Figure 13E:
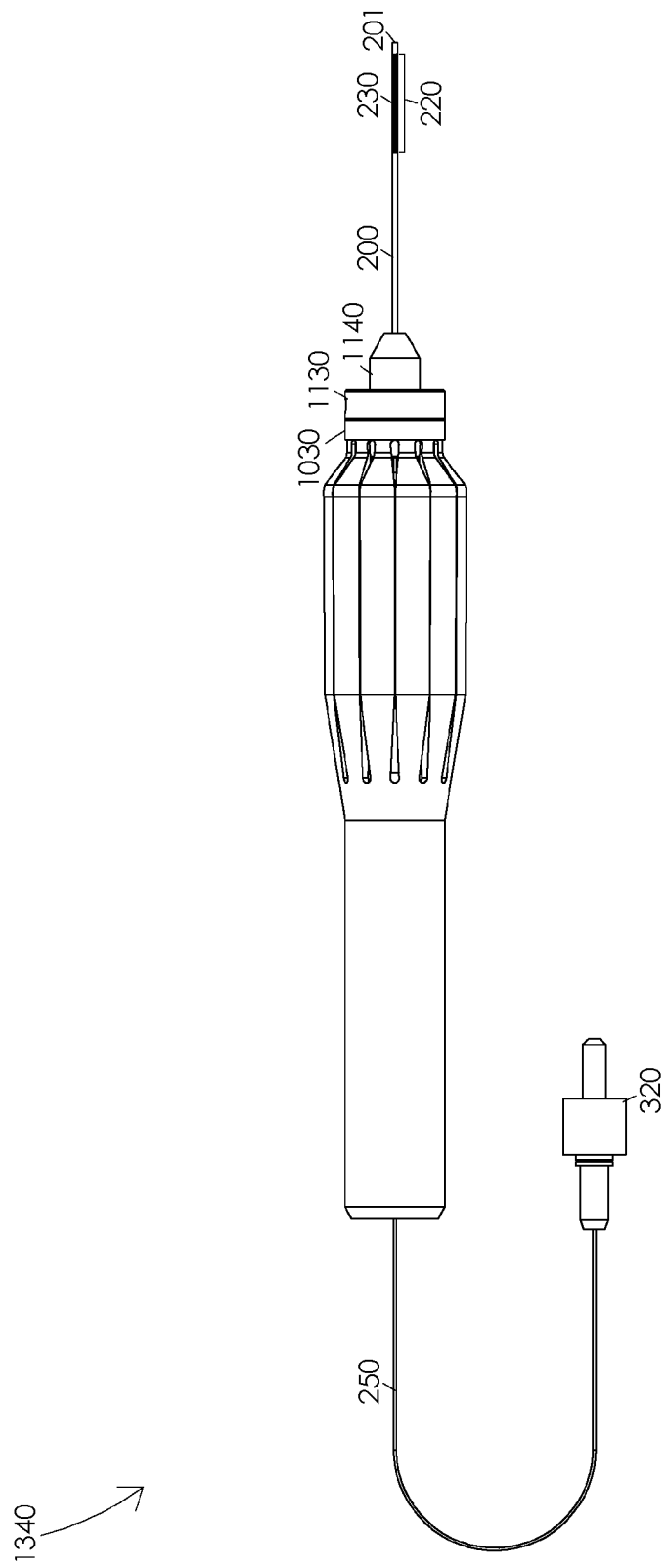

FIG. 13E illustrates an optic fiber in a fully straightened position 1340. In one or more embodiments, a compression of actuation structure 1020 may be configured to gradually straighten optic fiber 250 from an optic fiber in a third partially straightened position 1330 to an optic fiber in a fully straightened position 1340. Illustratively, a compression of actuation structure 1020 may be configured to gradually extend housing tube 200 relative to wire 340. In one or more embodiments, an extension of housing tube 200 relative to wire 340 may be configured to extend a portion of housing tube 200, e.g., a portion of housing tube 200 configured to generally straighten pre-formed curve 345, over a portion of pre-formed curve 345. Illustratively, an extension of housing tube 200 relative to wire 340 may be configured to extend a portion of first housing tube portion 220 away from a portion of pre-formed curve 345. In one or more embodiments, a compression of actuation structure 1020 may be configured to gradually straighten a portion of pre-formed curve 345. Illustratively, a gradual straightening of a portion of pre-formed curve 345 may be configured to gradually straighten housing tube 200. In one or more embodiments, a gradual straightening of housing tube 200 may be configured to gradually straighten optic fiber 250, e.g., from an optic fiber in a third partially straightened position 1330 to an optic fiber in a fully straightened position 1340. Illustratively, a line tangent to optic fiber distal end 251 may be parallel to a line tangent to housing tube proximal end 202, e.g., when optic fiber 250 comprises an optic fiber in a fully straightened position 1340.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 1000 to orient housing tube 200 in an orientation configured to cause a curvature of housing tube 200 within the particular transverse plane of the inner eye and varying an amount of decompression of actuation structure 1020. Illustratively, a surgeon may aim optic fiber distal end 251 at any target within a particular sagittal plane of the inner eye by, e.g., rotating handle 1000 to orient housing tube 200 in an orientation configured to cause a curvature of housing tube 200 within the particular sagittal plane of the inner eye and varying an amount of decompression of actuation structure 1020. In one or more embodiments, a surgeon may aim optic fiber distal end 251 at any target within a particular frontal plane of the inner eye by, e.g., varying an amount of decompression of actuation structure 1020 to orient a line tangent to optic fiber distal end 251 wherein the line tangent to optic fiber distal end 251 is within the particular frontal plane of the inner eye and rotating handle 1000. Illustratively, a surgeon may aim optic fiber distal end 251 at any target located outside of the particular transverse plane, the particular sagittal plane, and the particular frontal plane of the inner eye, e.g., by varying a rotational orientation of handle 1000 and varying an amount of decompression of actuation structure 1020. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it the object of the appended claims to cover all such variations and modifications as come within the true spirit and scope of the invention.

What is claimed is:

1. An instrument comprising:
   a handle having a handle distal end and a handle proximal end;
   an actuation structure of the handle;
   a plurality of actuation arms of the actuation structure;
   an extension mechanism of each actuation arm of the plurality of actuation arms;
   an inverted actuation joint of each actuation arm of the plurality of actuation arms;
   an actuation platform of the handle;
   a housing tube having a housing tube distal end and a housing tube proximal end, the housing tube having dimensions for performing ophthalmic surgical procedures;
   an optic fiber having an optic fiber distal end and an optic fiber proximal end, the optic fiber disposed within an inner bore of the handle and the housing tube;
   a wire having a wire distal end and a wire proximal end, the wire disposed within the housing tube, the wire proximal end fixed to the actuation platform;
   a pre-formed curve of the wire;
   a first housing tube portion of the housing tube, the first housing tube portion having a first stiffness; and
   a second housing tube portion of the housing tube, the second housing tube portion having a second stiffness wherein the second stiffness is greater than the first stiffness.

2. The instrument of claim 1 wherein a compression of the actuation structure is configured to curve the optic fiber.

3. The instrument of claim 2 wherein the compression of the actuation structure is configured to curve the optic fiber more than 90 degrees.

4. The instrument of claim 1 wherein a compression of the actuation structure is configured to straighten the optic fiber.

5. The instrument of claim 1 wherein a compression of the actuation structure is configured to retract the wire relative to the housing tube.

6. The instrument of claim 5 wherein the compression of the actuation structure is configured to curve the optic fiber.

7. The instrument of claim 6 wherein the compression of the actuation structure is configured to curve the optic fiber more than 90 degrees.

8. The instrument of claim 5 wherein the compression of the actuation structure is configured to straighten the optic fiber.

9. The instrument of claim 1 wherein a decompression of the actuation structure is configured to extend the wire relative to the housing tube.

10. The instrument of claim 9 wherein the decompression of the actuation structure is configured to curve the optic fiber.

11. The instrument of claim 10 wherein the decompression of the actuation structure is configured to curve the optic fiber more than 90 degrees.

12. The instrument of claim 9 wherein the decompression of the actuation structure is configured to straighten the optic fiber.

13. The instrument of claim 1 wherein at least a portion of the wire comprises Nitinol.

14. The instrument of claim 1 further comprising:
    an aperture of the first housing tube portion.

15. The instrument of claim 14 wherein the aperture is configured to produce the first stiffness.

16. The instrument of claim 1 further comprising:
    a slit of the first housing tube portion.

17. The instrument of claim 16 wherein the slit is configured to produce the first stiffness.

18. The instrument of claim 16 wherein the slit is configured to minimize a force of friction between the housing tube and a cannula.

19. The instrument of claim 18 wherein the slit is configured to minimize a the force of friction between the housing tube and the cannula as the housing tube is inserted into the cannula.

20. The instrument of claim 18 wherein the slit is configured to minimize a the force of friction between the housing tube and the cannula as the housing tube is extracted from the cannula.

* * * * *